(12) United States Patent
Marui et al.

(10) Patent No.: US 6,340,704 B1
(45) Date of Patent: Jan. 22, 2002

(54) CELL DIFFERENTIATION INDUCING AMIDE DERIVATIVES, THEIR PRODUCTION AND USE

(75) Inventors: Shogo Marui, Kobe; Masatoshi Hazama, Ikeda, both of (JP); Kohei Notoya, Montreal (CA); Koki Kato, Kobe (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/341,803

(22) PCT Filed: Apr. 23, 1998

(86) PCT No.: PCT/JP98/01871

§ 371 Date: Oct. 25, 1999

§ 102(e) Date: Oct. 25, 1999

(87) PCT Pub. No.: WO98/49155

PCT Pub. Date: Nov. 5, 1998

(30) Foreign Application Priority Data

Apr. 25, 1997 (JP) .............................. 9-109915

(51) Int. Cl.$^7$ ...................... A61K 31/357; A61K 31/36; A61K 31/166; C07D 317/70; C07C 235/06; A61P 25/28

(52) U.S. Cl. ...................... 514/463; 514/422; 514/450; 514/453; 514/454; 514/464; 514/338; 514/321; 514/254.11; 514/236.8; 514/617; 544/148; 544/378; 546/197; 546/283.7; 548/526; 549/432; 549/433; 549/441; 549/358; 549/359; 564/172

(58) Field of Search .................... 549/433, 441, 549/432, 358, 359; 514/463, 464, 450, 453, 454, 236.8, 254.11, 338, 321, 422, 617; 564/172; 544/148, 378; 546/283.7, 197; 548/526

(56) References Cited

U.S. PATENT DOCUMENTS 3,932,416 A    1/1976   Bays ...................... 260/287 F
4,499,094 A    2/1985   Dubroeucq ................. 514/301
5,541,193 A *  7/1996   Kawai .................... 514/291
5,627,200 A *  5/1997   Kreutter ................. 514/367
5,654,276 A *  8/1997   Barrett .................. 514/13

FOREIGN PATENT DOCUMENTS

DE         2332731        3/1974
EP         0399814       11/1990
EP         0634169        1/1995
JP         03153625       7/1991
WO       WO 96/25929      8/1996

OTHER PUBLICATIONS

Bundgaard H. Design of prodrugs. Elsevier. Amsterdam-–New York–Oxford. pp. 27–35, 1985.*

* cited by examiner

Primary Examiner—Evelyn Mei Huang
(74) Attorney, Agent, or Firm—Mark Chao; Elaine M. Ramesh

(57) ABSTRACT

The present invention provides a compound represented by the formula:

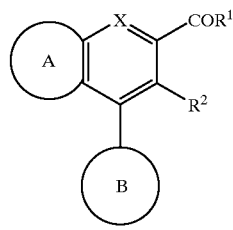

wherein $R^1$ is an amino group which may be substituted; $R^2$ is a hydrogen atom or a lower alkyl group which may be substituted; X is a methyne group which may be substituted or $N(O)m$ (m is 0 or 1); a ring A is a homo- or hetero-cycle which is substituted by a halogen atom, lower alkyl, lower alkoxy or lower alkylenedioxy; and a ring B is a homo- or hetero-cycle which may be substituted; or a salt thereof, which exhibits excellent cell differentiation-inducing action and cell differentiation-inducing factor action-enhancing action, and is useful in the treatment and prevention of various nerve diseases or bone/joint diseases.

20 Claims, No Drawings

CELL DIFFERENTIATION INDUCING AMIDE DERIVATIVES, THEIR PRODUCTION AND USE

This application is the National Stage of International Patent Application Ser. No. PCT/JP98/01871, filed Apr. 23, 1998.

TECHNICAL FIELD

The present invention relates to amide derivatives exhibiting excellent cell differentiation-inducing actions or cell differentiation-inducing action-enhancing actions such as bone morphogenetic protein (BMP) action or BMP-enhancing action or neurotrophic factor (NTF) actions (e.g., nerve growth factor (NGF) action, brain-derived neurotrophic factor (BDNF) action, neurotrophin-3 (NT-3) action and glial cell line-derived neurotrophic factor (GDNF) action) or NTF-enhancing action, a method of their production and a pharmaceutical composition containing them.

BACKGROUND ART

Bone morphogenetic protein (BMP), isolated from demineralized bone, is the only group of protein factors known to be capable of ectopic bone induction. It is therefore useful as an osteogenesis promoter in bone fracture healing, bone reconstruction etc. (A. E. Wang, Trends in Biotechnology, Vol. 11, pp. 379–383 (1993)).

To date, a number of such substances with BMP action-enhancing activity have been reported, i.e., retinoic acid, vitamin D3, estrogen and glucocorticoid (V. Rosen & R. S. Thies, Trends in Genetics, Vol. 8, pp. 97–102 (1992); Y. Takuwa et al., Biochemical and Biophysical Research Communications, Vol. 174, pp. 96–101 (1991)).

Also, because BMP directly promotes osteoblast differentiation, it is assumed to play a role as a coupling factor in bone remodelling, and is thought to be closely involved in bone metabolism. Also, it has been reported that the BMP content in bone substrate in aged animals has been considerably decreased (M. L. Urist, Bone and Mineral Research, Vol. 6 (ed. by W. A. Peck), pp. 57–112, Elsevier, 1989), suggesting that BMP is profoundly involved in the maintenance of bone mass. This suggests that BMP is promising as a therapeutic drug for various bone diseases such as osteoporosis. However, because BMP is normally present in trace amounts in living body so that its supply is limited, and because BMP is a protein so that a problem arises in its administration, the target diseases to which it is applicable are limited.

In addition, BMP has been reported to possess an activity like that of neurotrophic factors (V. M. Paralkar et al., Journal of Cell Biology, Vol. 119, pp. 1,721–1,728 (1992)). Also, it is known that the BMP gene is strongly expressed in brain tissue (E. Ozkaynak et al., Biochemical and Biophysical Research Communications, Vol. 179, pp. 116–123 (1991)). Also, BMP has been suggested as playing an important role in neural tube formation in embryogenesis (K. Basler et al., Cell. Vol. 73, pp. 687–702 (1993)).

Neurotrophic factors, a group of proteinous factors playing an important role in the survival and functional expression of neurons, include nerve growth factor (NGF), brain-derived neurotrophic factor (BDNF), neurotrophin-3 (NT-3) and glial cell line-derived neurotrophic factor (GDNF). NGF promotes the differentiation and maturation of the sympathetic ganglion cells and dorsal root ganglion cells of the neural tube in the peripheral nervous system (A. M. Davies & R. M. Lindsay, Developmental Biology, Vol. 111, pp. 62–72 (1985); R. Levi-Montalcini, EMBO Journal, Vol. 6, pp. 1,145–1,154 (1987)), and acts on the cholinergic neurons of septa (procephalic basal ganglia) in the central nervous system (H. Gnahn et al., Developmental Brain Research, Vol. 9, pp. 45–52 (1983); H. Hatanaka & H. Tsukui, Developmental Brain research, Vol. 30, pp. 47–56 (1986); F. Hefti, Journal of Neuroscience, Vol. 6, pp. 2,155–2,162 (1986)). NGF is essential for the maintenance of nervous function even after completion of neuron differentiation. BDNF acts on the dorsal spinal root ganglion cells and nodal ganglion cells in the peripheral nervous system but does not act on sympathetic ganglion cells (R. M. Lindsay & H. Rohrer, Developmental Biology, Vol. 112, pp. 30–48 (1985); R. M. Lindsay et al., Developmental Biology, Vol. 112, pp. 319–328(1985); A. M. Davies et al., Journal of Neuroscience, Vol. 6, pp. 1,897–1,904 (1986)). On the other hand, in the central nervous system, BDNF acts on the cholinergic neurons and GABA (γ-aminobutyric acid)-acting neurons of septa, and the dopaminergic neurons of the mesencephalon (R. F. Alderson et al., Neuron, Vol. 5, pp. 297–306 (1990); C. Hyman et al., Nature, Vol. 350, pp. 230–232 (1991); B. Knusel et al., Proceedings of the National Academy of Sciences of the United States of America, Vol. 88, pp. 961–965 (1991)). NT-3 is characterized by potent action on the sensory neurons derived from the neural plate, although its action overlaps those of NGF and BDNF in the peripheral nervous system (P. Ernfors et al., Proc. Natl. Acad. Sci. USA, Vol. 87, pp. 5,454–5,458 (1990); A. Rosenthal et al., Neuron, Vol. 4, pp. 767–773 (1990)). However, there are no known neurons of the central nervous system that respond to NT-3.

As a substance exhibiting NGF action, sabeluzole [4-(2-benzothiazolylmethylamino)-α(p-fluorophenoxy)methyl]-1-(piperidine) ethanol] has been reported (New Current, Vol. 4, No. 26, p. 14 (1993)]; in addition, SR57746A [Neuroscience, Vol. 55, p. 629 (1993)), T-588 (Japanese Patent Unexamined Publication No. 95070/1992) and MS430 (Journal of University of Occupational and Environmental Health, Vol. 17, p. 131 (1995)) have also been reported to enhance NGF action. Also, as compounds exhibiting NGF secretion-inducing action, steroids, catechols and cytokines have been reported (Experimental Neurology, Vol. 124, pp. 36–42 (1993)).

Alzheimer dementia has been characterized by extensive lesion and exfoliation of cerebral cortical neurons, as well as degeneration and exfoliation of cholinergic neurons of the basal ganglia, including the septal area; NGF and new neurotrophic factors are considered as candidates for therapeutic drugs therefor (F. Hefti & W. J. Weiner, Annual Neurology, Vol. 20, pp. 275–281 (1986)). Because these neurothrophic factors are proteins, however, their application are subject to limitation.

Also, low-molecular compounds known to promote osteoblast proliferation and differentiation include, for example, ipriflavone (K. Notoya et al., Journal of Bone and Mineral Research, Vol. 9, pp. 395–400 (1994)) and vitamin K2 (Y. Akedo et al., Biochemical and Biophysical Research, Vol. 187, pp. 814–820 (1992)) but these do not possess ectopic bone induction capability as does BMP.

Compounds known to exhibit actions like those of neurotrophic factors, such as the extension of neurites and neuron survival, include lactastatin (S. Omura et al., Journal of Antibiotics, Vol. 40, pp. 113–117 (1991)), retinoic acid (M. Minana et al., Proceedings of the National Academy of Science of the USA, Vol. 876, pp. 4335–4339 (1990)), staurosporin (T. B. Shea et al. Journal of Neuroscience Research, Vol. 33, pp. 398–407 (1990)), K252a (G. D. Borasio et al., Neuroscience Letters, Vol. 108, pp. 207–212 (1990)), and MS818 (A. Awaya et al., Biological and Pharmaceutical Bulletin, Vol. 16, pp. 248–253 (1993)).

(1) A naphthalenecarboxamide represented by the formula:

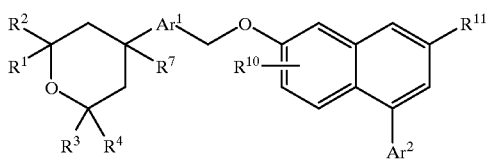

wherein $Ar^1$ represents allylene-$(R^8)_2$ ($R^8$: a hydrogen atom, halogen, lower alkyl, hydroxy, lower alkoxy etc.); $Ar^2$ represents aryl-$(R^9)_2$ ($R^9$: a hydrogen atom, halogen, lower alkyl, hydroxy, lower alkoxy etc.); $R^1$ represents a hydrogen atom, lower alkyl, hydroxy or lower alkoxy; $R^2$ represents a hydrogen atoms, lower alkyl or a group which forms =O in cooperation with $R^1$; $R^3$ represents a hydrogen atom, halogen, lower alkyl, hydroxy, lower alkoxy or the like; $R^4$ represents a hydrogen atom or lower alkyl; $R^7$ represents a hydrogen atom, halogen, lower alkyl, hydroxy, lower alkoxy or the like; each of $R^{10}$ and $R^{11}$ represents a hydrogen atom, halogen, lower alkyl, hydroxy, a lower alkoxy, $CON(R^{16})_2$ ($R^{16}$ represents a hydrogen atom, lower alkyl or $OR^{13}$ ($R^{13}$ is a hydrogen atom or lower alkyl)) or the like; is disclosed in U.S. Pat. No. 5,308,852;

(2) a compound represented by the formula:

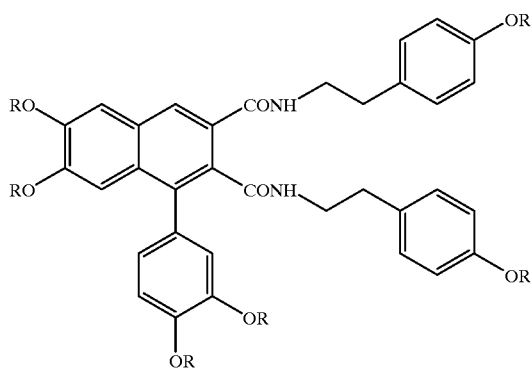

wherein R represents a hydrogen atom, acetyl or methyl, is disclosed in Japanese Patent Unexamined Publication No. 153625/1991; and (3) a compound represented by the formula:

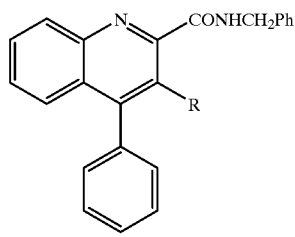

R: $CO_2H$, $CH_2Cl$, $CH_2OH$ is disclosed in Heterocycles, Vol. 38, pp. 103–111 (1994), etc.

However, the publications disclosing the carboxamide compounds (1) to (3) above give no description of cell differentiation-inducing action or cell differentiation-inducing factor action-enhancing action, bone morphogenetic protein (BMP) action or BMP action-enhancing action, neurotrophic factor (NTF) action or NTF action-enhancing action.

In view of the above aspects, any compounds which enhance BMP action, for example, would enhance the action of BMP present in vivo or administered to the living body and would be useful as a therapeutic drug for bond diseases as described above. However, conventional substances, when administered in vivo, are known to promote bone resorption and have side effects such as hypercalcemia and ovarian cancer onset, and are not always appropriate for use as therapeutic drugs for bone diseases.

On the other hand, any compounds which enhance the action of NGF, for example, would enhance the action of NGF present in vivo or administered to the living body and would be useful as a therapeutic drug for dementia and peripheral neuropathy; however, their action mechanism remains to be clarified; clinical studies have demonstrated some such substances have side effects such as headache, dizziness and fatigue, others remain to be proven effective in humans, others possess insufficient activity, others possess nervous toxicity, and others exhibit pharmaceutically undesirable actions such as immunity reduction, hypercalcemia and boner resorption promotion, so they are unsatisfactory for practical application.

Moreover, because cell differentiation induction factors represented by BMP or neurotrophic factors are proteins, their administration to the living body are subject to limitation. Compounds which enhance the action of cell differentiation induction factors present in vivo or administered to the living body are therefore preferably of low molecular weight.

Also, even if the compound itself possesses cell differentiation induction factor action, as exemplified by BMP and neurotrophic factors, provided that is of low molecular weight, it is believed to serve advantageously over BMP and neurotrophic factors in terms of administration to the living body, and other aspects, as an osteogenesis promoter in bone fracture healing and bone reconstruction, and as a therapeutic drug for dementia and peripheral neuropathy.

In other words, conventional compounds that act like neurothrophic factors, as well as enhance their action, have not been proven to be effective in humans, and other compounds are unsatisfactory for practical application in terms of activity potency, toxicity, etc.

There is therefore strong demand for the development of compounds differing from the above-described known substances, possession excellent BMP action or neurotrophic factor action or enhancing such action, and serving well as a pharmaceutical.

Against this technical background, the present inventors made extensive investigation, and for the firs time succeeded in creating a compound characterized by a unique chemical structure with a carbamoyl group —$COR^1$ which may be substituted, and represented by the formula:

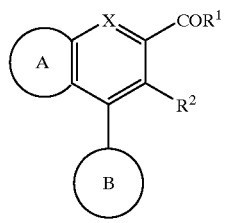

(I)

wherein $R^1$ is an amino group which may be substituted; $R^2$ is a hydrogen atom or a lower alkyl group which may be substituted; X is a methine group which may be substituted or N(O)m (m is 0 or 1); a ring a is a homo- or hetero-cycle which is substituted by a halogen atom, lower alkyl, lower alkoxy or lower alkylenedioxy group; and a ring B is a homo- or hetero-cycle which may be substituted; or a salt thereof, and found that this compound, represented by formula (I), or a salt thereof unexpectedly exhibits BMP or neurotrophic factor action, specifically enhances the actions of BMP and neurotrophic factors, such as osteoblast and neuron differentiation and neuron survival, and is a low-molecular compound useful as an agent for inducing a cell differentiation or enhancing an action of induction factor of cell differentiation etc., and is fully satisfactory as a pharmaceutical. The present inventors made further investigation based on this finding, and developed the present invention.

DISCLOSURE OF INVENTION

The present invention provides:

(1) A compound represented by the formula:

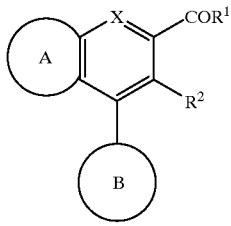

wherein $R^1$ is an amino group which may be substituted; $R^2$ is a hydrogen atom or a lower alkyl group which may be substituted; X is a methyne group which may be substituted or N(O)m (m is 0 or 1); a ring A is a homo- or hetero-cycle which is substituted by a halogen atom, lower alkyl, lower alkoxy or lower alkylenedioxy; and a ring B is a homo- or hetero-cycle which may be substituted; or a salt thereof, (2) The compound as defined in (1) wherein $R^1$ is (I) an amino group which may be substituted by (a) a $C_{1-6}$ alkyl group, $C_{2-6}$ alkenyl group, $C_{2-6}$ alkynyl group, $C_{3-6}$ cycloalkyl group, $C_{6-14}$ aryl group or $C_{7-16}$ aralkyl group, which may be substituted by a group selected from the group consisting of (i) a halogen atom, (ii) $C_{1-3}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) optionally halogenated $C_{1-6}$ alkoxy, (x) optionally halogenated $C_{1-6}$ alkylthio, (xi) hydroxy, (xii) amino, (xiii) mono-$C_{1-6}$ alkyl amino, (xiv) di-$C_{1-6}$ alkyl amino, (xv) 5 or 6 membered cyclic amino, (xvi) acyl amino selected from $C_{1-6}$ alkoxy-carbonyl amino, mono-$C_{1-6}$ alkylaminocarbonyl amino, $C_{1-6}$ alkylcarbonyl amino and $C_{1-6}$ alkylsulfonyl amino, (xvii) $C_{1-6}$ alkylcarbonyl, (xviii) carboxyl, (xix) $C_{1-6}$ alkoxy-carbonyl, (xx) carbamoyl, (xxi) mono-$C_{1-6}$ alkyl-carbamoyl, (xxii) di-$C_{1-6}$ alkyl-carbamoyl, (xxiii) $C_{6-10}$ aryl-carbamoyl, (xxiv) sulfo, (xxv) $C_{1-6}$ alkyl sulfonyl, (xxvi) $C_{6-10}$ aryl and (xvii) $C_{6-10}$ aryloxy, (b) a hydroxy group which may be substituted by a $C_{1-6}$ alkyl group, $C_{2-6}$ alkenyl group, $C_{2-6}$ alkynyl group, $C_{3-6}$ cycloalkyl group, $C_{6-14}$ aryl group or $C_{7-16}$ aralkyl group, which may be substituted by a group selected from the group consisting of (i) a halogen atom, (ii) $C_{1-3}$ alkylenedioxy, (iii) nitro, (iv) cyano, (v) optionally halogenated $C_{1-6}$ alkyl, (vi) optionally halogenated $C_{2-6}$ alkynyl, (viii) $C_{3-6}$ cycloalkyl, (ix) optionally halogenated $C_{1-6}$ alkoxy, (x) optionally halogenated $C_{1-6}$ alkylthio, (xi) hydroxy, (xii) amino, (xiii) mono-$C_{1-6}$ alkyl amino, (xiv) di-$C_{1-6}$ alkyl amino, (xv) 5 or 6 membered cyclic amino, (xvi) acyl amino selected from $C_{1-6}$ alkoxy-carbonyl amino, mono-$C_{1-6}$ alkylaminocarbonyl amino, $C_{1-6}$ alkylcarbonyl amino and $C_{1-6}$ alkylsulfonyl amino, (xvii) $C_{1-6}$ alkylcarbonyl, (xviii) carboxyl, (xix) $C_{1-6}$ alkoxy-carbonyl, (xx) carbamoyl, (xxi) mono-$C_{1-6}$ alkyl-carbamoyl, (xxii) di-$C_{1-6}$ alkyl-carbamoyl, (xxiii) $C_{6-10}$ aryl-carbamoyl, (xxiv) sulfo, (xxv) $C_{1-6}$ alkyl sulfonyl, (xxvi) $C_{6-10}$ aryl and (xxvii) $C_{6-10}$ aryloxy, or (c) an amino group which may be substituted by an acyl group represented by any one of the formula: —(C=O)—$R^7$, —$SO_2$—$R^7$, —SO—$R^7$, —(C=O)N$R^8R^7$, —(C=O)O—$R^7$, —(C=S)O—$R^7$ or —(C=S)N$R^8R^7$ wherein $R^7$ is (a) hydrogen atom or (b) a $C_{1-6}$ alkyl group, $C_{2-6}$ alkenyl group, $C_{2-6}$ alkynyl group, $C_{3-6}$ cycloalkyl group, $C_{6-14}$ aryl group or $C_{7-16}$ aralkyl group, which may be substituted by a group selected from the group consisting of (i) a halogen atom, (ii) $C_{1-3}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) optionally halogenated $C_{1-6}$ alkoxy, (x) optionally halogenated $C_{1-6}$ alkylthio, (xi) hydroxy, (xii) amino, (xiii) mono-$C_{1-6}$ alkyl amino, (xiv) di-$C_{1-6}$ alkyl amino, (xv) 5 or 6 membered cyclic amino, (xvi) acyl amino selected from $C_{1-6}$ alkoxy-carbonyl amino, mono-$C_{1-6}$ alkylaminocarbonyl amino, $C_{1-6}$ alkylcarbonyl amino and $C_{1-6}$ alkylsulfonyl amino, (xvii) $C_{1-6}$ alkylcarbonyl, (xviii) carbonyl, (xix) $C_{1-6}$ alkoxy-carbonyl, (xx) carbamoyl, (xxi) mono-$C_{1-6}$ alkyl-carbamoyl, (xxii) di-$C_{1-6}$ alkyl-carbamoyl, (xxiii) $C_{6-10}$ aryl-carbamoyl, (xxiv) sulfo, (xxv) $C_{1-6}$ alkyl sulfonyl, (xxvi) $C_{6-10}$ aryl and (xxvii) $C_{6-10}$ aryloxy, and $R^8$ is hydrogen atom or a $C_{1-6}$ alkyl group, or (II) a group formed by removing a hydrogen atom from a nitrogen atom of a 5 to 9 membered nitrogen-containing heterocycle which may have 1 to 3 hetero atoms selected from a nitrogen atom, an oxygen atom and a sulfur atom, other than carbon atoms and one nitrogen atom, and the nitrogen-containing heterocycle may be substituted by a group selected from the group consisting of (i) a halogen atom, (ii) $C_{1-3}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) optionally halogenated $C_{1-6}$ alkoxy, (x) optionally halogenated $C_{1-6}$ alkylthio, (xi) hydroxy, (xii) amino, (xiii) mono-$C_{1-6}$ alkyl amino, (xiv) di-$C_{1-6}$ alkyl amino, (xv) 5 or 6 membered cyclic amino, (xvi) acyl amino selected from $C_{1-6}$ alkoxycarbonyl amino, mono-$C_{1-6}$ alkylaminocarbonyl amino, $C_{1-6}$ alkylcarbonyl, (xviii) carboxyl, (xix) $C_{1-6}$ alkoxycarbonyl, (xx) carbamoyl, (xxi) mono-$C_{1-6}$ alkyl-carbamoyl, (xxii) di-$C_{1-6}$ alkyl-carbamoyl, (xxiii) $C_{6-10}$ aryl-carbamoyl, (xxiv) sulfo, (xxv) $C_{1-6}$ alkyl sulfonyl, (xxvi) $C_{6-10}$ aryl and (xxvii) $C_{6-10}$ aryloxy; $R^2$ is (a) a hydrogen atom or (b) a $C_{1-6}$ alkyl group which may be substituted by a group selected from that consisting of (i) a halogen atom, (ii) $C_{1-3}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) optionally halogenated $C_{1-6}$ alkoxy, (x) optionally halogenated $C_{1-6}$ alkylthio, (xi) hydroxy, (xii) amino, (xiii) mono-$C_{1-6}$ alkyl amino, (xiv) di-$C_{1-6}$ alkyl amino, (xv) 5 or 6 membered cyclic amino, (xvi) acyl amino selected from $C_{1-6}$ alkoxycarbonyl amino, mono-$C_{1-6}$ alkylaminocarbonyl amino, $C_{1-6}$ alkylcarbonyl amino and $C_{1-6}$ alkylsulfonyl amino, (xvii) $C_{1-6}$ alkylcarbonyl, (xviii) carboxyl, (xix) $C_{1-6}$ alkoxy-carbonyl, (xx) carbamoyl, (xxi) mono-$C_{1-6}$ alkyl-carbamoyl, (xxii) di-$C_{1-6}$ alkyl-carbamoyl, (xxiii) $C_{6-10}$ aryl-carbamoyl, (xxiv) sulfo, (xxv) $C_{1-6}$ alkyl sulfonyl, (xxvi) $C_{6-10}$ aryl and (xxvii) $C_{6-10}$ aryloxy; X is N(O)m (m is 0 or 1) or $CR^{6"}$ wherein $R^{6"}$ is (a) a hydrogen atom, (b) a halogen atom, (c) a $C_{1-6}$ alkyl group, $C_{2-6}$ alkenyl group, $C_{2-6}$ alkynyl group, $C_{3-6}$ cycloalkyl group, $C_{6-14}$ aryl group or $C_{7-16}$ aralkyl group which may be substituted by a group selected from the group consisting of (i) a halogen atom, (ii) $C_{1-3}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) optionally halogenated $C_{1-6}$ alkoxy, (x) optionally halogenated $C_{1-6}$ alkylthio, (xi) hydroxy, (xii) amino, (xiii) mono-$C_{1-6}$ alkyl amino, (xiv) di-$C_{1-6}$ alkyl amino, (xv) 5 or 6 membered cyclic amino, (xvi) acyl amino selected from $C_{1-6}$ alkoxy-carbonyl amino, mono-$C_{1-6}$ alkylaminocarbonyl amino, $C_{1-6}$ alkylcarbonyl amino and $C_{1-6}$ alkylsulfonyl amino, (xvii) $C_{1-6}$ alkylcarbonyl, (xviii) carboxyl, (xix) $C_{1-6}$ alkoxy-carbonyl, (xx) carbamoyl, (xxi) mono-$C_{1-6}$ alkyl-carbamoyl, (xxii) di-$C_{1-6}$ alkyl-carbamoyl, (xxiii) $C_{6-10}$ aryl-carbamoyl, (xxiv) sulfo, (xxv) $C_{1-6}$ alkyl sulfonyl, (xxvi) $C_{6-10}$ aryl and (xxvii) $C_{6-10}$ aryloxy or (d) —$OR^{6'''}$ wherein $R^{6'''}$ is (a') a hydrogen atom or (b') a $C_{1-6}$ alkyl group, $C_{2-6}$ alkenyl group, $C_{2-6}$ alkynyl group, $C_{3-6}$ cycloalkyl group, $C_{6-14}$ aryl group or $C_{7-16}$ aralkyl group which may be substituted by a group selected from the group consisting of (i) a halogen atom, (ii) $C_{1-3}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) optionally halogenated $C_{1-6}$ alkoxy, (x) optionally halogenated $C_{1-6}$ alkylthio, (xi) hydroxy, (xii) amino, (xiii) mono-$C_{1-6}$ alkyl amino, (xiv) di-$C_{1-6}$ alkyl amino, (xv) 5 or 6 membered cyclic amino, (xvi) acyl amino selected from $C_{1-6}$ alkoxy-carbonyl amino, mono-$C_{1-6}$ alkylaminocarbonyl amino, $C_{1-6}$ alkylcarbonyl amino and $C_{1-6}$ alkylsulfonyl amino, (xvii) $C_{1-6}$ alkylcarbonyl, (xviii) carboxyl, (xix) $C_{1-6}$ alkoxy-carbonyl, (xx) carbamoyl, (xxi) mono-$C_{1-6}$ alkyl-carbamoyl, (xxii) di-$C_{1-6}$ alkyl-carbamoyl, (xxiii) $C_{6-10}$ aryl-carbamoyl, (xxiv) sulfo, (xxv) $C_{1-6}$ alkyl sulfonyl, (xxvi) $C_{6-10}$ aryl and (xxvii) $C_{6-10}$ aryloxy; the ring a is a 3 to 10 membered cyclic hydrocarbon or 5 to 9 membered heterocycle containing 1 to 4 hetero atoms selected from a nitrogen atom, a sulfur atom and an oxygen atom other than carbon atoms, and the 3 to 10 membered cyclic hydrocarbon or 5 to 9 membered heterocycle is substituted by a halogen atom, $C_{1-6}$ alkyl, $C_{1-6}$ alkoxy or $C_{1-3}$ alkylenedioxy, and adjacent substituents of the ring A may combine with each other and form a 3 to 10 membered cyclic hydrocarbon; and the ring B is a 3 to 10 membered cyclic hydrocarbon or 5 to 9 membered heterocycle containing 1 to 4 hetero atoms selected from a nitrogen atom, a sulfur atom and an oxygen atom other than carbon atoms, and the 3 to 10 membered cyclic hydrocarbon or 5 to 9 membered heterocycle may be substituted by a group selected from the group consisting of (i) a halogen atom, (ii) $C_{1-3}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) optionally halogenated $C_{1-6}$ alkoxy, (x) optionally halogenated $C_{1-6}$ alkylthio, (xi) hydroxy, (xii) amino, (xiii) mono-$C_{1-6}$ alkyl amino, (xiv) di-$C_{1-6}$ alkyl amino, (xv) 5 or 6 membered cyclic amino, (xvi) acyl amino selected from $C_{1-6}$ alkoxy-carbonyl amino, mono-$C_{1-6}$ alkylaminocarbonyl amino, $C_{1-6}$ alkylcarbonyl amino and $C_{1-6}$ alkylsulfonyl amino, (xvii) $C_{1-6}$ alkylcarbonyl., (xviii) carbonyl, (xix) $C_{1-6}$ alkoxy-carbonyl, (xx) carbamoyl, (xxi) mono-$C_{1-6}$ alkyl-carbamoyl, (xxii) di-$C_{1-6}$ alkyl-carbamoyl, (xxiii) $C_{6-10}$ aryl-carbamoyl, (xxiv) sulfo, (xxv) $C_{1-6}$ alkyl sulfonyl, (xxvi) $C_{6-10}$ aryl and (xxvii) $C_{6-10}$ aryloxy, (3) the compound as defined in (1) wherein $R^1$ is a group represented by the formula:

wherein $R^3$ and $R^4$ is the same or different and are independently a hydrogen atom, a hydroxy group which may be substituted, a lower alkyl group which may be substituted, an acyl group, an aryl group which may be substituted or an aralkyl group which may be substituted, or $R^3$ and $R^4$ may combine with an adjacent nitrogen atom and form a nitrogen-containing heterocyclic group which may be substituted, (4) The compound as defined in (3) wherein $R^3$ and $R^4$ is the same or different and are independently a hydrogen atom, a hydroxy group which may be substituted, a lower alkyl group which may be substituted or an acyl group, or $R^3$ and $R^4$ may combine with an adjacent nitrogen atom and form a nitrogen-containing heterocyclic group which may be substituted, (5) The compound as defined in (3) wherein $R^3$ and $R^4$ is the same or different and are independently a hydrogen atom or a lower alkyl group which may be substituted, (6) The compound as defined in (3) wherein $R^3$ is a hydrogen atom or a $C_{1-6}$ alkyl group, and $R^4$ is (i) a hydrogen atom or (ii) a $C_{1-6}$ alkyl group which may be substituted by a group selected from the group consisting of hydroxy, carboxyl, $C_{1-6}$ alkoxy-carbonyl, amino and mono- or di-$C_{1-6}$ alkyl amino, (iii) a $C_{6-14}$ aryl group which may be substituted by $C_{1-6}$ alkoxy or (iv) a $C_{7-16}$ aralkyl group which may be substituted by $C_{1-6}$ alkoxy or $C_{1-6}$ acylamino, or R³ and R⁴ combine with an adjacent nitrogen atom and form a 5 to 8 membered nitrogen-containing heterocyclic group which may be substituted by $C_{7-16}$ aralkyl, (7) The compound as defined in (1) wherein $R^2$ is a hydrogen atom or a lower alkyl group which may be substituted, (8) The compound as defined in (1) wherein $R^2$ is (i) a hydrogen atom or (ii) a $C_{1-6}$ alkyl group which may be substituted by a group selected from the group consisting of hydroxy, carbamoyl optionally having $C_{1-6}$ alkyl and amino optionally having $C_{1-6}$ alkyl, (9) The compound as defined in (1) wherein X is a methyne group which may be substituted,

(10) The compound as defined in (1) wherein X is a methyne group which may be substituted by $C_{1-6}$ alkyl,

(11) The compound as defined in (1) wherein X is N(O)m (m is 0 or 1),

(12) The compound as defined in (1) wherein X is N,

(13) The compound as defined in (1) wherein the ring A is a benzene ring which is substituted by a halogen atom, lower alkyl, lower alkoxy or lower alkylenedioxy,

(14) the compound as defined in (1) wherein the ring A is a $C_{6-12}$ aromatic hydrocarbon ring which is substituted by a group selected from the group consisting of a halogen atom, $C_{1-6}$ alkyl, $C_{1-6}$ alkoxy and $C_{1-3}$ alkylenedioxy,

(15) The compound as defined in (1) wherein the ring B is a benzene ring which may be substituted,

(16) The compound as defined in (1) wherein the ring B is (i) a $C_{6-12}$ aromatic hydrocarbon ring which may be substituted by a group selected from the group consisting of a halogen atom, optionally halogenated $C_{1-6}$ alkyl, optionally halogenated $C_{1-6}$ alkoxy and $C_{1-3}$ alkylenedioxy or, (ii) a 5 to 8 membered heterocycle containing 1 to 3 hetero atoms selected from a nitrogen atom, an oxygen atom and a sulfur atom other than carbon atoms, and the 5 to 8 membered heterocycle may be substituted by $C_{1-6}$ alkyl,

(17) The compound as defined in (1) wherein $R^1$ is a group represented by the formula:

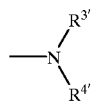

wherein $R^{3'}$ is a hydrogen atom or $C_{1-6}$ alkyl group, and $R^{4'}$ is (i) a hydrogen tom, (ii) a $C_{1-6}$ alkyl group which may be substituted by a group selected from the group consisting of hydroxy, carboxyl, $C_{1-6}$ alkoxy-carbonyl, amino and mono- or di-$C_{1-6}$ alkylamino, (iii) a $C_{6-14}$ aryl group which may be substituted by $C_{1-6}$ alkoxy or (iv) a $C_{7-16}$ aralkyl group which may be substituted by $C_{1-6}$ alkoxy or $C_{1-6}$ acylamino, or $R^{3'}$ and $R^{4'}$ may combine with an adjacent nitrogen atom and form a 5 to 8 membered nitrogen-containing heterocyclic group which may be substituted by $C_{7-16}$ aralkyl;

$R^2$ is (i) a hydrogen atom or (ii) a $C_{1-6}$ alkyl group which may be substituted by a group selected from the group consisting of hydroxy, carbamoyl optionally have $C_{1-6}$ alkyl and amino optionally having $C_{1-6}$ alkyl;

X is a methyne group which may be sustituted by $C_{1-6}$ alkyl or N(O)m (m is 0 or 1);

the ring A is $C_{6-12}$ aromatic hydrocarbon ring which is substituted by a group selected from the group consisting of a halogen atom, $C_{1-6}$ alkyl, $C_{1-6}$ alkoxy and $C_{1-3}$ alkylenedioxy; and the ring B is (i) a $C_{6-12}$ aromatic hydrocarbon ring which may be substituted by a group selected from the group consisting of a halogen atom, optionally halogenated $C_{1-6}$ alkyl, optionally halogenated $C_{1-6}$ alkoxy and $C_{1-3}$ alkylenedioxy or (ii) a 5 to 8 membered heterocycle containing 1 to 3 hetero atoms selected from a nitrogen atom, an oxygen a tom and a sulfur atom other than carbon atoms, and the 5 to 8 membered heterocycle may be substituted by $C_{1-6}$ alkyl,

(18) The company as defined in (1) wherein $R^1$ is a group represented by the formula:

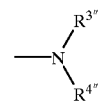

wherein $R^{3''}$ is a hydrogen atom and $R^{4''}$ is a hydrogen atom or $C_{7-16}$ aralkyl group which may be substituted by $C_{1-6}$ alkoxy; $R^2$ is a hydrogen atom or $C_{1-6}$ alkyl group which may be substituted by hydroxy; X is a methyne group or N; the ring A is a $C_{6-12}$ aromatic hydrocarbon ring which is substituted by $C_{1-6}$ alkoxy or $C_{1-3}$ alkylenedioxy; and the ring B is a $C_{6-12}$ aromatic hydrocarbon ring which may be substituted by a group selected from the group consisting of a halogen atom, $C_{1-6}$ alkoxy and $C_{1-3}$ alkylenedioxy,

(19) N-methyl-9-(1,3-benzodioxole-5-yl)-8-hydroxymethyl-naphtho [1,2-d]-1,3-dioxole-6-carboxamide or a salt thereof,

(20) N-methyl-8-(1,3-benzodioxole-5-yl)-8-hydroxymethyl-naphtho [2,3-d]-1,3-benzodioxole-6-carboxamide or a salt thereof,

(21) 9-(1,3-benzodioxole-5-yl)-8-hydroxymethyl-1,3-dioxolo [4,5-f]quinoline-7-carboxamide or a salt thereof,

(22) N-methyl-4-(1,3- benzodioxole-5-yl)-6,7-diethoxy-3-hydroxymethyl-naphthalene-2-carboxamide or a salt thereof,

(23) 9-(4-methoxyphenyl)-N-[(4-methoxyphenyl) menthyl]-1,3-dioxolo [4,5-f]quinoline-7-carboxamide or a salt thereof,

(24) 9-(1,3-benzodioxole-5-yl)-N-[(4-methoxyphenyl) methyl]-1,3-dioxolo [4,5-f]quinoline-7-carboxamide or a salt thereof,

(25) 9-(4-fluorophenyl)-N-[(4-methoxyphenyl)methyl]-1,3-dioxolo[4,5-f]quinoline-7-carboxamide or a salt thereof,

(26) A method for producing a compound represented by the formula:

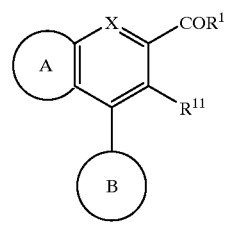

wherein $R^{11}$ is a lower alkyl group which may be substituted and other symbols are same as defined in (1), or a salt thereof which comprises subjecting a compound represented by the formula:

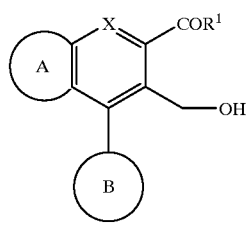

wherein each symbol is a same as defined in (1), or a salt thereof to a functional group-converting reaction or/and a carbon-adding reaction,

(27) A method for producing the compound as defined in (1) or a ester thereof, or a salt thereof which comprises subjecting a compound represented by the formula:

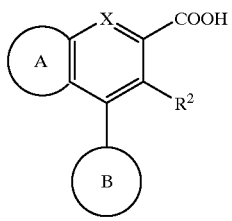

wherein each symbol is same as defined in (1), or a salt thereof to an amidating reaction, and if desired followed by a acylating reaction,

(28) A pharmaceutical composition which comprises the compound as defined in (1) or a salt thereof,

(29) An agent for inducing a cell differentiation or enhancing an action of induction factor of cell differentiation which comprises a compound represented by the formula:

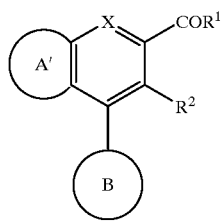

(II)

wherein a ring A' is a homo- or hetero-cycle which may be substituted and other symbols are same as defined in (1),

(30) The agent as defined in (29) wherein the ring A' is (a) 3 to 10 membered cyclic hydrocarbon or (b) a 5 to 9 membered heterocycle containing 1 to 4 hetero atoms selected from a nitrogen atom, a sulfur atom and an oxygen atom other than carbon atoms, and the 3 to 10 membered cyclic hydrocarbon or 5 to 9 membered heterocycle may be substituted by a group selected from the group consisting of (i) a halogen atom, (ii) $C_{1-3}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) optionally halogenated $C_{1-6}$ alkoxy, (x) optionally halogenated $C_{1-6}$ alkylthio, (xi) hydroxy, (xii) amino, (xiii) mono-$C_{1-6}$ alkylamino, (xiv) di-$C_{1-6}$ alkyl amino, (xv) 5 or 6 membered cyclic amino, *xvi) acyl amino selected from $C_{1-6}$ alkoxy-carbonyl amino, mono-$C_{1-6}$ alkylaminocarbonyl amino, $C_{1-6}$ alkylcarbonyl amino and $C_{1-6}$ alkylsulfonyl amino, (xvii) $C_{1-6}$ alkylcarbonyl, (xviii) carboxyl, (xix) $C_{1-6}$ alkoxy-carbonyl, (xx) carbamoyl, (xxi) mono-$C_{1-6}$ alkyl-carbamoly, (xxii) di-$C_{1-6}$ alkyl-carbamoyl, (xxiii) $C_{6-10}$ aryl-carbamoyl, (xxiv) sulfo, (xxv) $C_{1-6}$ alkyl sulfonyl, (xxvi)$c_{6-10}$ aryl and (xxvii) $C_{6-10}$ aryloxy; or adjacent substituents of the ring A' may combine with each other and form (a) a 3 to 10 membered cyclic hydrocarbon, (b) a 3 to 9 membered aromatic heterocycle containing 1 to 4 hetero atoms selected from a nitrogen atom, a sulfur atom and an oxygen atom other than carbon atoms or (c) a 5 to 9 non-aromatic heterocycle containing 1 to 4 hetero atoms selected from a nitrogen atom, a sulfur atom and an oxygen atom other than carbon atoms,

(31) The agent as defined in (28) which is an agent for treating or preventing nerve diseases or bone/joint diseases,

(32) The agent as defined in (31) wherein the nerve disease is a disease based on nerve degeneration in cerebrovascular dementia, senile dementia or Alzheimer's disease; amyotrophic lateral aclerosis; diabetic peripheral neuropathy; or Parkinson disease,

(33) A method for treating or preventing nerve diseases or bone/joint diseases which comprises administering an effective amount of the compound as defined (1) or a salt thereof to mammals,

(34) The method as defined in (33) wherein the nerve disease is a disease based on nerve degeneration in cerebrovascular dementia, senile dementia or Alzheimer's disease; amyotrophic lateral aclerosis; diabetic peripheral neurotrophic lateral aclerosis; diabetic peripheral neuropathy; or Parkinson disease,

(35) Use of the compound as defined in (1) or a salt thereof for preparing an agent for treating or preventing nerve disease or bone/joint disease, and

(36) The use of defined in (35) wherein the nerve disease is a disease based on nerve degeneration in cerebrovascular dementia, senile dementia or Alzheimer's disease; amyotrophic lateral aclerosis; diabetic peripheral neurotrophic laterial aclerosis; diabetic peripheral neuropathy; or Parkinson disease.

DETAILED DESCRIPTION

In the above mentioned formula, the ring A represents a homo- or hetero-cycle which is substituted by a halogen atom, lower alkyl, lower alkoxy or lower alkylenedioxy.

The homo- or hetero-cycle has any (preferably 1 to 5, more preferably 1 to 3) substituents as mentioned above at a position where it can be substituted. When a number of substituents are more than 2, each substituent may be same or different, and adjacent substituents may combine each other and form a ring.

When adjacent substituents of the ring A combine with each other and form a ring, examples of the ring are 3 to 10 membered cyclic hydrocarbon, preferably a 5 to 6 membered cyclic hydrocarbon. Specific examples of the ring are benzene, $C_{3-10}$ cycloalkene (e.g. cyclobutene, cyclopentene, cyclohexene, cycloheptene, cyclooctene, etc.), $C_{3-10}$ cycloalkane (e.g. cyclobutane, cyclopentane, cyclohexane, cycloheptane, cyclooctane, etc.), and so on. Preferable examples of the cycle are a 5 to 6 membered homocycle such as benzene, cyclopentane, cyclohexane, and more prefereable examples are a benzene ring.

When adjacent substituents of the ring A combine with each other and form a condensed ring with the ring A, examples of the condensed ring are naphtharene, and so on.

In the above mentioned formula, the homocycle represented by the ring A means a cyclic hydrocarbon consisting of carbon atoms. Examples of the cyclic hydrocarbon are a 3 to 10 membered cyclic hydrocarbon, preferably a 5 to 6 membered cyclic hydrocarbon. Specific examples of the homocycle are benzene, $C_{3-10}$ cycloalkene (e.g cyclobutene, cyclopentene, cyclohexene, cycloheptene, cyclooctene, etc.), $C_{3-10}$ cycloalkane (e.g. cyclobutane, cyclopentane, cyclohexane, cycloheptane, cyclooctane, etc.) and so on. Preferable examples are 5 to 6 membered homocycle such as benzene, cyclopentane, cyclohexane, and more preferable examples are a benzene ring and so on.

In the above mentioned formula, examples of the heterocycle represented by the ring A are an aromatic heterocycle or non-aromatic heterocycle containing more than 1 (e.g., 1 to 4, preferably 1 to 3) and one or two kinds of hetero atoms selected from a nitrogen atom, a sulfur atom and an oxygen atom other than carbon atoms, and so on.

Examples of the aromatic heterocycle are a 5 to 6 membered aromatic heterocycle containing 1 to 3 hetero atoms selected by a nitrogen atom, an oxygen atom and a sulfur atom other than carbon atoms, such a a pyridine, pyrazine, pyrimidine, pyridazine, pyrole, imidazole, pyrazole, triazole, thiophene, furan, thiazole, isothiazole, oxazole and isoxazole ring, and so on. More preferable examples are a 6 membered nitrogen-containing heterocycle such as a pyridine, pyrazine, thiophene, pyrole, thiazole ring and so on. Particularly, a 6-membered nitrogen-containing heterocycle containing 1 or 2 nitrogen atoms other than carbon atoms (e.g. pyridine, pyrazine) is preferred.

Examples of the non-aromatic heterocycle are a 5 to 9 membered non-aromatic heterocycle, preferably a 5 to 6 membered non-aromatic heterocyle, containing 1 to 3 hetero atoms selected from a nitrogen atom, an oxygen atom and a sulfur atom other than carbon atoms, and so on.

Specific examples of the non-aromatic heterocycle are a tetrahydropirdine, dihydropyridine, tetrahydropyrazine, tetrahydropyrimidine, tetrahydropyridazine, dihydropyrane, dihydropyrole, dihydroimidazole, dihydropyrazole, dihydrothiophene, dihydrofurane, dihydrothiazole, dihydroisothiazole, dihydrooxazole, dihydroisoxazole, piperidine, piperazine, hexahydropyrimidine, hexahydropyridazine, tetrahydropyrane, morphorine, pyrolodine, imidazolidide, pyrazoridine, tetrahydrorthiophene, tetrahydrofurane, tetrahydrothiazole, tetrahydroisothiazole, tetrahydrooxazole, tetrahydroisoxazole ring and so on. Preferable examples are a 6 membered non-aromatic heterocycle containing 1 to 2 nitrogen atoms such as a tetrahydropyridine, tetrahydropyrimidine, tetrahydropyridazine, pyperidine, pyperazine ring, and more preferably examples are a pyperazine ring and so on.

In the homo- or hetero-cycle which is substituted by a halogen atom, lower alkyl, lower alkoxy or lower alkylenedioxy represented by the ring A,
(i) examples of the halogen atom are fluorine, chlorine, bromine and iodine
(ii) examples of the lower alkyl are a linear or branched $C_{1-6}$ alkyl such as methyl, ethyl, propyl, isopropyl, buthyl, isobuthyl, sec-buthyl, tert-buthyl, penthyl, hexyl and so on, preferably methyl,
(iii) examples of the lower alkoxy are a linear or branched $C_{1-6}$ alkoxy such as methoxy, ethoxy, propoxy, isopropoxy, buthoxy, isobuthoxy, sec-buthoxy, tert-buthoxy and so on, preferably methoxy,
(iv) examples of the lower alkylenedioxy are a $C_{1-3}$ alkylenedioxy such as methylendioxy, ethylendioxy, propylenedioxy and so on, preferably, ethylenedioxy.

Preferable examples of the ring A are a homocycle (preferably, a $C_{6-12}$ aromatic hydrocarbon ring) which is substituted by a halogen atom, lower alkyl ( e.g. $C_{1-6}$ alkyl), lower alkoxy (e.g. $C_{1-6}$ alkoxy) or lower alkylenedioxy (e.g. $C_{1-3}$ alkylenedioxy), and more preferable examples are a benzene ring which is substituted by a halogen atom, $C_{1-6}$ alkyl, $C_{1-6}$ alkoxy or $C_{1-6}$ alkylenedioxy.

In the above mentioned formula, the ring A' represents a homo- or hetero-cycle which may be substituted.

In the above mentioned formula, examples of the homocycle or heterocycle represented by the ring A' are the homo- or hetero-cycle of the "homo- or hetero-cycle which is substituted by a halogen atom, lower alkyl, lower alkoxy or lower alkylenedioxy" represented by the ring A.

The homo- or hetero-cycle has any (preferably 1 to 5, more preferably 1 to 3) substiuents at a position where can be substituted. When a number of substituents are more than 2, each substituent may be same or different, and adjacent substituents may combine with each other and form a ring.

When adjacent substituents of the ring A combine with each other and form a ring, examples of the ring are
(i) a 3 to 10 membered cyclic hydrocarbon, preferably a 5 to 6 membered cyclic hydrocarbon,
(ii) a 3 to 9 membered aromatic heterocycle, preferably a 5 or 6 membered aromatic heterocycle containing more than 1 (e.g., 1 to 4, preferably 1 to 3) and one or two kinds of hetero atoms selected from a nitrogen atom, an oxygen atom and a sulfur atom other than carbon atoms, or
(iii) a 5 to 9 membered non-aromatich heterocycle, preferably a 5 or 6 membered non-aromatich heterocycle, containing more than 1 (e.g., 1 to 4, preferably 1 to 3) and one or two kinds of hetero atoms selected from a nitrogen atom, an oxygen atom and a sulfur atom other than carbon atoms and so on.

Specific examples of the 3 to 10 membered cyclic hydrocarbon in the above (i) are benzene, $C_{3-10}$ cycloalkene (e.g. cyclobutene, cyclopentene, cyclohexane, cycloheptene, cyclootene, etc.), $C_{3-10}$ cycloalkane (e.g. cyclobutane, cyclopetane, cyclohexane, cycloheptane, cyclootane, etc.), and so on. Preferable examples are 5 to 6 homocycle such as benzene, cyclopentane, an cyclohexane, and more preferable examples area benzene ring, and so on.

Examples of the aromatic heterocycle of the above (ii) are a 5 to 9 membered, preferably a 5 to 6 membered, aromatic heterocycle containing 1 to 3 hetero atoms selected from a nitrogen atom, an oxygen atom and a sulfur atom other than carbon atoms such as a pyridine, pyrazine, pyrimidine, pyridazine, pyrole, imidazole, pyrazole, triazole, thiophene, furan, thiazole, isothiazole, oxazole and isoxazole ring, and so on.

Examples of the non-aromatic heterocycle of the above (iii) area a 5 to 9 membered, preferably a 5 to 6 membered, non-aromatic heterocycle containing 1 to 3 hetero atoms selected from a nitrogen atom, an oxygen atom and a sulfur atom other than carbon atoms and so on. Specific examples of the non-aromatic heterocycle are a tetrahydropiridine, dihydropyridine, tetrahydropyradine, tetrahydropyrimidine, tetrahydropyridazine, dihydropyrane, dihydropyrole, dihydromidazole, dihydropyrazole, dihydrothiophene, dihydrofurane, dihydrothiazole, dihydroisothiazole, dihydrooxazole, dihydrioisoxanzone, piperidine, piperazine, hezahydropyrimidine, hexahydropyridazine, tetrahydropyrane, morphorine, pyrrolidine, imidazolidide, pyrazoridine, tetrahydrorthiophene, tetrahydrofurane, tetrahydrothiazole, tetrahydroisothiazole, tetrahydrooxazole, tetrahydroisoxazole ring, and so on.

When adjacent substituents of the ring A' combine with each other and form a condensed ring with the ring A', examples of the condensed ring are naphtharene, and so on.

In the above mentioned formula, examples of the substituents of the homo- or hetero-cycle represented by the ring A' are (i) a halogen atom (e.g. fluorine, chlorine, bromine, iodine), (ii) lower alkylendedioxy (e.g. $C_{1-3}$ alkylenedioxy such as methylenedioxy, ethylenedioxy), (iii) nitro, (iv) cyano, (v) optionally halogenated lower alkyl, (vi) optionally halogenated lower alkenyl, (vii) optionally halogenated lower alkynyl, (viii) lower cycloalkyl (e.g. $C_{3-6}$ cycloalkyl such as cyclopropyl, cyclobuthyl, cyclopenthyl, cyclohexyl), (ix) optionally halogenated lower alkoxy, (x) optionally halogenated lower alkylthio, (xi) hydroxy, (xii) amino, (xiii) mono-lower alkylamino (e.g. mono-$C_{1-6}$ alkylamino such as methylamino, ethylamino, propylamino, isopropylamino, buthylamino), (xiv) di-lower alkylamino (e.g. di-$C_{1-6}$ alkyl amino such as dimethylamino, diethylamino, dipropylamino, dibuthylamino), (xv) 5 or 6 membered cyclic amino (e.g. morpholino, pyperadine-1-yl, pyperidino, pyroridine-1yl, (xvi) acyl amino (xvii) lower alkyl-carbonyl (e.g. $C_{1-6}$ alkyl-carbonyl such as acetyl, propyoyl), (Xviii) carboxyl, (xix) lower alkoxy-carbonyl (e.g. $C_{1-6}$ alkoxy-carbonyl such as methoxycarbonyl, ethoxycarbonyl, propxycarbonyl, butoxycarbonyl), (xx) carbamoyl, (xxi) mono-lower alkyl-carbamoyl (e.g. mono-$C_{1-6}$ alkyl-carbamoyl such as methylcarbamoyl, ethylcarbamoyl), (xxii) di-lower alkyl-carbamoyl (e.g.di-$C_{1-6}$ alkyl-carbamoyl such as dimethylcarbamoyl, diethylcarbamoyl), (xxiii) aryl-carbamoyl (e.g. $C_{6-10}$ aryl-carbamoyl such as phenylcarbamoyl, naphtylcarbamoyl), (xxiv) sulfo, (xxv) lower alkyl sulfonyl (e.g. $C_{1-6}$ alkyl sulfonyl such as methylsulfonyl, ethylsulfonyl), (xxvi) aryl (e.g. $C_{6-10}$ aryl such as phenyl, naphthyl) or (xxvii) aryloxy (e.g. $C_{6-10}$ aryloxy such as phenyloxy, naphthyloxy).

Examples of the optionally halogenated lower alkyl are lower alkyl (e.g. $C_{1-6}$ alkyl such a methyl, ethyl, propyl, isopropyl, buthyl, isobuthyl, sec-buthyl, tert-buthyl, penthyl, hexyl) optionally having 1 to 3 halogen atoms (e.g. fluorine, chlorine, bromine, iodine) and so on. Specific examples of the optionally halogenated lower alkyl are methyl, chloromethyl, difluoromethyl, trichloromethyl, trifluoromethyl, ethyl, 2-bromoethyl, 2,2,2,-trifluoroethyl, propyl, 3,3,3,-trifluoropropyl, isopropyl, buthyl, 4,4,4-trifluorobuthyl, isobuthyl, sec-buthyl, tert-buthyl, penthyl, isopenthyl, neopenthyl, 5,5,5- trifluropenthyl, hexyl, 6,6,6-trifluorohexyl and so on.

Examples of the optionally halogented lower alkenyl are lower alkenyl (e.g. $C_{2-6}$ alkenyl such as vinyl, propenyl, isopropenyl, 2-butene-1-yl, 4-penthene-1-yl, 5-hexene-1-yl) optionally having 1 to 3 halogen atoms (e.g. fluorine, chlorine, bromine, iodine) and so on.

Examples of the optionally halogenated lower alkynyl are lower alkynly (e.g. $C_{2-6}$ alkynly such as 2-butyne1-yl, 4-pentyne-1-yl, 5-hexyne-1-yl) optionally having 1 to 3 halogen atoms (e.g. fluorine, chlorine, bromine, iodine) and so on.

Examples of the optionally halogenated lower alkoxy are lower alkoxy (e.g. $C_{1-6}$ alkoxy such as methoxy, ethoxy, propoxy, isopropoxy, n-buthoxy, isobuthoxy, sec-buthoxy, tert-cuthoxy) optionally having 1 to 3 halogen atoms (e.g. fluorine, chlorine, bromine, iodine) and so on. Specific examples of the optionally halogenated lower alkoxy are methoxy, difluoromethoxy, tirfluoromethoxy, ethoxy, 2,2,2-trifluorobuthoxy, n-propoxy, isopropoxy, n-butoxy, 4,4,4-trifluorobuthoxy, isobuthoxy, sec-buthoxy, penthyloxy, hexyloxy and so on.

Examples of the optionally halogenated lower alkylthio are lower alkylthio (e.g. $C_{1-6}$ alkylthio such as methylthio, ethylthio, n-propylthio, isopropylthio, n-buthylthio, isobuthylthio, sec-buthylthio, tert-buthylthio) optionally having 1 to 3 halogen atoms (e.g. fluorine, chlorine, bromine, iodine) and so on. Specific examples of the optionally halogenated lower alkylthio are methylthio, difluromethylthio, trifluoromethylthio, ethylthio, propylthio, isopropylthio, buthylthio, 4,4,4-trifluorobuthylthio, penthylthio, hexylthio and so on.

Examples of the acylamino are —NHCOOR$^5$, —NHCOHNR$^5$, —NHCOR$^5$ or —NHSO$_2$R$^5$ wherin R$^5$ is a hydrocarbon group.

Examples of the hydrocarbon group represented by R$^5$ is a group formed by removing one hydrogen atom from the hydrocarbon compound and so on. Specific examples are a linear or cyclic hydrocarbon group such as an alkyl group, an alkenyl group, an alkynyl group a cycloalkyl group, an aryl group an ararkyl group and so on. Of them, a $C_{1-16}$ chain ( linear or branched) or cyclic hydrocarbon group, and more preferable examples are (a) alkyl group, preferably lower alkyl group (e.g. $C_{1-6}$ alkyl group such as methyl, ethyl, propyl, isopropyl, buthyl, isobuthyl, sec-buthyl, tert-buthyl, penthyl, hexyl), (b) alkenyl group, preferably lower alkenyl group (e.g. $C_{2-6}$ alkenyl such as vinyl, allyl, isopropenyl, butenyl, isobutenyl, sec-butenyl), (c) alkynly gorup, preferably lower alkynly (e.g. $C_{2-6}$ alkynly such as propalgyl, ethynyl, butynyl, 1-hexynyl), (d) cycloalkyl group, preferably lower cycloalkyl (e.g. $C_{3-6}$ cycloalkyl such as cyclopropyl, cyclobuthyl, cyclopenthyl, cyclohexyl which may condense with a benzene ring optionally having 1 to 3 lowe alkoxys (e.g. $C_{1-6}$ alkoxy such as methoxy)).

(e) an aryl group (e.g. $C_{6-14}$ aryl group such as phenyl, tryl, xylyl, biphenyl, 1-naphthyl, 2-naphthyl, 2-indenyl, 2-anthryl, 1-antryl, 2-antryl, 3-antryl, 1-phenantryl, 2-phenantryl, 3-phenantryl, 4-phenantryl or 9-phenantryl, preferably phenyl), (f) an ararkly group (e.g. $C_{7-16}$ aralkyl group such as benzyl, phenetyl, diphenylmethyl, 1-napthylmethyl, 2-naphtylmethyl, 2phenylethyl, 2-diphenylethyl, 1-phenylpropyl, 2-phenylpropyl, 3-phenylpropyl, 4-phenylbuthyl or 5phenylpenthyl, preferably benzyl).

In the above mentioned formula, preferable examples of the substituents of the "homo- or hetero-cycle represented by the A' are a halogen atom, an optionally halogenated lower alkyl group (preferably methyl), an optionally halogenated lower alkoxy group (preferably methoxy), a lower alkylenedioxy group (preferably methylendedioxy) or a hydroxy group, and more preferable examples are a lower alkoxy (preferably methoxy), a lower alkylenedixoy group (preferably methylenedioxy) and so on.

Preferable examples of the ring A' are a homocycle which may be substituted, and more preferable examples are a benzene ring which may be substituted and so on. Specifically, the above mentioned preferable examples of the ring A are also used as preferable examples of the ring A.

In the above mentioned formula, Examples of the homocycle and heterocycle represented by the ring B are the homocycle and heterocycle of the "homo- or hetero-cycle which may be substituted by a halogen atom, a lower alkyl group, a lower alkoxy group or a lower alkylenedioxy group" represented by the ring A.

In the above mentioned formula, Examples of the substituents of the "homo- or hetero-cycle which may be substituted " represented by the ring B are the same those of the substituents of the "homo- or hetero-cycle which may be substituted" represented by the ring A'.

Preferable examples of the substituents of the "homo- or hetero-cycle which may be substituted" represented by the ring B are (i) a halogen atom (e.g. fluorine, chlorine, bromine, iodine, etc.), (ii) a lower alkylenedioxy group (e.g. $C_{1-3}$ alkylenedioxy such s methylenedioxy and ethylenedioxy, etc), (iii) an optionally halogenated lower alkyl group (e.g. optionally halogenated $C_{1-6}$ alkyl such as methyl, chloromethyl, difluoromethyl, trichloromethyl, trifluoromethyl, ethyl, 2-bbromoethyl, 2,2,2-trifluroethyl, propyl, 3,3,3-triflluropropyl, isopropyl, buthyl, 4,4,4-triflurobuthyl, isobuthyl, sec-buthyl, tert-buthyl, penthyl, isopenthyl, neopenthyl, 5,5,5trifluoropenthyl, hexyl, 6,6,6-trifluorhexyl and so on, preferably methyl and trifluoromethyl), (iv) an optionally halogenated lower alkoxy (e.g. Optionally halogenated $C_{1-6}$ alkoxy such as methoxy, difluoromethoxy, trifluromethoxy, ethoxy, 2,2,2-trifluoroethoxy, n-propoxy, isopropoxy, n-buthoxy, 4,4,4-triflurobutoxy, isobuthoxy, sec-buthoxy, penthyloxy, hexyloxy and so on, preferably methoxy), and so on.

Preferable examples of the ring B are a benzene ring which may be substituted. More preferable examples are (i) a $C_{6-12}$ aromatic hydrocarbon ring (preferably, a benzene ring) which may be substituted by a group selected from the group consisting of a halogen atom, optionally halogenated $C_{1-6}$ alkyl, optionally halogenated $C_{1-6}$ alkoxy and $C_{1-3}$ alkylenedioxy or (ii) a 5 to 8 membered heterocycle containing 1 to 3 hetero atoms selected from a nitrogen atom, an oxygen atom and a sulfur atom other than carbon atoms and the 5 to 8 membered heterocycle may be substituted by $C_{1-6}$ alkyl, and so on.

In the above mentioned formula, X represents a methyne group which may be substituted or N(O)m (M is 0 or 1).

In the above mentioned formula examples of the "methyne group which may be substituted " represented by X are $CR^6$ wherein $R^6$ is a hydrogen atom, (e.g. fluorine, chlorine, bromine, iodoine), a hydrocarbon group which may be substituted or a hydroxy group which may be substituted, and so on.

Examples of the hydrocarbon group represented by $R^6$ are the hydrocarbon group represented by the above mentioned $R^5$, and more preferable examples are a lower alkyl group such as methyl, ethyl, propyl, isopropyl, buthyl, isobuthyl, sec-buthyl, penthyl, hexyl and so on.

Examples of the substituents of the hydrocarbon group represented by $R^6$ are the substituents of the homo- or hetero-cycle represented by the above mentioned ring A', and so on.

The hydroxy group which may be substituted represented by $R^6$ is (i) a hydroxy group or (ii) a hydroxy group having one group such as the above mentioned hydrocarbon group which may have substituents instead of a hydrogen atom of the hydroxy group. Specifically, the above mentioned —$OR^{6"}$, etc. are used, and preferable examples are a hydroxy group or a hydroxy group having one group such as a lower alkyl group which may be substituted. Examples of the lower alkyl group are a linear or branched $C_{1-6}$ alkyl group (e.g. methyl, ethyl, propyl, isopropyl, buthyl, isobuthyl, sec-buthyl, tert-buthyl, penthyl, hexyl, etc.), and so on. Examples of the substituents of the lower alkyl group are the substituents of the homo- or hetero-cycle represented by the above mentioned ring A'.

Preferable examples of X are a methyne group which may be substituted by $C_{1-6}$ alkyl or N, and more preferable examples are CH, C—$CH_3$, N and so on.

In the above mentioned formula, $R^1$ represents an amino group which may be substituted. Examples of the substituents of the amino group are a hydrocarbon group which may be substituted, a hydroxy group which may be substituted, an acyl group and so on. And, the amino group which may be substituted includes a nitrogen-containing heterocyclic group which has a binding site on a ring-component nitrogen atom, and the nitrogen-containing heterocyclic group may have substituents.

Examples of the hydrocarbon group of the "hydrocarbon group which may be substituted" are the hydrocarbon goroup of the "homo- or hetero-cycle which may be substituted" represented by the above mentioned $R^5$ and so on.

Exampales of the substituents of the hydrocarbon group are the substituents of the homo- or hetero-cycle represented by the above mentioned ring A'.

Examples of the hydroxy group which may be substituted are the "hydroxy group which may be substituted" represented by the above mentioned $R^6$, and so on.

Examples of the acyl group are —(C=O)—$R^7$, —$SO_2$—$R^7$, —SO—$R^7$, —(C=O)$NR^8R^7$, —(C=O)O—$R^7$, —(C=S)O—$R^7$ or —(C=S)$NR^8R^7$ wherein $R^7$ is a hydrogen atom or a hydrocarbon group which may be substituted and $R^8$ is a hydrogen atom or a lower alkyl group (e.g. a $C_{1-6}$ alkyl group such as methyl, ethyl, propyl, isopropyl, buthyl, isobuthyl, tert-buthyl, penthyl, hexyl and so on, preferably a $C_{1-3}$ alkyl such as methyl, ethyl, propyl, isopropyl and so on). Of them, —(C=O)—$R^7$, —$SO_2$—$R^7$, —SO—$R^7$, —(C=O)$NR^8R^7$, —(C=O)O—$R^7$ are preferred, and —(C=O)—$R^7$ is more preferred.

Examples of the hydrocarbon group represented by $R^7$ is a group formed by removing one hydrogen from atom from the hydrocarbon compound. Specific examples are chained (linear or branched) or cyclic hydrocarbon group such as an alkyl group, an alkenyl group, an alkynyl group, a cycloalkyl group, an aryl group, an ararkyl group and so on. Specifically, the hydrocarbon group represented by $R^5$, etc. are used. Of them, a $C_{1-16}$ linear or cyclic hydrocarbon group, etc. are preferred and a lower ($C_{1-6}$) alkyl group, etc. are more preferred.

Examples of the substituents of the hydrocarbon group represented by $R^7$ are the substituents of the "homo- or hetero-cycle which may be substituted" represented by the ring A', and so on.

Examples of the nitrogen-containing heterocyclic group represented by $R^1$, are a group formed by removing a hydrogen atom from a nitrogen atom of a 5 to 9 membered nitrogen-containing heterocyclic which may have 1 to 3 hetero atoms selected from a nitrogen atom, an oxygen atom and a sulfur atom other than carbon atoms and one nitrogen atom, and so on.

Specifically,

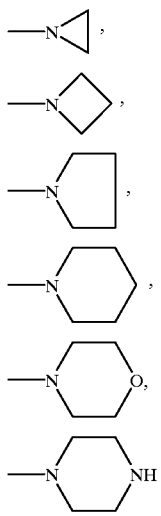

are preferably used.

Examples of the substituents of the nitrogen-containing heterocyclic group are the substituents of the homo- or hetero-cycle which may be substituted represented by the above mentioned ring A'.

Preferable examples of the amino group which may be substituted represented by $R^1$ are a group represented by the formula:

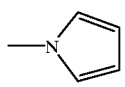

wherein $R^3$ and $R^4$ is the same or different and are independently a hydrogen atom, a hydroxy group which may be substituted, a lower alkyl group which may be substituted, or acyl group, an aryl group which may be substituted or an aralkyl group which may be substituted, or $R^3$ and $R^4$ may combine with an adjacent nitrogen atom and form a nitrogen-containing heterocyclic group which may be substituted, and so on. Of them, a group wherein $R^3$ and $R^4$ is the same or different and are independently a hydrogen atom, a hydroxy group which may be substituted, a lower alkyl group which may be substituted or an acyl group, or $R^3$ and $R^4$ may combine with an adjacent nitrogen atom and form a nitrogen-containing heterocyclic group which may be substituted, etc. are preferred.

Examples of the hydroxy group which may be substituted represented by $R^3$ and $R^4$ are the hydroxy group which may be substituted represented by $R^6$, etc.

Examples of the lower alkyl group represented by $R^3$ and $R^4$ are a linear or branched $C_{1-6}$ alkyl group such as methyl, ethyl, propyl, isopropyl, buthyl, isobuthyl, sec-buthyl, tert-buthyl, penthyl and hexyl. Examples of the substituents of the lower alkyl group are the substituents of the homo- or hetero-cycle which may be substituted represented by the above mentioned ring A'.

Examples of the acyl group represented by $R^3$ and $R^4$ are the above mentioned acyl group which is the substituents of the amino group which may be substituted represented by $R^1$.

Examples of the nitrogen-containing heterocyclic group formed by $R^3$, $R^4$ and the adjacent nitrogen atom are a group formed by removing a hydrogen atom from a nitrogen atom of a 5 to 9 membered nitrogen-containing heterocyclic which may have 1 to 3 hetero atoms selected from a nitrogen atom, an oxygen atom and a sulfur atom other than carbon atoms and one nitrogen atom, and so on.

Specifically,

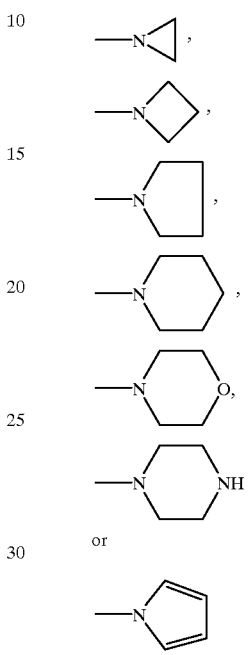

are preferably used.

Examples of the substituents of the nitrogen-containing heterocyclic group are the substituents of the "homo- or hetero-cycle which may be substituted" represented by the above mentioned ring A', and so on.

Preferable examples of $R^3$ to $R^4$ are the same or different and are independently a hydrogen atom or a lower alkyl group which may be substituted, and so on.

Particularly, $R^3$ is a hydrogen atom or a $C_{1-6}$ alkyl group, and $R^4$ is (i) a hydrogen atom or (ii) a $C_{1-6}$ alkyl group which may be substituted by a group selected from the group consisting of hydroxy, carboxyl, $C_{1-6}$ alkoxy-carbonyl, amino and mono- or di-$C_{1-6}$ alkyl amino, (iii) a $C_{6-14}$ aryl group which may be substituted by $C_{1-6}$ alkoxy or (iv) a $C_{7-16}$ aralkyl group which may be substituted by $C_{1-6}$ alkoxy or $C_{1-6}$ acylamino, or $R^3$ and $R^4$ may combine with an adjacent nitrogen atom and form a 5 to 8 membered nitrogen-containing heterocyclic group which may be substituted by $C_{7-16}$ aralkyl (e.g., benzyl).

In the above mentioned formula, $R^2$ represents a hydrogen atom or a lower alkyl group which may be substituted.

Examples of the lower alkyl group represented by $R^2$ are a linear or branched $C_{1-6}$ alkyl group such as methyl, ethyl, propyl, isopropyl, buthyl, isobuthyl, sec-buthyl, tert-buthyl, penthyl and hexyl. Examples of the substituents of the lower alkyl group represented by $R^2$ are the substituents of the "homo- or hetero-cycle which may have substituents" represented by the above mentioned ring A', and a hydroxy group is particularly preferred.

Preferable examples of $R^2$ are (i) a hydrogen atom or (ii) a $C_{1-6}$ alkyl group which may be substituted by a group selected from the group consisting of hydroxy, carbamoyl optionally having $C_{1-6}$ alkyl and amino optionally having $C_{1-6}$ alkyl, and more preferable examples are a hydrogen atom, a $C_{1-6}$ alkyl group which may be substituted by hydroxy, and so on.

Preferable examples of the compound (I) or (II) are compounds wherein $R^1$ is a group represented by the formula:

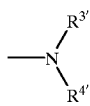

wherein $R^3$ is a hydrogen atom or a $C_{1-6}$ alkyl group, and $R^{4'}$ is (i) a hydrogen atom, (ii) a $C_{1-6}$ alkyl group which may be substituted by a group selected from the group consisting of hydroxy, carboxyl, $C_{1-6}$ alkoxy-carbonyl, amino and mono- or di-$C_{1-6}$ alkylamino, (iii) a $C_{6-14}$ aryl (e.g., phenyl) group which may be substituted by $C_{1-6}$ alkoxy or (iv) a $C_{7-16}$ aralkyl group (e.g., benzyl) which may be substituted by $C_{1-6}$ alkoxy or $C_{1-6}$ acylamino, or $R^{3'}$ and $R^{4'}$ may combine with an adjacent nitrogen atom and form a 5 to 8 membered nitrogen-containing heterocyclic group which may be substituted by $C_{7-16}$ aralkyl (e.g., benzyl); $R^2$ is (i) a hydrogen atom or (ii) a $C_{1-6}$ alkyl group which may be substituted selected from the group consisting of hydroxy, carbamoyl optionally having $C_{1-6}$ alkyl and amino optionally having $C_{1-6}$ alkyl; X is a methyne group which may be substituted by $C_{1-6}$ alkyl or $N(O)m$ (m is 0 or 1); the ring A is a $C_{6-12}$ aromatic hydrocarbon ring (e.g., a benzene ring) which is substituted by a group selected from the group consisting of a halogen atom, $C_{1-6}$ alkyl, $C_{1-6}$ alkoxy and $C_{1-3}$ alkylenedioxy; and the ring B is (i) a $C_{6-12}$ aromatic hydrocarbon ring (e.g., a benzyne ring) which may be substituted by a group selected from the group consisting of a halogen atom, optionally halogenated $C_{1-6}$ alkyl, optionally halogenated $C_{1-6}$ alkoxy and $C_{1-3}$ alkylenedioxy or (ii) a 5 to 8 membered heterocycle containing 1 to 3 hetero atoms selected from a nitrogen atom, an oxygen atom and a sulfur atom other than carbon atoms and the a 5 to 8 membered heterocycle may be substituted by $C_{1-6}$ alkyl, and so on.

More preferable examples of the compound (I) or (II) are compounds wherein $R^1$ is a group represented by the formula:

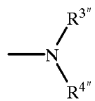

wherein $R^{3''}$ is a hydrogen atom and $R^{4''}$ is a hydrogen atom or a $C_{7-16}$ aralkyl group (e.g., a benzyl group) which may be substituted by $C_{1-6}$ alkoxy; $R^2$ is a hydrogen atom or a $C_{1-6}$ alkyl group which may be substituted by hydroxy; X is a methyne group or N; the ring A is a $C_{6-12}$ aromatic hydrocarbon ring (e.g., a benzene ring) which is substituted by $C_{1-6}$ alkoxy or $C_{1-3}$ alkylenedioxy; and the ring B is a $C_{6-12}$ aromatic hydrocarbon ring (e.g., a benzene ring) which may be substituted by a group selected from the group consisting of a halogen atom, $C_{1-6}$ alkoxy and $C_{1-3}$ alkylenedioxy, and so on.

More specifically, preferable examples of the compound (I) or (II) are

N-methyl-9-(1,3-benzodioxole-5-yl)-8-hydroxymethyl-naphtho[1,2-d]-1,3-dioxole-7-carboxamide or a salt thereof, N-methyl-8-(1,3-benzodioxole-5-yl)-7-hydroxymethyl-naphtho[2,3-d]-1,3-dioxole-6-carboxamide or a salt thereof, 9-(1,3-benzodioxole-5-yl)-8-hydroxymethyl-1,3-dioxolo [4,5-f]quinoline-7-carboxamide or a salt thereof, N-methyl-4-(1,3-benzodioxole-5-yl)-6,7-diethoxy-3-hydroxymethyl-napthalene-2-carboxamide or a salt thereof, 9-(4-methoxyphenyl)-N-[(4-methoxyphenyl)methyl]-1,3-dioxolo[4,5-f]quinoline-7-carboxamide or a salt thereof, 9-(1,3-benzodioxole-5-yl)-N-[(4-methoxyphenyl)methyl]-1,3-dioxolo [4,5-f]quinoline-7-carboxamide or a salt thereof, 9-(4-fluorophenyl)-N-[(4-methoxyphenyl)methyl]-1,3-dioxolo [4,5-f]quinoline-7-carboxamide or a salt thereof, and so on.

The compound (I) or compound (II) of the present invention or a salt thereof (hereinafter simply referred to as the compound (I) or the compound (II)) can be produced by a variety of methods; representative examples are shown in schemes 1 and 2 below.

Note that in the following description of production methods, the starting material compound and reaction product may form a salt that does not hamper the reaction.

Examples of the "salt that does not hamper the reaction" are the same salts as those of compound (I) or those of compound (II) below.

Of the compounds included in the compound (I) or the compound (II) wherein X is $N(O)m$ (m represents 0 to 1), those wherein m is 1 or a salt thereof can be produced by a known chemical oxidizing reaction [e.g., Chemistry of the Heterocyclic N-Oxide, pp. 22–60 (1971), Academic Press, London & New York, or G. Jones ed., "Quinolines part 1," John Wiley & Sons, Chapter 1, pp. 61–62 (1977)] or a modification thereof at an appropriate stage where the compound occurs as a compound wherein m is 0 or a salt thereof or as a production intermediate thereof.

Of the compounds included in the compound (I) or the compound (II), a compound wherein $R^2$ is a hydrogen atom and X is a methine group which may be substituted, namely a compound (XI), or compound (XI'), can, for example, be produced by the method shown by scheme 1 below.

(Scheme 1)

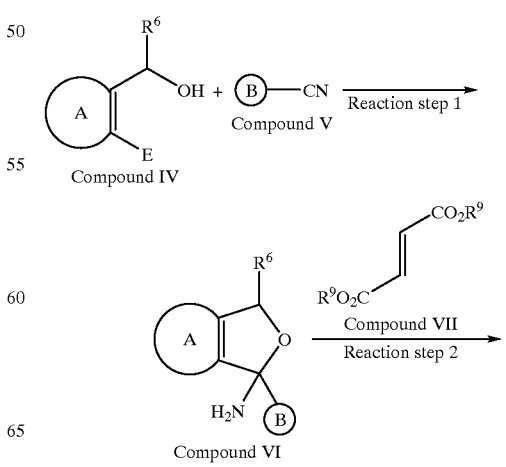

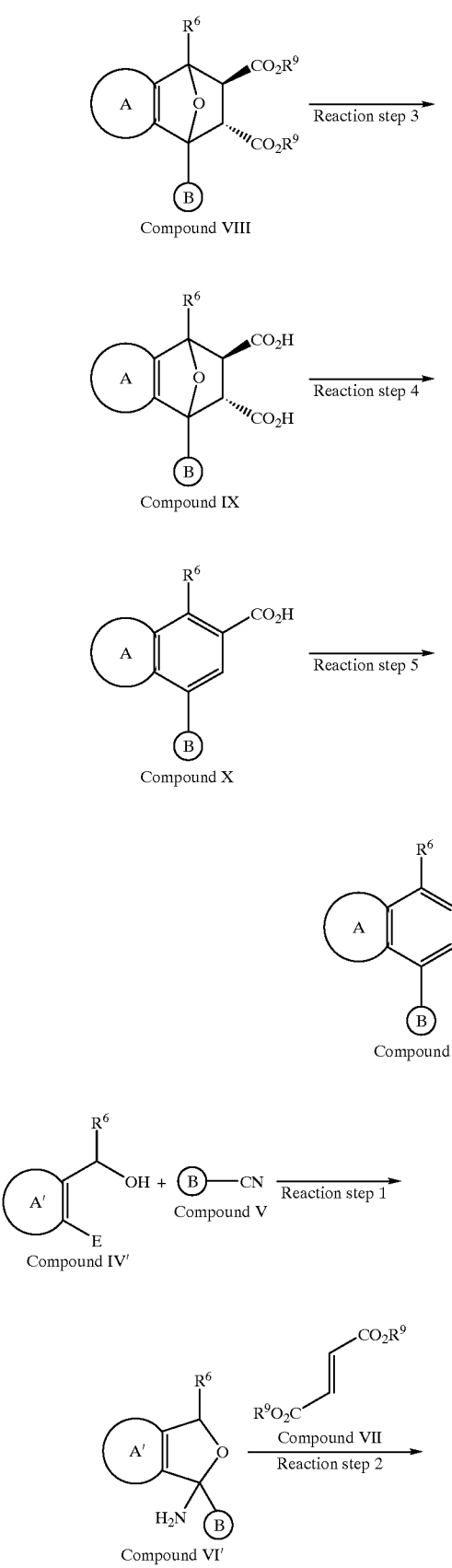
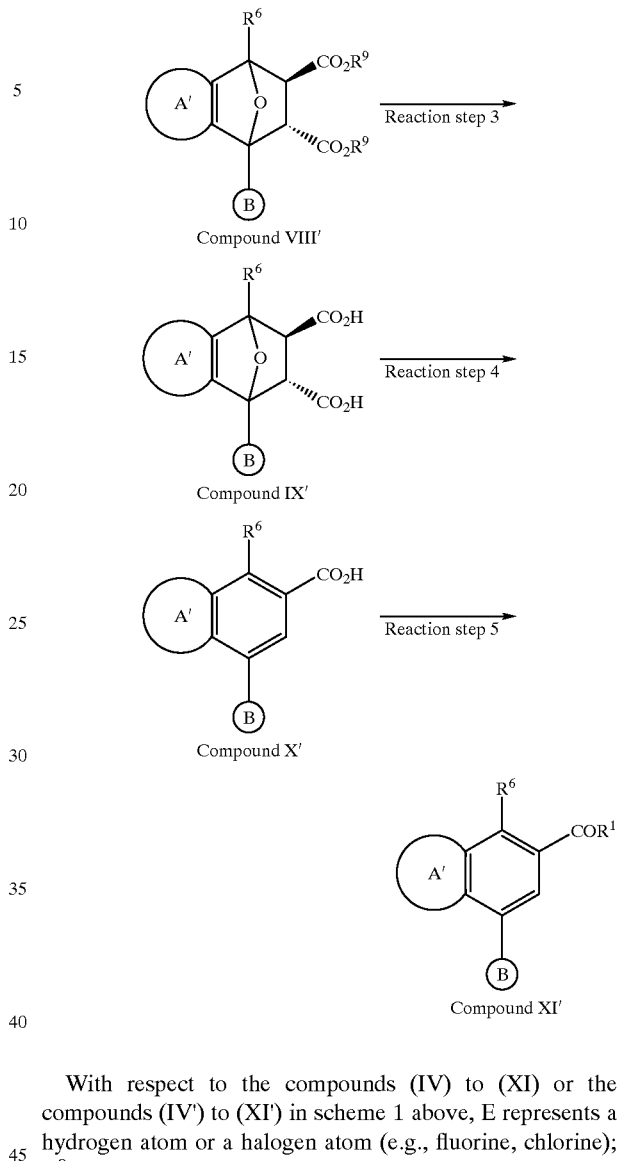

With respect to the compounds (IV) to (XI) or the compounds (IV') to (XI') in scheme 1 above, E represents a hydrogen atom or a halogen atom (e.g., fluorine, chlorine); $R^9$ represents a lower alkyl group (e.g., methyl, ethyl); the other symbols have the same definitions as those shown above.

Of the compounds included in the compound (I), a compound wherein ring A is a benzene ring which is substituted by a halogen atom, a lower alkyl group, a lower alkoxy group or a lower alkylenedioxy group, $R^2$ is a hydrogen atom, and X is N, can be produced by carrying out a reaction by a commonly known method (E. C. Taylor et al., Journal of Organic Chemistry, Vol. 32, pp. 1899–1900 (1967)), using a compound represented by the formula:

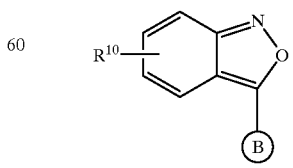

wherein $R^{10}$ represents a halogen atom, a lower alkyl group, a lower alkoxy group or a lower alkylenedioxy group present at any possible position on the benzene ring as a substituent, the number of substituents being 1 to 4; the other symbols have the same definitions as those shown above; in place of compound (VI) in scheme 1 above.

Of the compounds included in the compound (I) or the compound (II), a compound wherein $R^2$ is a lower alkyl group that may have a substituent, namely a compound (XIV) or compound (XIV'), can, for example, be produced by the method shown by scheme 2 below.

(Scheme 2)

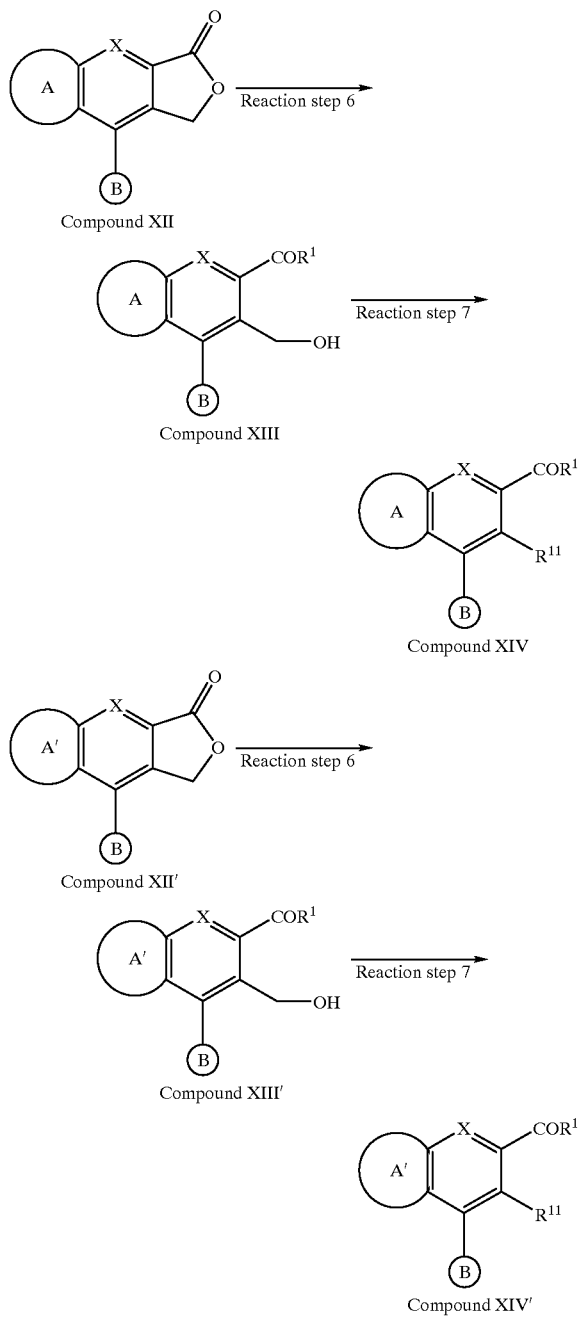

With respect to the compounds (XII) to (XIV) or compounds (XII') to (XIV') in scheme 2 above, $R^{11}$ represents a lower alkyl group that may have a substituent; the other symbols have the same definitions as those shown above.

Also, the compound (I) or compound (II) can also be synthesized by a compound represented by formula (XV) or (XV') by the method shown in scheme 3 below.

(Scheme 3)

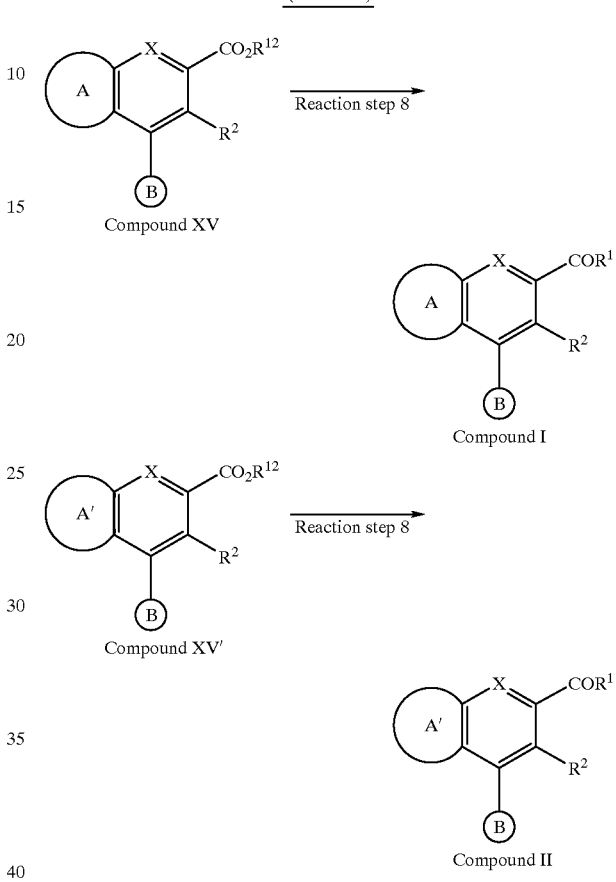

With respect to the compounds (XV) to (XV') in scheme 3 above, $R^{12}$ represents a hydrogen atom or a lower alkyl group that may be substituted; the other symbols have the same definitions as those shown above.

Examples of the lower alkyl group represented by $R^9$ to $R^{12}$ are a linear or branched $C_{1-6}$ alkyl group such as methyl, ethyl, propyl, isopropyl, butyl, isobutyl, sec-butyl, tert-butyl, pentyl and hexyl.

Examples of the substituent of the lower alkyl group the substituent of the homo- or hetero-cycle represented by the mentioned above ring A'.

Provided that, $R^{11}$ does not include a hydroxymethyl group.

The respective reactions of schemes 1 to 3 in the above-described production methods are hereinafter described in more detail.

Reaction processes 1 and 2 can be carried out in accordance with commonly known methods (e.g., J. G. Smith et al., Journal of Organic Chemistry, Vol. 53, pp. 2,942–2,953 (1988); T. Kuroda et al., Journal of Chemical Society Chemical Communications, pp. 1,635–1,636 (1991); T. Kuroda et al., Journal of Organic Chemistry, Vol. 59, pp. 7,353–7,357 (1994)).

Specifically, in reaction process 1, the compound [VI] or compound [VI'] is produced by treating the compound [VI] or compound [IV'] with a base to produce a dianion, and condensing it with the compound [V].

The base used is exemplified by alkyllithiums; preferable alkyllithiums include, for example, n-butyllithium, sec-butyllithium, tert-butyllithium, methyllithium and phenyllithium, with greater preference given to n-butyllithium. The amount of alkyllithium used is normally 2 to 10 mol, preferably 2 to 3 mol, per mol of the compound [IV] or compound [IV'].

The amount of the compound [V] used is normally 0.5 to 10 mol, preferably 1 to 3 mol, per mol of the compound [IV] or compound [IV'].

Also, said reaction can be advantageously carried out in a solvent. The solvent used is a solvent that does not adversely affect the reaction. Useful solvents include, for example, hydrocarbons (e.g., pentane, hexane, cyclohexane, benzene), ethers (e.g., diethyl ether, tetrahydrofuran, dioxane), amides (e.g., hexamethylphosphoric triamide) and ureas (e.g., 1,3-dimethyl-3,4,5,6-tetrahydro-2(1H)-pyrimidine). These solvents may be used singly, or in mixtures of 2 or more kinds mixed in appropriate ratios or as mixed solvents with water. The amount of solvents used is normally 1 to 100 milliliters, preferably 5 to 20 milliliters, per gram of the compound [IV] or compound [IV'].

Reaction temperature for the base and the compound [IV] or compound [IV'] is normally −72° C. to 200° C., preferably 0° C. to 50° C. Reaction time is normally 30 minutes to 24 hours, preferably 30 minutes to 12 hours.

Reaction temperature for the subsequent condensation with the compound [V] is normally −72° C. to 200° C., preferably 0° C. to 50° C. Reaction time is normally 30 minutes to 72 hours, preferably 30 minutes to 18 hours.

In reaction process 2, the compound [VIII] or compound [VIII'] is produced by treating the compound [VI] or compound [VI'] with an acid produce a condensed furan derivative in the reaction system, and condensing it with the compound [VII].

The acid used is an inorganic acid or an organic acid; preferable inorganic acids include, for example, hydrochloric acid, hydrobromic acid, nitric acid, sulfuric acid, phosphoric acid and polyphosphoric acid. Preferable organic acids include, for example, formic acid, acetic acid, trifluoroacetic acid, trichloroacetic acid, fumaric acid, oxalic acid, tartaric acid, maleic acid, citric acid, succinic acid, malic acid, methanesulfonic acid, benzenesulfonic acid and p-toluenesulfonic acid. The amount of acid used is normally 0.01 to 10 mol, preferably 0.03 to 2 mol, per mol of the compound [VI] or compound [VI'].

The amount of the compound [VII] used is normally 1 to 10 mol, preferably 1 to 3 mol, per mol of the compound [IV] or compound [VI'].

Also, said reaction can be advantageously carried out in a solvent. The solvent used is a solvent that does not adversely affect the reaction; useful solvents include, for example, hydrocarbons (e.g., pentane, hexane, cyclohexane, benzene, toluene), lower alcohols (e.g., methanol, ethanol, propanol), ethers (e.g., diethyl ether, tetrahydrofuran, dioxane) and halogenated hydrocarbons (e.g., dichloromethane, chloroform, 1,2-dichloroethane). Also, when the above-mentioned acids are liquid, they may be used as solvents. These solvents may be used singly, or in mixtures of 2 or more kinds mixed in appropriate ratios or as mixed solvents with water. The amount of solvents used is normally 1 to 100 milliliters, preferably 5 to 20 milliliters, per gram of the compound [VI] or compound [VI'].

Reaction temperature is normally −20° C., preferably 25° C. to 150° C.

Reaction time is normally 30 minutes to 24 hours, preferably 30 minutes to 12 hours.

In reaction process 3, the compound (IX) or compound (IX') is produced by subjecting the compound (VIII) or compound (VIII') to a hydrolytic reaction.

Said hydrolytic reaction can, for example, be carried out using a commonly known method (S. R. Sandler and W. Karo, "Organic Functional Group Preparations I," 2nd ed., Academic Press (1983), Chapter 9 (pp. 271–273)).

Also, when said hydrolytic reaction is carried out under acidic conditions, reaction process 4 can take place simultaneously with reaction process 3 to yield the compound (X) or compound (X').

In reaction process 4, the compound (X) or compound (X') is produced by subjecting the compound (IX) or compound (IX') to an aromatizing reaction for simultaneous dehydration and decarboxylation.

Although said aromatizing reaction is normally carried out by treating the compound (IX) or compound (IX') with an acid, it can also be carried out by keeping standing or heating the compound (IX) or compound (IX') under neutral conditions.

The acid used is an inorganic acid or an organic acid; preferable inorganic acids include, for example, hydrochloric acid, hydrobromic acid, nitric acid, sulfuric acid, phosphoric acid and polyphosphoric acid. Preferable organic acids include, for example, formic acid, acetic acid, trifluoroacetic acid, trichloroacetic acid, fumaric acid, oxalic acid, tartaric acid, maleic acid, citric acid, succinic acid, malic acid, methanesulfonic acid, benzenesulfonic acid and p-toluenesulfonic acid. The amount of acid used is normally 0.01 to 10 mol, preferably 0.03 to 2 mol, per mol of the compound (IX) or compound (IX').

Also, said reaction can be advantageously carried out in a solvent. The solvent used is a solvent that does not adversely; affect the reaction; useful solvents include, for example, hydrocarbons (e.g., pentane, hexane, cyclohexane, benzene), lower alcohols (e.g., methanol, ethanol, propanol), ethers (e.g., diethyl ether, tetrahydrofuran, dioxane) and halogenated hydrocarbons (e.g., dichloromethane, chloroform, 1,2-dichloroethane). Also, when the above-mentioned acids are liquid, they may be used as solvents. These solvents may be used singly, or in mixtures of 2 or more kinds mixed in appropriate ratios or as mixed solvents with water. The amount of solvent used is normally 1 to 100 milliliters, preferably 5 to 20 milliliters, per gram of the compound (IX) or compound (IX'). Reaction temperature is normally about −20° C. to about 200° C., preferably about 25° C. to about 150° C. Reaction time is normally 30 minutes to 24 hours, preferably 30 minutes to 12 hours.

In reaction process 5, the compound (XI) or compound (XI') is produced by subjecting the compound (X) or compound (X') to an amidating reaction, followed by an acylating reaction as necessary.

Said amidating reaction can, for example, be carried out using a commonly known method (S. R. Sandler and W. Karo, "Organic Functional Group Preparations I," 2nd ed., Academic Press (1983), Chapter 11 (pp. 315–358)).

Said acylating reaction can, for example, be carried out using a commonly known method (S. R. Sandler and W. Karo, "Organic Functional Group Preparations I," 2nd ed., Academic Press (1983), Chapter 7 (pp. 281–313)).

In reaction process 6, the compound [XIII] or compound [XIII'] is produced by subjecting the compound [XII] or compound [XII'] to a ring-opening reaction, followed by an acylating reaction as necessary.

The compound [XII] or compound [XII'],serving as the starting material, may, for example, be a lactone compound produced by commonly known methods (R. S. Burden et al.

Journal of the Chemical Society Section C, pp. 693–701, 1969; Archives of Pharmacology, 328(9), pp. 640–644, 1995; Indian Journal of Chemistry, Section B: Org. Chem. Include. Med. Chem., 33B(9), pp. 839–846, 1994; Indian Journal of Chemistry, Section B: 31B(7), pp. 401–406, 1992; Chemical and Pharmaceutical Bulletin, 32(1), pp. 31–37, 1984; Journal of the Chemical Society Section C, (11), pp. 2,091–2,094, 1971; Phytochemistry 29(9), pp. 2,991–2,993, 1990; Journal of Natural Products, 43(4), pp. 482–486, 1980; M. Anazini et al., Heterocycles, Vol. 38, pp. 103–111, 1994, etc.) or modification thereof.

The ring-opening reaction is carried out by reacting the compound [XII] or compound [XII'] with ammonia or an amine derivative represented by $HR^1$ ($R^1$ has the same definition as that shown above).

The ammonia used is aqueous ammonia or gaseous or liquid ammonia.

The amount of ammonia or amine derivative used is normally 1 mol to about 100 mol, preferably 2 to 10 mol, per mol of the compound [XII] or compound [XII'].

The reaction can be advantageously carried out in a solvent. The solvent used is a solvent that does not adversely affect the reaction; useful solvents include for example, hydrocarbons (e.g., pentane, hexane, cyclohexane, benzene), lower alcohols (e.g., methanol, ethanol, propanol), ethers (e.g., diethyl ether, tetrahydrofuran, dioxane), amides (e.g., N,N-dimethylformamide, hexamethylphosphoric triamide) and ureas (e.g., 1,3-dimethyl-3,4,5,6-tetrahydro-2 (1H)-pyrimidine). Also, when the amine derivative represented by $HR^1$ ($R^1$ has the same definition as that shown above) is liquid, it can also be used as a solvent. These solvents may be used singly, or in mixtures of 2 or more kinds mixed in appropriate ratios or as mixed solvents with water. The amount of solvent used is normally 1 to 100 milliliters, preferably 5 to 20 milliliters, per gram of the compound [XII] or compound [XII']. Reaction temperature is normally −20° C. to 200° C., preferably 25° C. to 150° C.; in some cases, the reaction can be advantageously carried out in a sealed tube.

Also, when the $R^1$ in $HR^1$ ($R^1$ has the same definition as that shown above) is an acylated amino group, said reaction can be advantageously proceeded in the presence of a base.

The base used is exemplified by alkyllithium reagents (e.g., methyllithium, n-butyllithium, sec-butyllithium, tert-butyllithium, preferably n-butyllithium); inorganic bases (e.g., sodium hydroxide, potassium hydroxide, sodium carbonate, potassium carbonate, sodium hydrogen carbonate, potassium hydrogen carbonate, cesium carbonate, sodium hydride, metallic sodium) and organic bases (e.g., sodium methoxide, sodium ethoxide, triethylamine, pyridine, diethylisopropylamine). The amount of base used is normally 1 to about 10 mol, preferably 1 to 2 mol, per mol of the compound [XII] or compound [XII'].

Reaction time is normally 30 minutes to 1 week, preferably 30 minutes to 4 days.

The acylating reaction carried out after the ring-opening reaction as necessary can, for example, be carried out using the method described for reaction process 5.

In reaction process 7, the compound (XIV) or compound (XIV') is produced by subjecting the compound (XIII) or compound (XIII') to a functional group-converting reaction, a carbon-adding reaction or an appropriate combination thereof.

Said functional group-converting reaction or carbon-adding reaction can, for example, be carried out by commonly known methods (J. Mathieu and J. Weil-Raynal, "Formation of C—C Bonds I–III, " George Thieme Publishers, Stuttgart (1973, 1975, 1979); S. R. Sandler and W. Karo, "Organic Functional Group Preparations I–III," 2nd ed., Academic Press (1983, 1986, 1989) etc.).

In reaction process 8, the compound (I) or compound (II) is produced by subjecting the compound (XV) or compound (XV') to an amidating reaction, followed by an acylating reaction as necessary.

The compound (XV) or compound (XV'), serving as the starting material, may, for example, be a carboxylic acid derivative produced by commonly known methods (e.g., G. Jones ed., "Quinolines Part 1, " John Wiley & Sons (1977), Chapter 2 (pp. 93–318); L. S. El-Assal et al., Journal of Chemical Society, pp. 1,658–1,662, (1961); D. Delorme et al., Journal of Medicinal Chemistry, Vol. 39, pp. 3,951–3, 970, (1996)) or modifications thereof.

The amidating reaction can, for example, be carried out using a commonly known method (S. R. Sandler and W. Karo, "Organic Functional Group Preparations I," 2nd ed., Academic Press (1983)), Chapter 11 (pp. 315–358)).

The acylating reaction can, for example, be carried out using the method described for reaction process 5.

Also, when the desired compound is produced by the methods shown by schemes 1 through 3 above, and provided that the substituents or rings A and B in the compounds (IV) through (XV) and the compounds (IV') through (XV') contain a functional group such as a hydroxyl group, an amino group, a mono-$C_{1-6}$ alkylamino group, a ketone, a carboxyl group or a tetrazolyl group, for example, these functional groups may be protected; regarding the kind of protecting group, and methods of protection and deprotection, a commonly known method (T. W. Green and P. G. M. Wuts, "Protective Groups in Organic Chemistry," 2nd ed., John Wiley & Sons, Inc., (1991)) etc. are used.

The thus-obtained compound (I), compound (II) or a salt thereof can be isolated and purified by commonly known means (e.g., redissolution, concentration, solvent extraction, fractional distillation, crystallization, recrystallization, chromatography).

Also, the salt of the compound (I) or compound (II) of the present invention is preferably a pharmaceutically acceptable salt, exemplified by salts with inorganic bases, salts with organic bases, salts with inorganic acids, salts with organic acids, and salts with basic or acidic amino acids. Preferable salts with inorganic bases include, for example, alkali metal salts (e.g., sodium salt, potassium salt), alkaline earth metal salts (e.g., calcium salt, magnesium salt), aluminum salt and ammonium salt. Preferable salts with organic bases include, for example, salts with trimethylamine, triethylamine, pyridine, picoline, ethanolamine, diethanolamine, triethanolamine, dicyclohexylamine, N,N'-dibenzylethylenediamine etc.

Preferable salts with inorganic acids include, for example, salts with hydrochloric acid, hydrobromic acid, nitric acid, sulfuric acid, phosphoric acid etc.

Preferable salts with organic acids include, for example, salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid etc.

Preferable salts with basic amino acids include, for example, salts with arginine, lysine, ornithine etc.

Preferable salts with acidic amino acids include, for example, salts with aspartic acid, glutamic acid etc. Also, when the desired product is obtained in free form, it may be converted to a salt by a conventional method; when the desired product is obtained as a salt, it may be converted to the free compound by a conventional method.

The compound (I) or compound (II) of the present invention or a salt thereof may be a hydrate or non-hydrate.

The compound (I) or compound (II) or a salt thereof may be isolated and purified by commonly known means, e.g., solvent extraction, liquid nature conversion, redissolution, crystallization, recrystallization and chromatography. Also, although the starting compound for the compound (I) or compound (II) or a salt thereof may be isolated and purified by the same known means as those shown above, it may be used as a starting material for the next process as a reaction mixture as is without isolation.

When the compound (I) or compound (II) of the present invention or a salt thereof contains an optical isomer, a stereoisomer, a position isomer or a rotational isomer, these isomers are also included in the scope of the compounds of the present invention, and each can be obtained as a single product by commonly known means of synthesis or separation. For example, when an optical isomer is present in the compound of the present invention, the optical isomer resolved from said compound is also included in the scope of the present invention.

An optical isomer can be produced by commonly known methods. Specifically, an optical isomer is obtained by using an optically active synthesis intermediate or by optically resolving the final racemate mixture by a conventional method.

Useful methods of optical resolution include commonly known methods, e.g., the fractional recrystallization method, chiral column method and diastereomer method described below.

(1) Fractional recrystallization method

A salt of a racemate and an optically active compound is formed and separated by the fractional recrystallization method to yield a free optical isomer via a neutralization process is desired.

(2) Chiral column method

A racemate or a salt thereof is applied to a column for optical isomer separation (chiral column) to separate it. In the case of liquid chromatography, for example, optical isomers are separated by adding a mixture thereof to a chiral column such as ENANTIO-OVm (produced by Tosoh Corporation), and developing it in water, various buffers (e.g., phosphate buffer) and organic solvents (e.g., ethanol, methanol, acetonitrile) as a simple or mixed solution. Also, in the case of gas chromatography, for example, a chiral column such as CP-Chirasil-DeX CB (produced by GL Science) is used to separate optical isomers.

(3) Diastereomer method

A diastereomer mixture, prepared from a racemate mixture using an optically active reagent and chemical reaction, is treated by ordinary means of separation (e.g., fractional recrystallization, chromatography) etc. to obtain a single substance, after which the optically active reagent moiety is cut off by a chemical treatment such as hydrolysis reaction. When the compound of the present invention has a hydroxyl group or a primary or secondary amino group in the molecular structure thereof, an ester or amide diastereomer, respectively, is obtained by subjecting said compound, an optically active organic acid (e.g., MPTA [α-methoxy-α-(trifluoromethyl)phenylacetic acid], (−)-methoxyacetic acid) etc. to a condensation reaction. On the other hand, when the compound (I) of the present invention has a carboxylic acid group, an ester or amide diastereomer, respectively, is obtained by subjecting said compound and an optically active amine or an alcohol reagent to a condensation reaction. The diastereomer separated is converted to an optical isomer of the original compound by an acid hydrolysis or basic hydrolysis reaction.

The cell differentiation induction factors serving as targets of the present invention include factors which induce a character characteristic of the process of differentiation of undifferentiated precursors of cells which maintain living body function in particular tissue, such as osteoblasts and neurons, e.g., factors belonging to the TGF-β superfamily such as bone morphogenetic protein, neurotrophic factors, transforming growth factor (TGF)-β and activin, factors belonging to the FGF superfamily such as basic fibroblast growth factor (bFGF) and acidic fibroblast growth factor (aFGF), factors belonging to the neuropoietic cytokine family such as leukemia inhibitory factor (LIF, or also called cholinergic differentiation factor (CDF)) and ciliary neurotrophic factor (CNTF), interleukin 1 (IL-1, hereinafter similarly abbreviated), IL-2, IL-3, IL-5, IL-6, IL-7, IL-9, IL-11, tumor necrosis factor-α (TNF-α) and interferon-γ (INF-γ), with preference given to bone morphogenetic protein and neurotrophic factors.

Bone morphogenetic factors include members of the MBP family of proteins which promote osteogenesis and chondrogenesis, such as BMP-2, -4, -5, -6, -8, -9, -10, -11 and -12, with preference given to BMP-2, -4, -6 and -7. BMP may be a homo-dimer of each of the above-mentioned factors or a hetero-dimer consisting of any possible combination thereof.

Neurotrophic factors include nerve growth factor (NGF), brain-derived neurotrophic factor (BDNF) and neurotrophic-3 (NT-3) and glial cell line-derived neurotrophic factor (GDNF), with preference given to the NGF family.

The compound (I) or compound (II) of the present invention or a salt thereof can be safely administered orally or non-orally (e.g., topical, rectal and intravenous administration), as such or in the form of pharmaceutical compositions formulated with a pharmaceutically acceptable carrier, e.g., tablets (including sugar-coated tablets and film-coated tablets), powders, granules, capsules (including soft capsules), syrups, emulsions, suspensions, injectable preparations (e.g., subcutaneous, intradermal, intramuscular injections), suppositories and sustained-release preparations, in accordance with a commonly known method. The content of compound (I), compound (II) or a salt thereof in the preparation of the present invention 0.1 to 100% by weight relative to the entire preparation. Varying depending on subject of administration, route of administration, target disease etc., the daily dose of the compound (I) or (II) of the present invention or a salt thereof is normally about 0.1 to 500 mg, preferably about 1 to 100 mg, and more preferably about 5 to 100 mg, per day, based on the active ingredient, per adult (60 kg), administered in 1 to several portions per day, when it is used in a cell differentiation induction factor action agent or an enhancer for said action, for example.

Said injectable preparation is used by a commonly known method, i.e., the compound (I) or (II) or a salt thereof is used as such or in combination with a substance exhibiting cell differentiation induction factor action, e.g., BMP or neurotrophic factor. Aqueous solutions for injection include physiological saline and isotonic solutions, and may be used as necessary in combination with the suspending agents shown below. Oily liquids include sesame oil and soybean oil, and may be used in combination with the dissolution aids shown below. The injectable preparation prepared is normally filled in appropriate ampules.

Pharmacologically acceptable carriers used to produce the preparation of the present invention are various organic or inorganic carrier substances in common use as pharmaceutical materials, including excipients, lubricants, binders and disintegrants for solid preparations, and solvents, dissolution aids, suspending agents, isotonizing agents, buffers and soothing agents for liquid preparations. Other pharmaceutical additives such as preservatives, antioxidants, coloring agents, sweetening agents, adsorbents and wetting agents may be used as necessary. Excipients include, for example, lactose, sucrose, D-mannitol, starch, corn starch, crystalline cellulose and light silicic anhydride. Lubricants include, for example, magnesium stearate, calcium stearate, talc and colloidal silica.

Binders include, for example, crystalline cellulose, sucrose, D-mannitol, dextrin, hydroxypropyl cellulose, hydroxypropylmethyl cellulose, polyvinylpyrrolidone, starch, saccharose, gelatin, methyl cellulose and carboxymethl cellulose sodium.

Disintegrants include, for example, starch, carboxymethyl cellulose, carboxymethyl cellulose calcium, croscarmellose sodium, carboxymethyl starch sodium and L-hydroxypropyl cellulose.

Solvents include, for example, water for injection, alcohol, propylene glycol, macrogol, sesame oil and corn oil.

Dissolution aids include, for example, polyethylene glycol, propylene glycol, D-mannitol, benzyl benzoate, ethanol, trisaminomethane, cholesterol, triethanolamine, sodium carbonate and sodium citrate.

Suspending agents include, for example, surfactants such as stearyltriethanolamine, sodium lauryl sulfate, laurylaminopropionic acid, lecithin, benzalkonium chloride, benzethonium chloride and monostearic glycerol; and hydrophilic polymers such as polyvinyl alcohol, polyvinylpyrrolidone, carboxymethyl cellulose sodium, methyl cellulose, hydroxymethyl cellulose, hydroxyethyl cellulose and hydroxypropyl cellulose.

Isotonizing agents include, for example, glucose, D-sorbitol, sodium chloride, glycerol and D-mannitol.

Buffers include, for example, buffer solutions of phosphates, acetates, carbonates, citrates etc.

Soothing agents include, for example, benzyl alcohol.

Preservatives include, for example, p-oxybenzoic acid esters, chlorobutanol, benzyl alcohol, phenethyl alcohol, dehydroacetic acid and sorbic acid.

Antioxidants include, for example, sulfites and ascorbic acid.

Since a pharmaceutical composition containing the compound (I) or compound (II) or a salt thereof exhibits excellent cell differentiation-inducing action and cell differentiation-inducing factor action-enhancing action, it is useful in the treatment and prevention of various nerve diseases (e.g., diseases based on nerve degeneration, such as those in cerebrovascular dementia, senile dementia or Alzheimer's disease; motor neuronal disease such as amyotrophic lateral scelerosis (Lou Gehrig disease); or diabetic peripheral neuropathy) or bone/joint diseases (e.g., bone fractures, osteoporosis, osteoarthritis, rheumatoid arthritis); specifically, agents for treating or preventing bone/joint diseases include, for example, osteogenesis promoters, cartilage destruction suppressors, bone fracture healing promoters or bone reconstruction promoters, when used alone or in combination with substances exhibiting cell differentiation induction factor action (e.g., BMP, neurotrophic factors).

Furthermore, because not all roles of BMP, neurotrophic factor, etc. in the living body have been clarified, it is likely that pathologic condition can be improved in other diseases by enhancing the actions of BMP, neurotrophic factors, etc.

The cell differentiation-inducing action agent or cell differentiation-inducing factor action-enhancing agent of the present invention can also be used as an agent for treating or preventing such diseases associated with BMP, neurotrophic factors, etc.

The cell differentiation-inducing action agent or cell differentiation-inducing factor action-enhancing agent of the present invention can be used in the above-mentioned diseases not only in humans but also in other mammals (e.g., mice, rats, rabbits, dogs, cats, bovines, pigs).

Also, a pharmaceutical composition containing the compound (I) or compound (II) of the present invention or a salt thereof is of low toxicity and has few side effects.

The cell differentiation-inducing action agent or cell differentiation-inducing factor action-enhancing of the present invention can be mixed in a carrier for bone reconstruction as an osteogenesis promoter in bone repair and bone transplantation because it possesses potent osteogenesis-promoting activity. For example, the compound of the present invention can be used as adhered to, or contained in, artificial bones etc. prepared from metals, ceramics or high-molecular substances. The artificial bone is preferably made porous on the surface thereof to allow the cell differentiation induction factor action enhancer of the present invention to be released in living tissue upon its transplantation to a bone defect. The compound of the present invention can be adhered to, or contained in, an artificial bone by dispersing it in an appropriate dispersant, binder, diluent or the like (e.g., collagen, physiological saline, citric acid solution, acetic acid solution, hydroxyapatite, fibrin, mixture thereof) and applying it to, or impregnating it in, the artificial bone, followed by drying. Such artificial bone is transplanted to a bone defect and firmly fixed to the defect. An artificial bone fixative can be prepared by mixing the active ingredient helioxanthine with dispersants, binders, diluents, other components effective on bone regeneration (e.g., calcium), etc. that are physiologically acceptable for pharmaceutical use. The artificial bone fixative can also be used to fill in the gap between the artificial bone transplanted to the bone defect in the hose and the bone defect, without adhering it to, or containing it in, the artificial bone. It should be noted that the non-oral composition described here can also be used with an osteogenesis-promoting protein such as the BMP family adhered thereto or contained therein.

Mode of Working The Invention

The present invention is described in more detail by the following Reference Examples, Examples, Formulation Examples and Experimental Examples but they are merely illustrative and should not be construed as limiting the scope of the invention. Thus, many modifications may be made without from the scope of the invention.

In the column chromatography in the following Reference Examples and Examples, elutions (developing solvent was indicated in brackets) were carried out under thin-layer chromatography monitoring.

The TLC monitoring was carried out using Kieselgel 60F$_{254}$ (layer thickness 0.25 mm, Merck) for TLC plates, the solvents which were used in the column chromatography as developers, UV detector and phosphomolyvdate color reaction for detector. As silica gel for column chromatography, Kieselgel 60 (70–230 mesh, Merck) was used. The NMR spectra represent proton NMR ($^1$H-NMR) spectra, which were measured with Gemini 200 (produced by Varian) using tetramethylsilane either as internal or external standard and expressed in δ (ppm).

The infrared absorption Spectra were recorded with IR-810 spectrophotometer (Nippon Bunko Kogyo). The melting points were determined with the Yanagimoto micromelting point meter MP-500D and the uncorrected values were shown. The "room temperature" in the following Reference and Working Examples means 0° C.–30° C., preferably about 15° C.–25° C.

In the chemical formulas in the following Examples and Reference Examples, Me stands for methyl and Ms for methanesulfonyl. The other symbols or abbreviations used in the present specification have the following meanings.

| | |
|---|---|
| S | singlet |
| d | doublet |
| dd | double doublet |
| t | triplet |
| m | multiplet |
| br | broad |
| J | coupling constant |
| Hz | Hertz |
| THF | tetrahydrofuran |
| DMF | N,N-dimethylformamide |
| DME | dimethoxyethane |
| CDCl | deuterochloroform |
| DMSO-$d_6$ | deuteromethylsulfoxide |
| NMR | proton nuclear magnetic resonance |

REFERENCE EXAMPLE 1

10-(4-Methoxyphenyl)-furo[3',4':6,7]naphtho[1,2-d]-1,3-dioxol-7(9H)-one

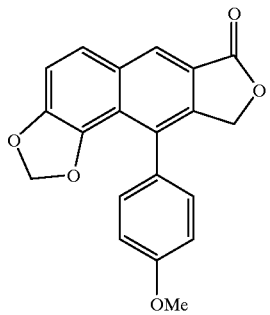

Butyl lithium (1.6M hexane solution: 36 ml) was added dropwise to a solution of helioalcohol (4.0 g) in benzene (200 ml) at room temperature. The mixture was stirred at room temperature for two hours, followed by addition of a solution of 4-methoxybenzonitrile (3.9 g:1.1 equivalent) in benzene (50 ml). The mixture was stirred at room temperature overnight, followed by addition of water and extraction with ether. The organic layer was washed with water, dried over magnesium sulfate and concentrated under reduced pressure. The residue was dissolved in toluene (250 ml), followed by addition of maleic anhydride (7.7 g) and p-toluenesulfonic acid (1.0 g). The mixture was refluxed for 20 hours, and the precipitated solid was filtered off. The filtrate was concentrated under reduced pressure. Conc. HCl was added to the residue. The mixture was refluxed for one hour and cooled to room temperature. The resulting yellowish brown precipitate was collected by suction, washed with water and recrystallized from THF to yield acid anhydride (about 3.4 g). Sodium borohydride (0.8 g) was suspended in DME (80 ml), followed by addition of the above anhydride at 0° C. The mixture was stirred at 0° C. for 30 minutes and poured into ice-cooled diluted HC. The resulting product was extracted with ethyl acetate. The extract was dried over magnesium sulfate and concentrated under reduced pressure. The residue was purified by column chromatography (eluent:chloroform) to yield the title compound (1.5 g). Some portions of the compound was recrystallized from THF to be used for elemental and instrumental analysis.

m.p.: 217–219° C.

NMR (CDCl$_3$) δ: 3.90 (3H,s), 5.20 (2H,s), 5.93 (2H,s), 6.99 (1H,d,J=9 Hz), 7.28 (1H,d,J=9 Hz), 7.32 (1H,d,J=9 Hz), 7.72 (1H,d,J=9 Hz), 8.43 (1H,s).

Elemental Analysis for $C_{20}H_{14}O_5 \cdot 0.5H_2O$

Calcd: C, 70.58%; H, 4.34%

Found: C, 70.52%; H, 4.38%

REFERENCE EXAMPLE 2

10-(4-Chlorophenyl)-furo[3',4';6,7]naphtho[1,2-d]-1,3-dioxol-7(9H)-one

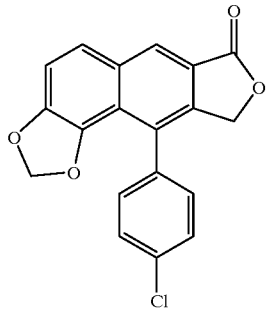

The title compound was produced in a similar manner to that in Reference Example 1.

m.p.: 225–227° C.

NMR (CDCl$_3$) δ: 5.18 (2H, s), 5.93 (2H,s), 7.33 (3H,m), 7.44 (2H,d,J=8 Hz), 7.73 (1H,d,J=8 Hz), 8.45 (1H,s).

Elemental Analysis for $C_{19}H_{11}O_4Cl \cdot 0.2H_2O$

Calcd: C, 66.66%; H, 3.36%

Found: C, 66.59%; H, 3.14%

Reference Example 3

10-(2-Naphthyl)-furo[3',4';6,7]naphtho[1,2-d]dioxol-7(9H)-one

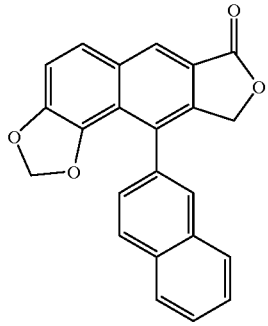

The title compound was produced in a similar manner to that in Reference Example 1.

m.p.: 224–226° C.

NMR (CDCl$_3$) δ: 5.13(1H,d,J=15.2 Hz), 5.29 (1H,d,J=15.2 Hz), 5.85 (1H,d,J=1.4 Hz), 5.85 (1H,d,J=1.4 Hz), 7.334

(1H,d,J=8.8 Hz), 7.43 (1H,d,J=8.2 Hz, 1.8 Hz), 7.57 (2H,m), 7.75 (1H,d,J=8.8 Hz), 7.8–8.0 (4H,m), 8.48 (1H,s).

Elemental Analysis for $C_{23}H_{14}O_4$

Calcd: C, 77.96%; H, 3.98%

Found: C, 77.57%; H, 4.10%

REFERENCE EXAMPLE 4

10- (4-Fluorophenyl)-furo[3', 4':6,7]naphtho[1,2-d]-1,3-dioxol-7(9H)-one

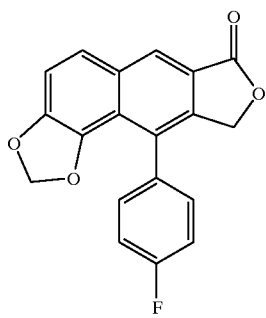

The title compound was produced in a similar manner to that in Reference Example 1.

m.p.: 215–218° C.

NMR (CDCl$_3$) δ: 5.18 (2H,s), 5.92(2H,s), 7.15 (2H,m), 7.33 (3H,m) 7.73 (1H,d,J=8.8 Hz), 8.45 (1H,s).

Elemental Analysis for $C_{19}H_{11}O_4F$

Calcd: C, 70.81%; H, 3.44%

Found: C, 70.57%; H, 3.65%

REFERENCE EXAMPLE 5

10-(4-Methylphenyl)-furo[3',4',:6,7]naphtho[1,2-d]-1,3 -dioxol-7(9 H)-one

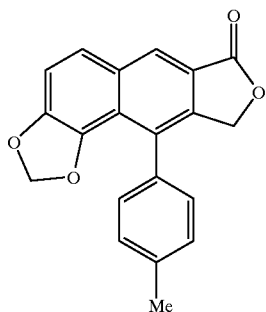

The title compound was produced in a similar manner to that in Reference Example 1.

m.p.: 208 –210° C.

NMR (CDCl$_3$) δ: 1.45 (3H,s), 5.19(2H,s), 7.25(4H,s), 7.32(1H,d,J=8.4 Hz), 7.72(1H, d,J=8.4 Hz), 8.43 (1H,s).

Elemental Analysis for $C_{20}H_{14}O_4$

Calcd: C, 75.46%; H, 4.43%

Found: C, 75.17%; H, 4.52%

REFERENCE EXAMPLE 6

10-(1,3-Benzodioxole-5-yl)-1,3-dioxolo[4,5-f]furo[3,4-b]quinolin-7(9 H)-one

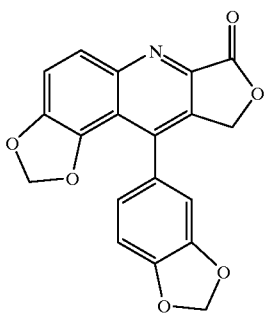

Diethyl 9-(1,3-benzodioxole-5-yl)-1,3-dioxolo[4,5-f]furo[3,4-b]quinoline-7(9H)-one dicarboxylate (2.4 g) was added gradually to a suspension of LAH (lithium aluminium hydride (2.0 g) in THF (50 ml) at 0° C. The mixture was stirred at room temperature for one hour, followed by addition of water to stop the reaction. The resulting precipitate was filtered off through Celite®. The filtrate was extracted with ethyl acetate. The extract was washed with water, dried over magnesium sulfate and concentrated under reduced pressure. The residue was dissolved in ethanol (100 ml) and, with addition of 10% Pd-C (2.5 g), stirred at room temperature overnight. The catalyst was filtered off, and the solvent was distilled off under reduced pressure. The residue was dissolved in chloroform (300 ml), followed by addition of manganese dioxide (20 g). The mixture was stirred at room temperature for 3 hours. The manganese dioxide was filtered off through Celite®. The filtrate was concentrated under reduced pressure. The resulting crude crystals were washed with diisopropyl ether to yield the title compound (0.9 g). Some portions of the compound were recrystalized from THF to be used for elemental and instrumental analysis.

m.p.: 272–274° C.

NMR (CDCl$_3$) δ: 5.30(1H,d,J=16 Hz), 5.41(1H,d,J=16 Hz), 6.05(2H,d,J=4 Hz), 6.10(2H,d,J=4 Hz), 6.86(2H,m), 6.95(1H,d,J=8 Hz), 7.57(1H,d,J=9 Hz), 8.11(1H,d,J=9 Hz).

Elemental Analysis for $C_{19}H_{11}NO_6$

Calcd: C, 65.33%; H, 3.17%; N, 4.01%

Found: C, 64.91%; H, 3.07%; N, 4.18%

REFERENCE EXAMPLE 7

5-Phenyl-7-methyl-furo[3,4-b]quinolin-2 (4H)-one

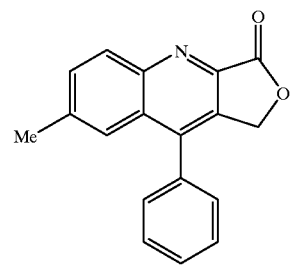

The title compound was produced in a similar manner to that in Reference Example 6.

m.p.: 191–193° C.

NMR (CDCl$_3$) δ: 2.52(3H,s), 5.38(2H,s), 7.40–7.50(2H, m), 7.57–7.75(5H,m), 8.34(1H,d,J=9 Hz).

IR(KBr): 1780, 1500, 1455, 1372, 1131, 1054 cm$^{-1}$

Elemental Analysis for C$_{18}$H$_{13}$NO$_2$

Calcd: C, 78.53%; H, 4.76%; N, 5.09%

Found: C, 78.37%; H, 4.71%; N, 5.18%

REFERENCE EXAMPLE 8

5-(2,4-Difluorophenyl)-7-methyl-furo[3,4-b]quinolin-2 (4 H)-one

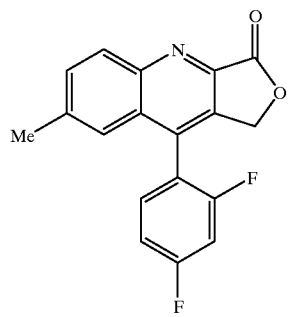

The title compound was produced in a similar manner to that in Reference Example 6.

m.p.: 218–220° C.

NMR (CDCl$_3$) δ: 2.54(3H,s), 5.29(1H,d,J=15 Hz), 5.39 (1H,d,J=15 Hz), 7.06–7.21(2H,m), 7.34–7.50(2H,m), 7.72 (1H,dd,J=1.8 Hz,8 Hz), 8.36(1 Hz,d,J=8 Hz).

IR(KBr): 1768, 1500, 1455, 1423, 1374, 1142, 1093, 1060 cm$^{-1}$

Elemental Analysis for C$_{18}$H$_{11}$F$_2$NO$_2$

Calcd: C, 69.45%; H, 3.56%; N, 4.50%

Found: C, 69.33%; H, 3.56%; N, 4.59%

REFERENCE EXAMPLE 9

9-(4-Methoxyphenyl)-naphtho[1,2-d]-1,3-dioxole-7-carboxylic acid

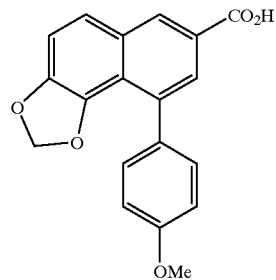

Butyl lithium (1.6M hexane solution: 36 ml) was added dropwise to a solution of helioalcohol (4.0 g) in benzene (100 ml) at room temperature. The mixture was stirred at room temperature for one hour, followed by addition of 4-methoxybenzonitrile (3.85 g) in benzene (20 ml). The mixture was stirred at room temperature overnight, followed by addition of water and extraction with ether. The organic layer was washed with water, dried over magnesium sulfate and concentrated under reduced pressure. The residue was dissolved in toluene (75 ml), followed by addition of dimethyl fumarate (7.58 g) and trichloroacetic acid (0.3 g). The mixture was refluxed for 3 hours and concentrated under reduced pressure. The reside was dissolved in ethyl acetate and washed with water, an aqueous saturated sodium hydrogen carbonate solution and brine, dried over magnesium sulfate and concentrated under reduced pressure. The residue was purified with silica gel column chromatography (silica gel: 50 g. eluent:ethyl acetate–hexane=1:2) to yield tetrahydro-2,4-epoxynaphthalene derivative (2.84 g) as a mixture of diastereoisomers. This was dissolved in a mixture of THF (5 ml) and methanol (5 ml), followed by addition of an aqueous NaOH (1.1 g) solution (5 ml). The mixture was stirred overnight and concentrated under reduced pressure. After being diluted with water, the mixture was washed with ethyl acetate. Conc. HCl was added to the aqueous layer until its pH becomes about 2.The mixture was extracted with ethyl acetate. The extract was washed with brine, dried over magnesium sulfate and concentrated under reduced pressure. The residue was dissolved in ether (50 ml), followed by addition of conc. HCl. The mixture was refluxed for 10 minutes and concentrated under reduced pressure, followed by addition of water. The resulting precipitate was collected by filtration and washed with methanol and ether to yield the title compound (2.64 g).

m.p.: 264–266° C.

NMR (CDCl$_3$+CD$_3$OD) δ: 3.89(3H,s), 5.95(2H,s), 6.90–7.00(2H,m), 7.27(1H,d,J=9 Hz), 7.34–7.43(2H,m), 7.64(1H,d,J=9 Hz), 7.86(1H,d,J=1.6 Hz), 8.55(1H,d,J=1.6 Hz).

REFERENCE EXAMPLE 10

9-(4-Trifluoromethylphenyl)-naphtho[1,2-d]-1,3-dioxole-7-carboxylic acid

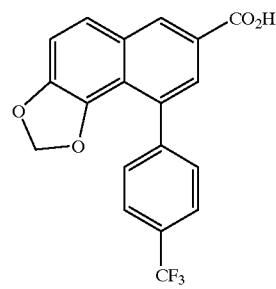

The title compound was produced in a similar manner to that in Reference Example 9.

m.p.: 207–209° C.

NMR (DMSO) δ: 6.02(2H,s), 7.52(1H,d,J=8 Hz), 7.69 (1H,d,J=8 Hz), 7.72(1H,d,J=1.4 Hz),l 7.78(1H,d,J=8 Hz), 7.92(1H,d,J=8 Hz), 8.66(1H,d,J=1.4 Hz).

REFERENCE EXAMPLE 11

9-(1,3-Benzodioxole-5-yl)-6-methyl-naphtho[1,3-d] 1,3-dioxole-7-carboxylic acid

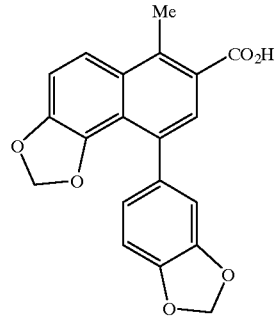

The title compound was produced in a similar manner to that in Reference Example 9.

m.p.: 233–235° C.

NMR (CDCl$_3$+DMSO) δ: 2.96(3H,s), 5.94(2H,s), 6.02 (2H,s), 6.79–6.93(3H,m), 7.27(1H,d,J=9 Hz), 7.69(1H,s), 7.86(1H,d,J=9 Hz).

REFERENCE EXAMPLE 12

9-(1,3-Benzodioxole-5-yl)-naphtho[1,2-d]- 1,3-dioxole-7-carboxylic acid

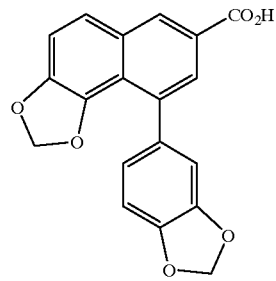

The title compound was produced in a similar manner to that in Reference Example 9.

m.p.: 267–269° C.

NMR (DMSO) δ: 6.03(2H,s), 6.09(2H,s), 6.89(1H,dd,J= 1.5 Hz, 8 Hz), 6.96(1H,d,J=8 Hz), 7.00(1H,d,J=1.5 Hz), 7.47(1H,d,J=9 Hz), 7.66(1H,d,J=1.6 Hz), 7.86(1H,d,J=9 Hz), 8.57(1H,d,J=1.6 Hz).

REFERENCE EXAMPLE 13

9-(1,3-Benzodioxole-5-yl)-8-methyl-naphtho[1,2-d]-1,3-dioxole-7-carboxylic acid (a) Methyl 9-(1,3-benzodioxole-5-yl)-8-methanesulfonyloxymethyl-naphtho[1,2-d]-1,3-dioxole-7-carboxylate

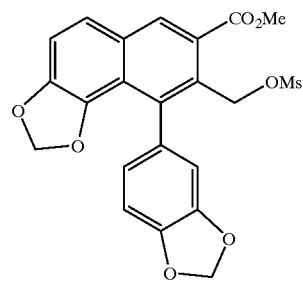

1N NaOH solution (2.9 ml) was added to a solution of helioxanthin (1 g) in DMF (10 mol). The mixture was heated at 60° C. for 30 minutes. The solvent was evaporated under reduced pressure. The residue was dissolved in DMF (10 ml), followed by addition of methyl iodine. The mixture was heated at 60° C. for one hour. The solvent was distilled off under reduced pressure. Water was added to the residue. The mixture was extracted with ethyl acetate. The extract was washed with brine, dried over magnesium sulfate and concentrated under reduced pressure. The residue was dissolved in THF (10 ml), followed by addition of triethylamine (0.80 ml). Methanesulfonylchloride (0.22 ml) was added dropwise to the mixture under ice-cooling. The mixture was stirred for 30 minutes, followed by addition of water. The mixture was extracted with ethyl acetate. The extract was washed with brine, dried over magnesium sulfate and concentrated under reduced pressure to yield the title compound (1.25 g). The crude compound thus produced was used in the subsequent reaction without further purification.

NMR (CDCl$_3$) δ: 3.00(3H,s), 3.91(3H,s), 5.24(1H,d,J=10 Hz), 5.34(1H,d,J=10 Hz), 5.91(1H,d,J=1.2 Hz), 5.94(1H,d,J=1.2 Hz), 6.09(1H,d,J=0.8 Hz), 6.13(1H,d,J=0.8 Hz), 6.73 (1H,dd,J=1.6 Hz, 8 Hz), 6.86(1H,d,J=1.6 Hz), 6.98(1H,d,J=8 Hz), 7.49(1H,d,J=9 Hz), 7.81(1H,d,J=9 Hz), 8.54(1H,s).

(b) Methyl 9-(1,3-benzodioxole-5-yl)-8-methyl-naphtho[1,2-d]-1,3-dioxole-7-carboxylate

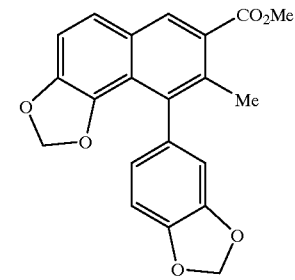

Sodium borohydride (36 mg) was added to a solution of methyl 9-(1,3-dioxole-5-yl)-8-methanesulfonyloxymethyl-naphtho[1,2-d]-1,3-dioxole-7-carboxylate (443 mg) in DMF (5 ml), and the mixture was stirred overnight.

Water was added to the mixture to stop the reaction. The product was extracted with ether. The extract was washed with brine, dried over magnesium sulfate and concentrated under reduced pressure. The residue was purified with column chromatography (silica gel: 50 g, eluent: ethyl acetate: hexane=1:4) to yield the title compound (1.5 g).

NMR (CDCl$_3$) δ: 2.34(3H,s), 3.95(3H,s), 5.81(1H,d,J=1.5 Hz), 5.82(1H,d,J=1.5 Hz), 6.03(1H,d,J=1.4 Hz), 6.06(1H,d,J=1.4 Hz), 6.67(1H,dd,J=1.6 Hz, 8 Hz) 6.70(1H,d,J=1.6 Hz), 6.86(1H,d,J=8 Hz), 7.16(1H,d,J=9 Hz), 7.49(1H,d,J=9 Hz), 8.33(1H,s).

(c) 9-(1,3-Benzodioxole-5-yl)-8- methyl-naphtho[1,2-d]-1,3-dioxole-7-carboxylic acid

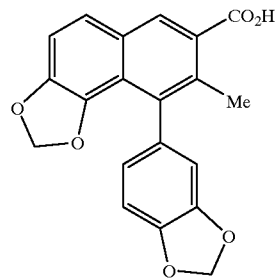

Methyl 9-(1,3-benzodioxole-5-yl)-8-methyl-naphtho[1,2-d]-1,3-dioxole-7-carboxylate was dissolved in a mixture of THF (6 ml) and methanol (3 ml). After addition of 1N NaOH (3 ml), the mixture was stirred for 4 days. 1N HCl was added to the reaction mixture, followed by addition of water. The resulting precipitate was collected by filtration to yield the title compound (264 mg). Some portions of the compound was recrystalized from methanol-chloroform to be used for elemental and instrumental analysis.

NMR (DMSO) δ: 2.24(3H,s), 5.83(1H,brs), 5.86(1H,brs), 6.05(1H,brs), 6.11(1H,brs), 6.65(1H,dd,J=1.6 Hz,8 Hz), 6.78(1H,d,J=1.6 Hz), 6.94(1H,d,J=8 Hz), 7.32(1H,d,J=8 Hz), 7.68(1H,d,J=8 Hz), 8.37(1H,s).

REFERENCE EXAMPLE 14

9-(1,3-Benzodioxole-5 yl)-8-methyl-1,3-dioxolo[4,5-f]quinoline-7-carboxylic acid.

(a) Methyl 9-(1,3-benzodioxole-5-yl)-8-methyl-1,3-dioxolo[4,5-f]quinoline-7-carboxylate

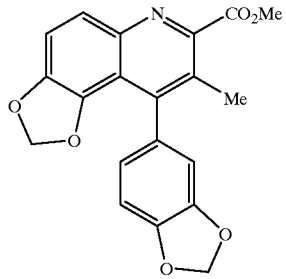

5-Amino-1,3-benzodioxole-4-yl 1,3-benzodioxole-4-yl ketone (2.7 g) and 2-ketobutyric acid methyl ester (1.9 g) were dissolved in acetic acid (30 ml), followed by addition of sulfuric acid (0.3 ml). The mixture was refluxed for 1.5 hours and then concentrated under reduced pressure. Water was added to the residue, followed by extraction with ethyl acetate. The extract was washed with aqueous sodium hydrogen carbonate solution and water successively, dried over magnesium sulfate and concentrated under reduced pressure to yield the title compound as yellow crystals (2.6 g).

m.p.: 174–177° C.

NMR (CDCl$_3$) δ: 2.30(3H,s), 4.04(3H,s), 5.89(2H,m), 6.06(2H,m), 6.68(2H,m), 6.89(1H,d,J=8 Hz), 7.36(1H,d,J=9 Hz), 7.81(1H,d,J=9 Hz).

Elemental Analysis for C$_{19}$H$_{13}$NO$_6$

Calcd: C, 64.96%; H, 3.73%: N, 3.99%
Found: C, 65.02%; H, 3.90%; N, 3.92%

(b) 9-(1,3-Benzodioxole-5-yl)-8-methyl-1,3-dioxolo[4,5-f]quinoline-7-carboxylic acid

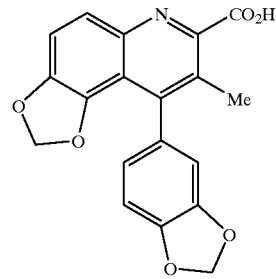

2.5% aqueous NaoH solution (20 ml) was added to a solution of 9-(1,3-benzodioxole-5-yl)-8-methyl-1,3-dioxolo[4,5-f]quinoline-7-carboxylic acid methyl ester in methanol (20 ml). The mixture was refluxed for one hour. 1N HCl was added to the reaction mixture to make it slightly acidic (pH 5), followed by extraction with ethyl acetate. The extract was washed with water, dried over magnesium sulfate and concentrated under reduced pressure to yield the title compound as yellow crystals (252 mg). Some portions of the compound were recrystalized from THF to be used for elemental and instrumental analysis.

m.p.: 219–222° C.

NMR (CDCl$_3$) δ: 2.59(3H,s), 5.93(2H,m), 6.07O2H,d, J=5 Hz), 6.67(2H,m), 6.90(1H,d,J=8 Hz), 7.43(1H,d,J=9 Hz), 7.76(1H,d,J=9 Hz).

Elemental Analysis for C$_{19}$H$_{13}$NO$_6$

Calcd: C, 64.96%; H, 3.73%; N, 3.99%
Found: C, 65.02%; H, 3.90%; N, 3.92%

REFERENCE EXAMPLE 15

10-(4-Trifluoromethoxyphenyl)-furo[3',4':6,7]naphtho[1,2-d]-1,3-dioxol-7(9 H)-one

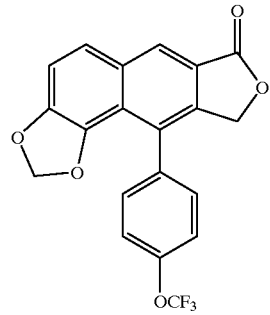

In the same manner as in Reference Example 1, the title compound was obtained.

Melting point: 222–225° C.

NMR (CDCl₃( δ: 5.19(2H,s), 5.92(2H,s), 7.25–7.45(5H, m), 7.73(1H,d,J=8.8 Hz), 8.46 (1H,s).

Elemental analysis for $C_{20}H_{11}F_3O_5$

Calcd: C, 61.86%; H, 2.86%
Found: C, 64.79%; H, 2.79%

REFERENCE EXAMPLE 16

9-(4-Trifluoromethoxyphenyl)-naphtho[1,2-d]-1,3-dioxol-7-carboxylic acid

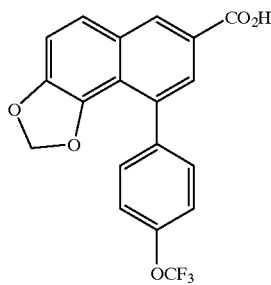

In the same manner as in Reference Example 9, the title compound was obtained.

Melting point: 296–300° C.

NMR (CDCl₃) δ: 5.94(2H,s), 6.82(2H,s), 7.20–7.90(4H, m), 8.58(1H,m).

IR (KBr): 2880, 1676, 1279 cm⁻¹

REFERENCE EXAMPLE 17

4-(1,3-Benzodioxol-5-yl)-6.7-diethoxy-naphtho[2,3-c]furan-1(3 H)-one

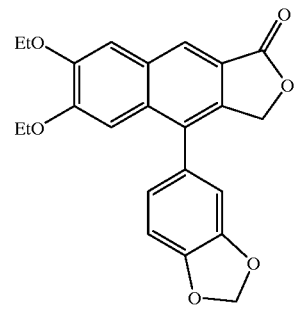

In the same manner as in Reference Example 6, the title compound was obtained.

NMR (CDCl₃) δ: 1.47(3H,t,J=7 Hz), 1.57(3H,t,J=7 Hz), 4.04(2H,q,J=7 Hz), 4.26(2H,q,J=7 Hz), 5.22(2H,s), 6.08 (1H,d,J=1.4 Hz), 6.12(1H,d,J=1.4 Hz), 6.80–6.90(2H,m), 6.99(1H,d,J=9 Hz), 7.09(1H,s), 7.30(1H,s), 8.28(1H,s).

REFERENCE EXAMPLE 18

10)-4-Trifluoromethoxyphenyl)-1,3-dioxolo[4,5-f]furo[3,4-b]quinolin-7(9 H)-one

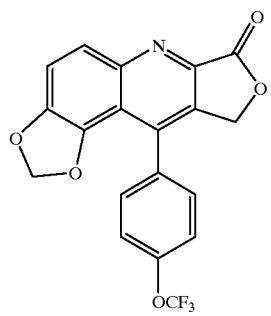

In the same manner as in Reference Example 6, the title compound was obtained.

NMR (CDCl₃) δ: 5.33(2H,s), 6.02(2H,s), 7.30–7.50(3H, m), 7.58(1H,d,J=9 Hz), 8.13(1H,d,J=9 Hz).

REFERENCE EXAMPLE 19

5-(1,3-Benzodioxol-5-yl)-7)-methoxyfuro[3,4-b]quinolin-2(4 H)-one

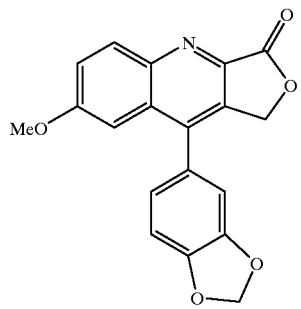

In the same manner as in Reference Example 6, the title compound was obtained.

NMR (CDCl$_3$) δ: 3.85(3H,s), 5.36(2H,s), 6.13(2H,s), 6.85–7.10(3H,m), 7.17(1H,d,J=3 Hz), 7.51(1H,dd,J=3,10 Hz), 8.32(1H,d,J=10 Hz).

Reference Example 20

8-(1,3-Benzodioxol-5-yl)-naphtho[2,3-d]-1,3-dioxole-6-carboxylic acid

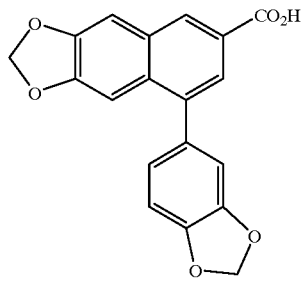

To a solution of 5-bromo-6-hydroxymethyl-1,3-benzodioxol (5.0 g) in ether (100 ml), butyl lithium (1.6M solution in hexane, 30 ml) was added dropwise at −78° C. After stirring at 0° C. for 1 hour, the solution was again cooled to −78° C.; a solution of 5-cyano-1,3-benzodioxol (3.52 g) in ether (50 ml) was added dropwise. After stirring at room temperature for 3 hours, water was added, followed by extraction with ethyl acetate. After being washed with brine, the organic layer was dried over magnesium sulfate and concentrated under reduced pressure. The residue was dissolved in toluene (100 ml); dimethyl fumarate (3.13 g) and trichloroacetic acid (0.83 g) were added. The mixture was refluxed for 1 hour and concentrated under reduced pressure. The residue obtained was dissolved in ethyl acetate and washed with a saturated aqueous solution of sodium hydrogen carbonate and brine. After being dried with magnesium sulfate, the mixture was concentrated under reduced pressure; the residue was purified by column chromatography (silica gel: 50 g, eluent: ethyl acetate–hexane=1:2) to yield a tetrahydro-1,4-epoxynaphthalene derivative (3.30 g) as a diastereomer mixture. This was dissolved in THF (15 ml) and methanol (15 ml); an aqueous solution (5 ml) of sodium hydroxide (1.24 g) was added, followed by overnight stirring. The reaction mixture was concentrated under reduced pressure and diluted with water, after which it was washed with ethyl acetate After concentrated hydrochloric acid was added to the water layer until the pH reached about 2, the product was extracted with ethyl acetate. The extract was washed with brine, after which it was dried over magnesium sulfate and concentrated under reduced pressure. The residue obtained was dissolved in ether (10 ml); concentrated hydrochloric acid (0.5 ml) was added; followed by stirring at room temperature for 3 hours. After the reaction mixture was concentrated under reduced pressure, water was added; the resulting precipitate was washed with methanol and ether to yield the title compound (0.38 g).

NMR (DMSO) δ: 6.10(2H,s), 6.12(2H,s), 6.80–7.10(4H, s), 7.42(1H,s), 7.81(1H,s), 8.35(1H,s).

REFERENCE EXAMPLE 21

6-Chloro-4-(4-chlorophenyl)naphtho[2,3-c]furan-1(3 H)-one

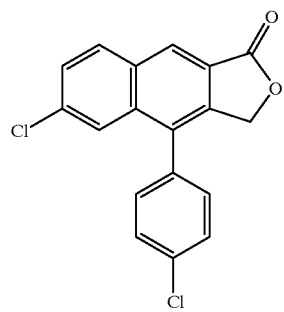

To a suspension of sodium borohydride (0.5 g) in dimethoxyethane (20 ml), a solution of 6-chloro-4-(4-chlorophenyl) naphtho[2,3-c]furan-1,3-dione (1.0 g) in THF (20 ml) was added dropwise, followed by stirring at room temperature for 1 hour. The reaction mixture was poured into 1N hydrochloric acid to stop the reaction; the product was extracted with ethyl acetate. After being washed with water, the extract was dried over magnesium sulfate and concentrated under reduced pressure. The residue obtained was purified by silica gel column chromatography (eluent: hexane–ethyl acetate=3:1) and recrystallized from THF to yield the title compound (300 mg).

m.p. 205–207° C.

NMR (CDCl$_3$) δ: 5.25(2H,s), 7.33(2H,d,J=8.4 Hz), 7.58 (3H,m), 7.72(1H,s), 8.05(1H,d,J=9.2 Hz), 8.51(1H,s).

IR (KBr): 1771, 1632, 1491 cm$^{-1}$

Elemental analysis for $C_{18}H_{10}Cl_2O_2$) Calcd: C, 65.68%; H, 3.06%. Found: C, 65.11%; H, 2.92%.

REFERENCE EXAMPLE 22

5-(4-Fluorophenyl)-3,4-dihydro-7-methoxy-1H-pyrano[3,4-b]quinolin-1-one (a) Ethyl 3-ethoxycarbonylmethyl-4-(4-fluorophenyl)-6-methoxyquinoline-2-carboxylate

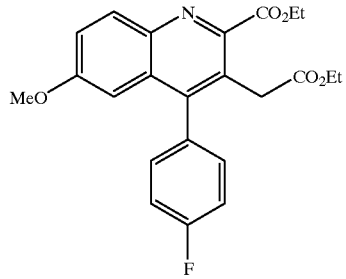

In the same manner as in Reference Example 14 (a), the title compound was obtained.

NMR (CDCl$_3$) δ: 1.21(3H,t, J=7.0 Hz), 1.46(3H,t,J=7.0 Hz), 3.71(3H,s), 3.85(2H,s), 4.11(2H,q,J=7.0 Hz), 4.51(2H, q,J=7.0 Hz), 6.54(1H,d,J=2.4 Hz), 7.25(4H,m), 7.39(1H,dd, J=7.6,2.4 Hz), 8.18(1H,d,J=9.6 Hz).

(b) 2-[4-(4-Fluorophenyl)-2-hydroxymethyl-6-methoxyquinolin-3-yl]-1-ethanol

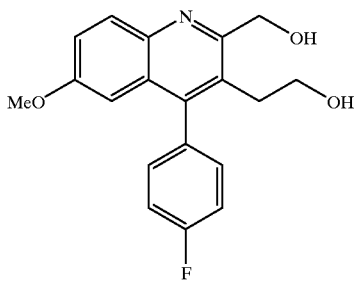

To a suspension of lithium aluminum hydride (180 mg) in THF (15 ml), ethyl 3-ethoxycarbonylmethyl-4-(4-fluorophenyl)-6-methoxyquinoline-2-carboxylate (1.0 g) was added, followed by stirring at 0° C. for 30 minutes. Water was added to the reaction mixture to stop the reaction; after the insoluble substances were filtered off, the product was extracted with ethyl acetate. After being washed with water, the extract was dried over magnesium sulfate and concentrated under reduced pressure to yield a crude crystal (1 g) of the title compound. The crude crystal obtained was used for the next reaction without further purification.

NMR (CDCl$_3$) δ: 2.79(2H,t,J=7.4 Hz), 3.62(2H,t,J=7.4 Hz), 3.69(3H,s), 4.97(2H,s), 6.51(1H,d,J=3.0 Hz), 7.27(4H, m), 7.33(1H,dd,J=9.0,3.0 Hz), 8.00(1H,d,J=9.0 Hz).

(c) 5-(4-Fluorophenyl)-3,4-dihydro-7-methoxy-1H-pyrano[3,4-b]quinolin-1-one

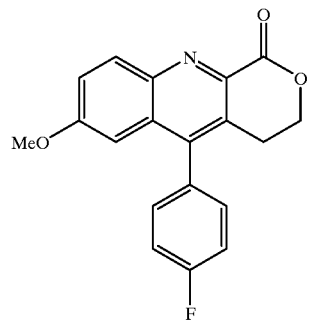

To a solution of a crude crystal (1.0 g) of 2-[4-(4-fluorophenyl)-2-hydroxymethyl-6-methoxyquinolin-3-yl]-1-ethanol in chloroform (100 ml), manganese dioxide (10 g) was added, followed by stirring at room temperature for 2 hours. After the manganese dioxide was filtered off, the reaction mixture was concentrated under reduced pressure; the residue obtained was recrystallized from THF to yield the title compound (335 mg).

m.p.: 240–241° C.

NMR (CDCl$_3$) δ: 2.99(2H,t,J=5.8 Hz), 3.76(3H,s), 4.54 (2H,t,J=5.8 Hz), 6.71(1H,d,J=3.0 Hz), 7.30(4H,m), 7.43(1H, dd,J=9.6,3.0 Hz), 8.31(1H,d,J=9.6 Hz).

IR (KBr): 2959, 2926, 1740, 1620, 1497 cm$^{-1}$

Elemental analysis for C$_{19}$H$_{14}$FNO$_3$ Calcd: C, 70.58%; H, 4.36%; N, 4.33%. Found: C, 70.49%; H, 4.57%; N, 4.26%.

REFERENCE EXAMPLE 23

11-(1,3-Benzodioxol-5-yl)-9,10-dihydro-7H-1,3-dioxolo[4,5-f]pyrano[3,4-b]quinolin-7-one (a) Ethyl 9-(1,3-benzodioxol-5-yl)-8-ethoxycarbonylmethyl-1,3-dioxolo[4,5-f]quinolin-7-carboxylate

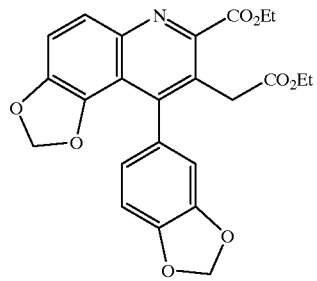

In the same manner as in Reference Example 14 (a), the title compound was obtained.

NMR (CDCl$_3$) δ: 1.21(3H,t,J=7.1 Hz), 1.44(3H,t,J=7.2 Hz), 3.86(2H,s), 4.12(2H,q,J=7.1 Hz), 4.49(2H,q,J=7.2 Hz), 5.89(2H,m), 6.06(2H,m), 6.68(1H,d,J=7.6 Hz), 6.72(1H,s), 6.86(1H,d,J=7.6 Hz), 7.41(4H,d,J=8.8 Hz), 7.89(1H,d,J=8.8 Hz).

(b) 2-[9-(1,3-Benzodioxol-5-yl)-7-hydroxymethyl-1,3-dioxolo[4,5-f]quinolin-8-yl]-1-ethanol

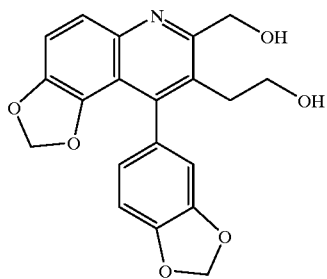

In the same manner as in Reference Example 22 (b), the title compound was obtained.

NMR (CDCl$_3$) δ: 1.76(1H,bs), 2.78(2H,t,J=7.4 Hz), 3.63 (2H,t,J=7.4 Hz), 4.92(2H,s), 5.24(1H,brs), 5.83(1H,d,J=1.4 Hz), 5.85(1H,d,J=1.4 Hz), 6.04(1H,d,J=1.4 Hz), 6.07(1H,d,J=1.4 Hz), 6.67(1H,dd,J=7.8,0.8 Hz), 6.70(1H,d,J=0.8 Hz), 6.87(1H,d,J=7.8 Hz), 7.32(1H,d,J=8.8 Hz), 7.67(1H,d,J=8.8 Hz).

(c) 11-(1,3-Benzodioxol-5-yl)-9,10-dihydro-7H-1,3-dioxolo[4,5-f]pyrano[3,4-b]quinolin-7-one

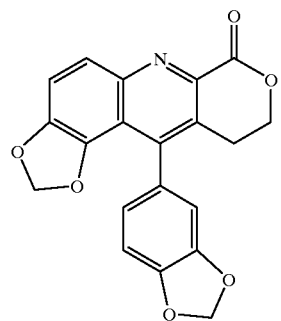

In the same manner as in Reference Example 22 (c), the title compound was obtained.

NMR (CDCl$_3$) δ: 3.00(2H,dt,J=1.8,5.9 Hz), 4.51(2H,t,J=5.9 Hz), 5.95(1H,d,J=1.4 Hz), 5.97(1H,d,J=1.4 Hz), 6.06 (1H,d,J=1.4 Hz), 6.09(1H,d,J=1.4 Hz), 6.65–6.80(2H,m), 6.91(1H,d,J=7.6 Hz), 7.47(1H,d,J=8.8 Hz), 8.05(1H,d,J=8.8 Hz).

REFERENCE EXAMPLE 24

6-Chloro-4-(4-pyridyl)-2-quinolinecarboxylic acid (a) Ethyl 6-chloro-4-(4-pyridyl)-2-quinolinecarboxylate

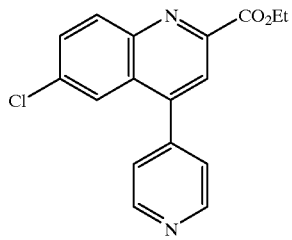

In the same manner as in Reference Example 14 (a), the title compound was obtained.

NMR (CDCl$_3$) δ: 1.50(3H,t,J=7.0 Hz), 4.58(2H,q,J=7.0 Hz), 7.46(2H,dd,J=4.4,1.8 Hz), 7.73–7.85(2H,m), 8.15(1H,s), 8.35(1H,d,J=8.8 Hz), 8.85(2H,dd,J=4.4,1.4 Hz).

Elemental analysis for C$_{17}$H$_{13}$N$_2$O$_2$Cl Calcd: C, 65.29%; H, 4.19%; N, 8.96%. Found: C, 65.01%; H, 4.12%; N, 8.98%.

(b) 6-Chloro-4-(4-pyridyl)-2-quinolinecarboxylic acid

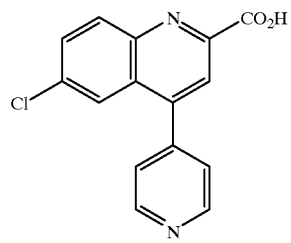

In the same manner as in Reference Example 14 (b), the title compound was obtained.

NMR (CDCl$_3$) δ: 3.36(1H,brs,COOH), 7.66(2H,d,J=5.8 Hz), 7.82(1H,d,J=2.2 Hz), 7.95(1H,dd,J=8.8,2.2 Hz), 8.06 (1H,s), 8.29(1H,d,J=8.8 Hz), 8.82(2H,d,J=5.8 Hz).

Elemental analysis for C$_{15}$H$_9$N$_2$O$_2$Cl.0.1H$_2$O Calcd: C, 62.88%; H, 3.24%; N, 9.78%. Found: C, 62.72%; H, 3.34%; N, 9.75%.

REFERENCE EXAMPLE 25

9-(4-Methoxyphenyl)-1,3-dioxolo[4,5-f]quinoline-7-carboxylic acid (a) Ethyl 9-(4-methoxyphenyl)-1,3-dioxolo[4,5-f]quinoline-7-carboxylate

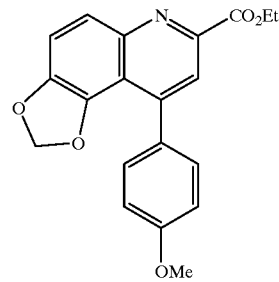

In the same manner as in Reference Example 14 (a), the title compound was obtained.

NMR (CDCl$_3$) δ: 1.43(3H,t,J=2.7 Hz), 3.90(3H,s), 4.54 (2H,q,J=7.2 Hz), 6.02(2H,s), 6.99(2H,d,J=8.8 Hz), 7.43(2H,d,J=8.8 Hz), 7.48(1H,d,J=8.8 Hz), 7.96(1H,s), 8.03(1H,d,J=8.8 Hz).

(b) 9-(4-Methoxyphenyl)-1,3-dioxolo[4,5-f]
quinoline-7-carboxylic acid

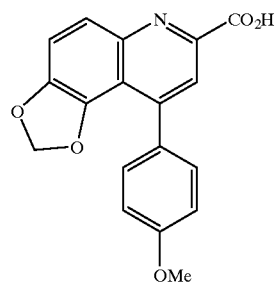

In the same manner as in Reference Example 14 (b), the title compound was obtained.

NMR (CDCl$_3$) δ: 3.83(3H,s), 6.09(2H,s), 7.02(2H,d,J=8.6 Hz), 7.48(2H,d,J=8.6 Hz), 7.70(1H,d,J=8.8 Hz), 7.77(1H,s), 7.87(1H,d,J=8.8 Hz).

REFERENCE EXAMPLE 26

9-(1,3-Benzodioxol-5-yl)-1,3-dioxolo[4,5-f]
quinoline-7-carboxylic acid (a) Ethyl 9-(1,3-benzodioxol-5-yl)-1,3-dioxolo[4,5-f]quinoline-7-carboxylate

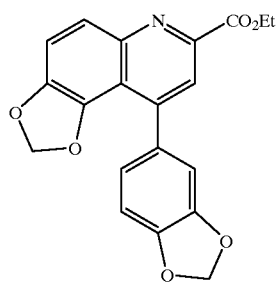

In the same manner as in Reference Example 14 (a), the title compound was obtained.

NMR (CDCl$_3$) δ: 1.48(3H,t,J=7.2 Hz), 4.54(2H,q,J=7.2 Hz), 6.04(2H,s), 6.06(2H,s), 6.87–7.00(3H,m), 7.48(1H,d,J=9.0 Hz), 7.96(1H,s), 8.03(1H,d,J=9.0 Hz).

(b) 9-(1,3-Benzodioxol-5-yl)-1,3-dioxolo[4,5-f]
quinoline-7-carboxylic acid

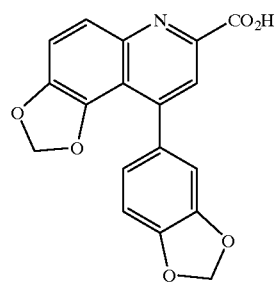

In the same manner as in Reference Example 14 (b), the title compound was obtained.

NMR (CDCl$_3$+DMSO-d$_6$) δ: 6.06(4H,s), 6.87–7.00(3H,m), 7.50(1H,d,J=9.2 Hz), 7.97(1H,d,J=9.2 Hz), 8.00(1H,s).

REFERENCE EXAMPLE 27

9-(4-Fluorophenyl)-1,3-dioxolo[4,5-f]quinoline-7-carboxylic acid (a) Ethyl 9-(4-fluorophenyl)-1,3-dioxolo[4,5-f]
quinoline-7-carboxylate

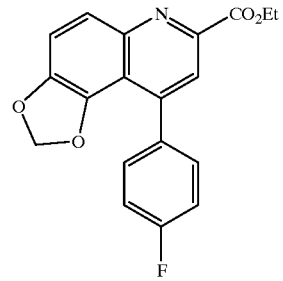

In the same manner as in Reference Example 14 (a), the title compound was obtained.

NMR (DMSO-d$_6$) δ: 1.38(3H,t,J=7.4 Hz), 4.43(2H,q,J=7.4 Hz), 6.11(2H,s), 7.26–7.37(2H,m), 7.57–7.62(2H,m), 7.74(1H,d,J=8.8 Hz), 7.81(1H,s), 7.93(1H,d,J=8.8 Hz).

(b) 9-(4-Fluorophenyl)-1,3-dioxolo[4,5-f]quinoline-7-carboxylic acid

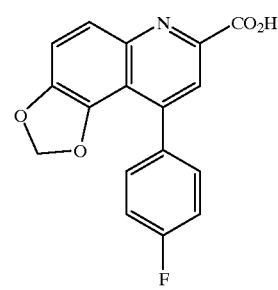

In the same manner as in Reference Example 14 (b), the title compound was obtained.

NMR (CDCl$_3$+DMSO-d$_6$) δ: 6.03(2H,s), 7.05–7.20(2H,m), 7.35–7.55(3H,m), 7.95–8.05(2H,m).

REFERENCE EXAMPLE 28

Methyl 3-bromomethyl-6-methoxy-4-(4-methoxyphenyl)quinoline-2-carboxylate (a) Methyl 6-methoxy-4-(4-methoxyphenyl)-3-methylquinoline-2-carboxylate

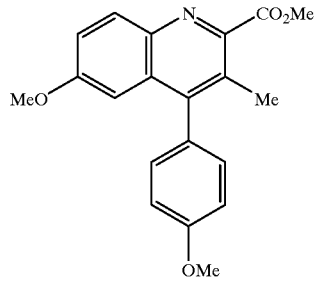

In the same manner as in Reference Example 14 (a), the title compound was obtained.

NMR (CDCl$_3$) δ: 2.35(3H,s), 3.71(3H,s), 3.92(3H,s), 4.05(3H,s), 6.66(1H,d,J=3 Hz), 7.00–7.25 (4H,m), 7.33(1H, dd,J=3.9 Hz), 8.09(1H,d,J=9 Hz).

(b) Methyl 3-bromomethyl-6-methoxy-4-(4-methoxyphenyl)quinoline-2-carboxylate

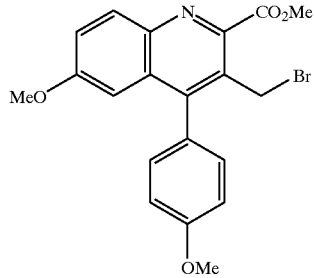

Methyl 6-methoxy-4-(4-methoxyphenyl)-3-methylquinoline-2-carboxylate (8.27 g) was dissolved in benzene (100 ml); N-bromosuccinimide (5.24 g) and 2,2'-azobis(isobutyronitrile) (0.40 g) were added; followed by refluxing for 2 hours. After cooling to room temperature, the resulting precipitate was filtered off. The filtrate was diluted with ethyl acetate (100 ml), after which it was washed with 1 N sodium hydroxide and brine successively, and dried over magnesium sulfate. The solvent was distilled off under reduced pressure; the residue obtained was purified by column chromatography (silica gel: 50 g, eluent: ethyl acetate-hexane=1:2). The crude crystal obtained was recrystallized from ethyl acetate-hexane to yield the title compound (9.93 g) as a colorless needle crystal.

NMR (CDCl$_3$) δ: 3.72(3H,s), 3.94(3H,s), 4.10(3H,s), 4.84(2H,s), 6.66(1H,d,J=3 Hz), 7.05–7.35(4H,m), 7.40(1H, dd,J=3.9 Hz), 8.14(1H,d,J=9 Hz).

REFERENCE EXAMPLE 29

Ethyl 8-chloro-1,3-dioxolo[4,5-g]quinoline-6-carboxylate

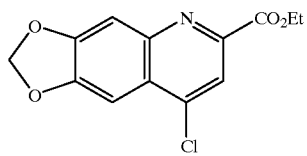

After a mixture of 3,4-(methylenedioxy)aniline (10 g), acetylenedicarboxylic acid diethyl ester (15 g) and ethyl alcohol (150 ml) was refluxed for 20 hours, the solvent was distilled off under reduced pressure. To the residue, diphenyl ether (50 ml) was added, followed by heating at 200° C. for 1.5 hours. After cooling, the reaction mixture was diluted with isopropyl ether to yield 3-hydroxy-1,3-dioxolo[4,5-g] quinoline-6-carboxylic acid ethyl ester as a brown crystal (10.6 g). After a mixture of the crystal obtained (10.4 g), phosphoryl chloride (22.4 ml) and benzene (170 ml) was stirred at room temperature for 3 days, the reaction mixture was poured into water and stirred at room temperature for 30 minutes. After this mixture was extracted with ethyl acetate, the extract was washed with brine and dried over magnesium sulfate; the solvent was distilled off under reduced pressure to yield the title compound as a brown crystal (8.59 g).

NMR (CDCl$_3$) δ: 1.48(3H,t,J=7.1 Hz), 4.53(2H,q,J=7.1 Hz), 6.20(2H,s), 7.52(1H,s), 7.58(1H,s), 8.13(1H,s).

REFERENCE EXAMPLE 30

Ethyl 8-(1-piperidinyl)-1,3-dioxolo[4,5-g]quinoline-6-carboxylate

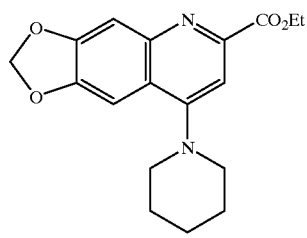

A mixture of ethyl 8-chloro-1,3-dioxolo[4,5-g]quinoline-6-carboxylate (300 mg) as obtained in Reference Example 29, piperidine (0.5 ml) and ethyl alcohol (5 ml) was heated at 140° C. in a sealed tube for 17 hours. After the solvent was distilled off under reduced pressure, the residue was purified by column chromatography using silica gel (hexane-ethyl acetate=3:1) to yield the title compound as a colorless crystal (73.6 mg).

NMR (CDCl$_3$) δ: 1.47(3H,t,J=7.1 Hz), 1.71(2H,m), 1.84 (4H,m), 3.15(4H,m), 4.52(2H,q,J=7.1 Hz), 6.12(2H,s), 7.29 (1H,s), 7.51(1H,s), 7.60(1H,s).

REFERENCE EXAMPLE 31

Ethyl 8-(1-pyrrolidinyl)-1,3-dioxolo[4,5-g] quinoline-6-carboxylate

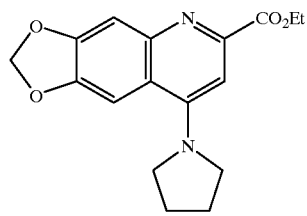

In the same manner as in Reference Example 30, the title compound was obtained.

NMR (CDCl$_3$) δ: 1.46(3H,t,J=7.1 Hz), 2.05(4H,m), 3.66 (4H,m), 4.50(2H,q,J=7.1 Hz), 6.08(2H,s), 7.29(1H,s), 7.46 (1H,s), 7.51(1H,s).

REFERENCE EXAMPLE 32

Ethyl 8-(4-morpholinyl)-1,3-dioxolo[4,5-g] quinoline-6-carboxylate

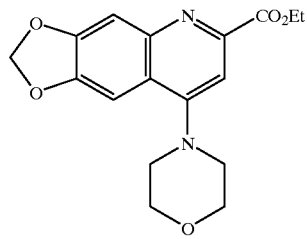

In the same manner as in Reference Example 30, the title compound was obtained.

NMR (CDCl$_3$) δ: 1.48(3H,t,J=7.2 Hz), 3.20(4H,m), 3.98 (4H,m), 4.53(2H,q,J=7.2 Hz), 6.14(2H,s), 7.31(1H,s), 7.54 (1H,s), 7.63(1H,s).

REFERENCE EXAMPLE 33

Ethyl 8-(4-methylpiperazin-1-yl)-1,3-dioxolo[4,5-g]quinoline-6-carboxylate

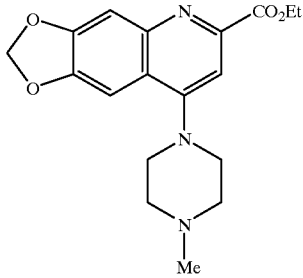

In the same manner as in Reference Example 30, the title compound was obtained.

NMR (CDCl$_3$) δ: 1.47(3H,t,J=7.0 Hz), 2.42(3H,s), 2.71 (4H,m), 3.24(4H,m), 4.53(2H,q,J=7.2 Hz), 6.13(2H,s), 7.30 (1H,s), 7.53(1H,s), 7.62(1H,s).

EXAMPLE 1

N-Methyl-9-(1,3-benzodioxole-5-yl)-8-hydroxymethylnaphtho[1,2-d]-1,3-dioxole-7-carboxamide

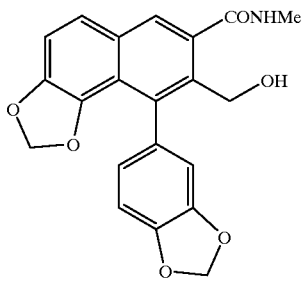

Helioxanthin (1.0 g) was suspended in benzene (10 ml), followed by addition of methylamine (40% methanol solution: 2 ml). The mixture was heated at 120° C. under stirring for 4 days. The reaction mixture was concentrated under reduced pressure. The resulting residue was recrystalized from DMF to yield the title compound (144 mg).

m.p.: 233–235° C.

NMR (DMSO-d$_6$) δ: 2.83(3H,d,J=5 Hz), 4.27(2H,d,J=6 Hz), 4.95(1H,t,J=6 Hz), 5.85(1H,s), 5.85(1H,s), 6.06(1H,s), 6.12(1H,s), 6.70(1H,dd,J=1.6 Hz,8 Hz), 6.81(1H,d,J=1.6 Hz), 6.93(1H,d,J=8 Hz), 7.37(1H,d,J=9 Hz), 7.63(1H,d,J=9 Hz), 8.01(1H,s), 8.55–8.70(1H,m).

IR(KBr): 3340, 1615, 1485, 1445, 1435, 1280, 1065 cm$^{-1}$

Elemental Analysis for $C_{21}H_{17}NO_6 \cdot 0.2H_2O$ Calcd: C, 63.47%; H, 4.82%; N, 3.52%. Found: C, 63.50%; H, 4.61%; N, 3.81%.

EXAMPLE 2

N-Methyl-9-(4-methoxyphenyl)-8-hydroxymethyl-naphtho[1,2-d]-1,3-dioxole-7-carboxamide

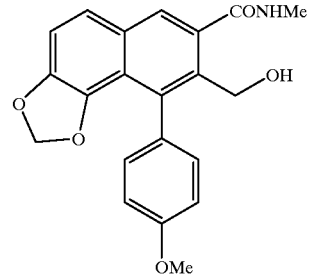

The title compound was produced in a similar manner to that in Example 1, using 10-(4-methoxyphenyl)furo[3',4':6,7]naphtho[1,2-d]-1,3-dioxole-7(9H)-one m.p.: 187–190° C.

NMR (CDCl$_3$) δ: 3.07(3H,d,J=5 Hz), 3.88(3H,s), 4.37 (2H,s), 5.79(2H,s), 6.56(1H,brs), 6.93(2H,d,J=8 Hz), 7.19 (1H,d,J=9 Hz), 7.23(2H,d,J=8 Hz), 7.44(1H,d,J=9 Hz), 7.93 (1H,s).

Elemental Analysis for $C_{21}H_{19}NO_5$ Calcd: C, 69.03%; H, 5.24%; N, 3.83%. Found: C, 68.92%; H, 5.27%; N, 3.77%.

EXAMPLE 3

N-Methyl-9-(4-chlorophenyl)-8-hydroxymethyl-naphtho[1,2-d]-1,3-dioxole-7-carboxamide

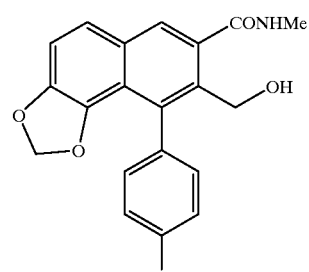

The title compound was produced in a similar manner to that in Example 1, using 10-(4-chlorophenyl)furo[3',4':6,7]naphtho[1,2-d]-1,3-dioxole-7(9H)-one which was obtained in Reference Example 2.

m.p.: 202–204° C.

NMR (CDCl$_3$) δ: 3.08(3H,d,J=5 Hz), 4.35(3H,m), 5.80 (2H,s), 6.42(1H,brs), 7.26(3H,m), 7.38(2H,d,J=8 Hz), 7.46 (12H,d,J=8 Hz), 7.96(1H,s).

Elemental Analysis for $C_{20}H_{16}ClNO_4$ Calcd: C, 64.96%; H, 4.36%; N, 3.79%. Found: C, 64.94%; H, 4.62%; N, 3.85%.

EXAMPLE 4

N-Methyl-9-(2-naphthyl)-8-hydroxymethyl-naphtho[1,2-d]-1,3-dioxole-7-carboxamide

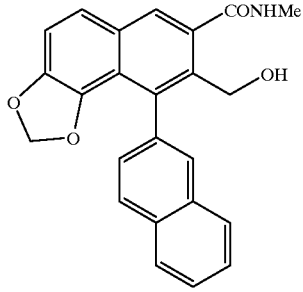

The title compound was produced in a similar manner to that in Example 1, using 10-(2-naphthyl)furo[3',4':6,7]naphtho[1,2-d]-1,3-dioxole-7(9H)-one which was obtained in Reference Example 3.

m.p.: 207–210° C.

NMR (CDCl$_3$) δ: 3.07(3H,d,J=5 Hz), 4.36(3H,m), 5.64 (2H,m), 6.56(1H,brs), 7.22(1H,m), 7.49(4H,m), 7.84(4H, m), 7.99(1H,s).

Elemental Analysis for C$_{24}$H$_{19}$NO$_4$ Calcd: C, 74.79%; H, 4.97%; N, 3.63%. Found: C, 74.28%; H, 5.21%; N, 3.60%.

EXAMPLE 5

N-Methyl-9-(4-fluorophenyl)-8-hydroxymethyl-naphtho[1,2-d]-1,3-dioxole-7-carboxamide PCS-TEXT

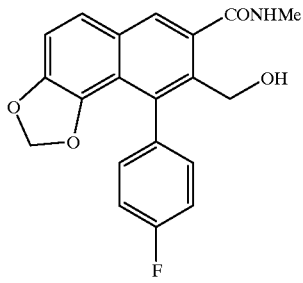

The title compound was produced in a similar manner to that in Example 1, using 10-(4-fluorophenyl)- furo[3',4':6,7]naphtho[1,2,-d]-1,3-dioxol-7(9H)-one which was obtained in Reference Example 4.

m.p: 210–213° C.

NMR (CDCl$_3$) δ: 3:08(3H,d,J=5 Hz), 4.36(3H, m) 5.79 (2H,s), 6.48(1H,brs), 7.09(2H,t,J=9 Hz), 7.27(3H,m), 7.46 (1H,d,J=8 Hz), 7.95(1H,s).

Elemental Analysi for C$_{20}$H$_{16}$FNO$_4$ Calcd: C, 67.98%; H, 4.56%; N, 3.96% Found: C, 67.90%; H, 4.75%; N, 3.94%

EXAMPLE 6

N-Methyl-9-(4-methylphenyl)-8-hydroxymethyl-naphtho[1,2-d]-1,3-dioxole-7-carboxamide

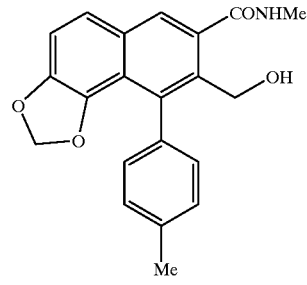

The title compound was produced in a similar manner to that in Example 1, using 10-(4-methoxphenyl)-furo [3',4':6,7]naphtho [1,2-d]-1,3-dioxol-7(9H)- one which was obtained in Reference Example 5.

m.p.: 210–212° c.

NMR (CDCl$_3$) δ: 2.43(3H, s), 3.07(3H,d,J=5 Hz), 4.20–4.40 (3H, m), 5.78 (2H,s), 6.51 (1H,brs), 7.20 (5H,m), 7.45 (2H,d,J=H,z), 7.05 (1H,s).

Elemental Analysis for C$_{21}$H$_{19}$NO4 Calcd: C, 72.19%; H, 5.48%; N, 4.01% Found: C, 71.85%; H, 5.79%; N, 3.94%

EXAMPLE 7

N-Methyl-(1,3- benzodioxole-5-yl)-7-hydroxymethyl-naphto[2,3-d]-1,3-dioxole-6-carboxamide

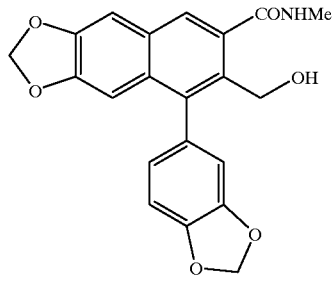

The title compound was produced in a similar manner to that in Example 1, using 9-(1,3-benzodioxole-5-yl) -furo[3', 4':6,7]naphtho[2,3-d]-1,3-dioxol-6(8H)-one (Justicidin E: K. Ohta., et al., Tetrahedron lett., 1970, 923).

m.p.: 222–224° C.

NMR (CDCl$_3$) 67 : 3:07(3H,d,J=5 Hz), 4.30–4.50(3H,m), 6.05(4H,m), 6.51(1H,brs), 6.77(3H,m), 9.94(1H,d,J=7 Hz), 7.11(1H,s), 7.83(1H,s).

Elemental Analysis for C$_{21}$H$_{17}$NO$_6$ Calcd: C, 66.49%, H, 4:52%; N, 3.69% Found: C, 66.35%, H, 4.73%; N, 3.61%

EXAMPLE 8

9(1,3-Benzodioxole-5-yl)-8hydroxymethyl-1,3-dioxolo[4,5-f]quinoline-7-carboxamide

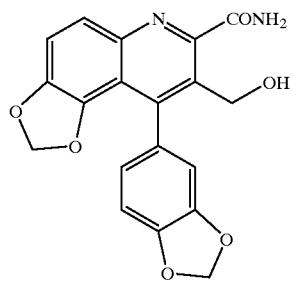

The title compound was produced in a similar manner to that in Example 1, using a 10-(1,3-benzodioxole-5-yl)-8,9-dihydro-9H-1,3-dioxolo[4,5-f]pyrolo[3,4-b]quinolin-7-one which was obtained in Reference Example 6.

NMR (CDCl$_3$) 67 : 4.50–4.75(2H,m) 5.02(1H,d,J=8 Hz), 5.72(1H,m), 5.91(1H,d,J=1.4 Hz), 5.93(1H,d,J=1.4 Hz), 6.08(1H,d,=1.2 Hz), 6.75–6.83(2H,m), 6.89(1H,d,J=8 Hz), 7.43(1H,d,J=9 Hz), 7.75(1H,d,J=9 Hz), 8.15(1H,m).

Elemental Analysis for C$_{19}$H$_{14}$N$_2$O$_6$ Calcd: C, 62.30%; H, 3.85%; N, 7.65% Found: C, 62.13%; H, 3.89%; N, 7.37%

EXAMPLE 9

N-methyl-(3-hydroxmethyl-6-methyl-4-phenylquinoline)-2-carboxamide

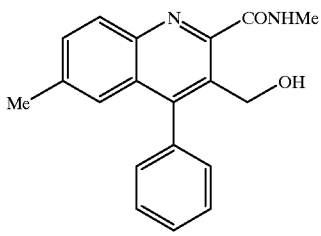

The title compound was produced in a similar manner to that in Example 1, using 5-phenyl-7-methyl-furo[3,4-b]quinolin-2(4H)-one which was obtained in Reference Example 7.

m.p.: 136–137° C.

NMR (CDCl$_3$) δ: 2.43(3H,s) 3.13(3H,d,J=5 Hz), 4.64(2H, d,J=8 Hz), 5.37(1H,d,J=8 Hz), 7.23(1H,brs,) 7.30–7.40(2H, m), 7.48–7.52(4H,m), 7.98(1H,d,J=8 Hz), 8.44(1H,m).

IR(KDr): 3460, 3398, 1652, 1533, 1488, 1421, 1025 cm$^{-1}$

Elemental Analysis for C$_{19}$H$_{18}$N$_2$O$_2$ Calcd: C, 74.49%; H, 5.92%; N, 9.14% Found: C, 74.28%; H, 5.95%; N, 9.20%

EXAMPLE 10

N-Methyl-[3-hydroxymethyl-6-methyl-4-(2,4-difluorophenyl) quinoline]-2-carboxamide

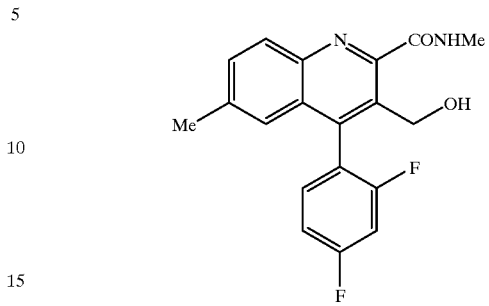

The title compoud was produced in a similar manner to that in Example 1, using 5-(2,4-diflurophenyl)-7-methyl-furo [3,4-b]quinolin-2(4H)-one which was obtained in Reference Example 8.

m.p.: 140–141° C.

NMR (CDCl$_3$) δ: 2.46(3H,s), 3.13(3H,dJ=5 Hz), 4.46(2H, dd,J=10Hz,13 Hz), 4.84(1H,dd,J=6Hz, 13 Hz), 5.38(1H,dd, J=6 Hz), 6.98–7.16(3H,m), 7.30–7.42(1H,m), 7.59(1H,dd, J=1.8Hz, 8 Hz), 8.02(1H,d,J=8 Hz), 8.42(1H,m).

IR(KBr): 3464, 3402, 1652, 1509, 1139, 1023, 969 cm$^{-1}$

Elemental Analysis for C$_{19}$H$_{16}$F$_2$N$_2$O$_2$ Calcd: C, 66.66%; H, 4.71%; N, 8.18% Found: C, 66.55%; H, 4.71%; N, 8.23%

EXAMPLE 11

9(4-Methoxyphenyl)-naphtho[1,2,-d]-1,3,-dioxole-7-carboxamide

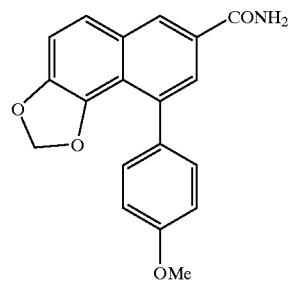

9-(4Methoxphenyl)-naphtho[1,2-d]-1,3-dioxole-7-carboxylic acid (200 mg), which was produced in Reference Example 9, was suspended in THF (6 ml), followed by addition of DMF (1 drop). Oxalyl chlordie (0.1 ml) was dropwise added to the resulting mixture at room temperature. The mixture was stirred at room temperature for one hour. The resulting reaction mixture was concentrated under reduced pressure to yield crude 9-(4-methoxphenyl)-naphtho[1,2-d]-1,3-dioxole-7carboxy chloride. A solution of the above produced acid chloride in THF (3 ml) was dropwise added to a mixture of a conc. aquous ammonia solution (2 ml) and THF (1 ml) under ice-cooling. After being stirred for 30 minutes, the reaction mixture was extracted by ethyl acetate. The extract was washed with bring, dried over magnesium sulfate and concentrated under reduced pressure. The resulting residue was recrystalized from ethanol to yield the tile compound (134 mg).

m.p.: 187–189° C.

NMR (CDCl₃) δ: 3.89(3H,s), 6.90–7.00(2H,m), 7.28(1H, d,J=8 Hz), 7.33–7.41(2H,m), 7.61(1H,d,J=1.6 Hz), 7.62(1H, d,J=8 Hz), 8.31(1H,d,J=6 Hz).

IR(KBr): 3365, 3168, 1681, 1666, 1459, 1288, 1245, 1052 cm⁻¹

Elemental Analysis for $C_{19}H_{15}NO_4$ Calcd: C, 71.02%; H, 4.71%; N,4.36% Found: C, 70.77%; H, 4.71%; N, 4.47

EXAMPLE 12

9-(4-Trifluromethylphenyl)-naphto[1,2-d]-1,3-dixole-7-carboxamide

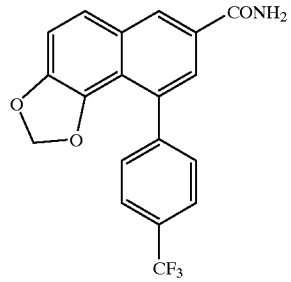

The title compound was produced in a similar manner to that in Example 11, using 9-(4-trifluromethylphenyl)-naphtho[1,2,-d]-1,3-dioxole-7-carboxylic acid which was produced in Reference Example 10.

m.p.: 207–209° C.

NMR (CDCl₃) δ: 5.90(2H,brs), 5.94(2H,s), 7.31(1H,d, J=8 Hz), 7.57(2H,brs,J=8 Hz), 7.64(1H,d,J=8 Hz), 7.65(1H, d,J=8 Hz), 7.67(2H,d,J=8 Hz), 8.34(1H,d,J=8 Hz).

IR(KBr): 3487, 3147, 1685, 1463, 1328, 1293, 1108, 1072 cm⁻¹

Elemental Analysis for $C_{19}H_{12}F_3NO_3$ Calcd: C, 63.51%; H, 3.37%; N, 3.90% Found: C, 63.21%; H, 3.63%; N, 4.02%

EXAMPLE 13

9-(1,3-Benzodioxole-5-yl)-6-methyl-naphto[1,2-d]-1,3-dioxole-7-carboxamide

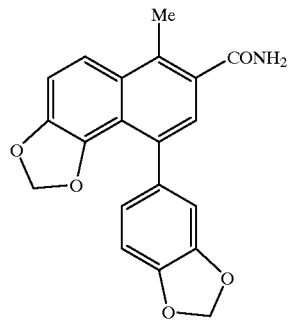

The title compound was produced in a similar manner to that in Example 11, using 9-(1,3-benzodioxole-5-yl)-6-methyl-naphto [1,2-d]-1,3,-dioxole-7carboxylic acid.

m.p.: 237–239° C.

NMR(DMSO-d₆) δ: 2.67(3H,brs), 5.98(2H,brs), 6.07(2H, brs), 6.82–7.00(3H,m), 7.15(1H,brs), 7.44(1H,d,J=9 Hz), 7.52(1H,brs), 7.80(1H,brs.), 7.85(1H,brs).

IR(KBr): 3398, 3178,1648, 1615, 1492, 1378, 1251, 1054 cm⁻¹

Elemental Analysis for $C_{20}H_{15}NO_5$ Calcd: C, 68.76%; H, 4.33%; N, 4.01% Found: c, 68.40%; H, 4.31%; N, 4.05%

EXAMPLE 14

9-(1,3-Benzodioxole-5-yl)-naphtho[1,2-d]-1,3-dioxole-7-carboxamide

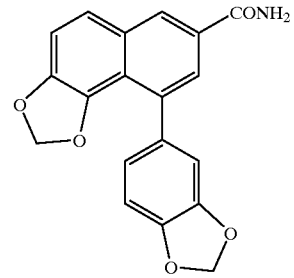

The title compound was produced in a similar manner to that in Example 11, using 9-(1,3-benzodioxole-5-yl)-naphtho [1,2-d]-1,3-dioxole-7-carboxylic acid which was prepared in Reference Example 12.

m.p.: 267–269° C.

NMR (DMSO-d₆) δ: 6:01(2H,s), 7.08(2H,s), 6.90(1H,dd, J=1.4Hz,8 Hz), 6.97(1H,d,J=8 Hz), 7.01(1H,d,J=1.4 Hz), 7.43(1H,brs), 7.44(1H,d,J=9 Hz), 7.72(1H,d,J=1.6 Hz), 7.73 (1H,d,J=9 Hz), 8.12(1H,brs), 8.46(1H,d,J=1.6 Hz).

IR(KBr): 3460, 1677, 1486, 1465, 1280, 1233, 1052 cm⁻¹

Elemental Analysis for $C_{19}H_{13}NO_5$ Calcd: C, 68.06%; H, 3.91%; N, 4.18% Found: C, 67.81%; H, 3.91%; N, 4.17%

EXAMPLE 15

N-Methyl-9-(1,3-benzodioxole-5-yl)-naphtho;[1,2,-d]-1,3-dioxole-7-carboxamide

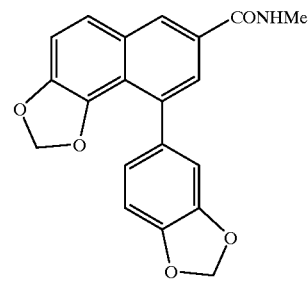

The title compund was produced in a similar manner to that in Example 11, using 9(1,3-benzodioxole-5yl)-naphtho [1,2,-d]-1,3-sioxole-7-carboxylic acid which was prepared in Reference Example 12 and conducting a condensation reaction with methylamine (40% methanol solution.

m.p.: 206–208° C.

NMR (CDCl₃) δ: 3.05(5 Hz), 5.96(2H,s), 6.03(2H,s), 6.23(1H,m), 6.80–6.93(3H,m), 7.26(1H,d,J=8z), 7.56(1H, J=1.8 Hz),7.58(1H,d,J=8 Hz), 8.24(1H,d,J=1.8 Hz).

IR(KBr): 1639, 1536, 1488, 1286, 1226,1058, 1037 cm⁻¹

Elemental analysis for $C_{20}H_{15}NO_5$ Calcd: C, 68.76%; H, 4.33%; N, 4.01% Found: C, 68.37%; H, 4.31%; N, 3.98%

EXAMPLE 16

N,N-Dimethyl-9-(1,3,-benzodioxole-5-yl)-naphtho[1,2-d]-1,3,-dioxole-7-carboxamide

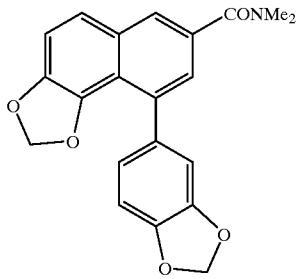

The title compound was produced in a similar manner to that in Example 11, using 9-(1,3-benzodioxole-5-yl)-naphtho [1,2-d]-1,3-dioxole-7-carboxylic acid which was prepared in Reference Example 12 and conductin a condensation reaction with dimethylamine (50% aqueous solution).

m.p.: 160–161° C.

NMR (CDCl$_3$) δ: 3.11(6H,brs), 5.95(2H,s) 6..02(2H,s), 6.80–6.93 (3H,m), 7.24(1H,d,J=8 Hz), 7.31(1H,d,J=1.6 Hz), 7.42(1H,d,J=8 Hz), 7.85(1H,d,J=1.6 Hz).

IR(KBr): 1629, 1496, 1486, 1280, 1232, 1031, 1039 cm$^{-1}$

Elemental analysis for C$_{21}$H$_{17}$NO$_5$ Calcd: C, 69.41%; H, 4.72%; N, 3/85% Found: C, 68.99%; H, 4.73%; N, 3.86%

EXAMPLE 17

Ethyl 2-[9-(1,3-benzodioxole-5-yl)-naphtho[1,2-d]-1,3-dioxole-7-carboxamido ]acetate

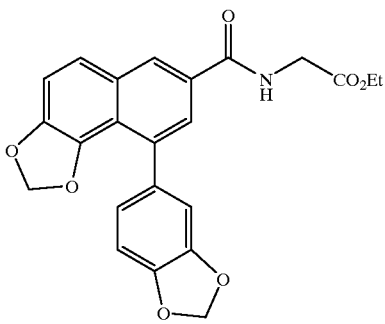

9-(1,3-Benzodioxole-5-yl)-naphtho[1,2-d]-1,3-dioxole-7-carboxylic acid (200 mg) which was prepared in Reference Example 12 was suspended in THF (6 ml), followed by addition of DMF (1drop). Oxalyl chloride (0.1 ) was dropwise added to the resulting mixture at room temperature, followed by being stirred for 1 hour. the resulting reaction mixuture was concentrated under reduced pressure to yield crude 9-(1,3-benzoxole-5-yl)-naphtho[1,2-d]1,3-dioxole-7-carboxyl chloride. Sodium hydrogencarbonate (150 mg) was dissolved in water (1 ml), followed by addition of glycine ester hydrochloride (91 mg) and THF (2 ml). To the resulting mixture was added dropwise a solution of the avove acide chlordie in THF under ice-cooling. After being stirred for one hour, the resulting mixture was extracted with ethyl acetate. The extract was washed with brine an 1N hydrochloric acid and dried over magnesium sulfate and concentrated under reduced pressure. The resulting residue was recrystalized from methanol to yield the title compound (213 mg).

m.p.P 171–173° C.

NMR (CDCl$_3$) δ: 1.33(3H,t,J=7 Hz), 4.28(2H,q,J7 Hz), 4.29(2H,d,J=5 Hz), 5.97(2H,s), 6.03(2H,s), 6.76(1H,m), 6.82–6.93(3H,m), 7.25(1H,d,J=9 Hz), 7.60(1H,d,J=9 Hz), 7.62(1H,d,J=1.8 Hz), 8.28(1H,d,J=8 Hz).

IR(KBr): 1745, 1664, 1527, 1280, 1236, 1214, 1203 cm$^{-1}$

Elemental Analysis for C$_{23}$H$_{19}$N)$_7$ Calcd: C, 65.56%; H, 4.54%; N, 3.32% Found: C, 65.19%; H, 4.59%; N, 3.31%

EXAMPLE 18

2-[9-(1,3-Benzodioxole-5yl)-naphtho[1,2-d]-1,3-dioxole-7-carboxamido]acetic acid

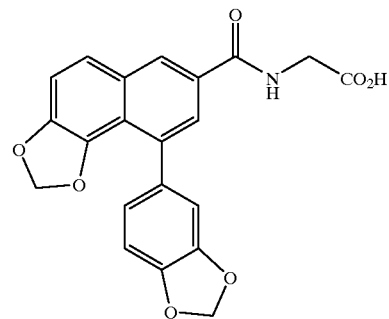

Ethyl 2-[9-(1,3,-benzodioxole-5yl)-naphtho[1,2-d]-1,3-dioxole-7-carboxamido]acetate (200 mg), which was produced in Example 17, was dissolved in THF (10 ) and methanol (5 ml), followed by addition of a 1N aqueous solution of NaOH. The resulting mixture was stirred at room temperature for 2 hours. After the mixture was concentrated under reduced pressure, the residure was dissolved in water. The resulting aqueous solution was washed with ether. To the mixture was added in 1N HCl until it pH reached to about 2, followed by extraction with ethyl acetate. The extract was washed with brine, dried over magnesium sulfate and concentrated under reduced pressure. The resulting residue was recrystalized from methanol to yield the title compound (163 mg).

m.p.: 255–257° C.

NMR (CDCl$_3$) δ: 4.29(2H,d,J=5 Hz), 5.94(2H,s), 6.01 (2H,s), 6.68–7.00(4H,m), 7.22(1H,d,J=9 Hz), 7.55(1H,d,J=9 Hz), 7.59(1H,brs), 8.25(1H,brs).

IR(KBr): 1720, 1625, 1529, 1429, 1282, 1235, 1056 cm$^{-1}$

Elemental Analysis for C$_{23}$H$_{15}$NO$_7$. 1.5H$_2$O Calcd: C, 62.16%; H, 4.08%; N, 3.15% Found: C, 62.22%; H, 4.24%; N, 3.37%

EXAMPLE 19

N-(3-Dimethylaminopropyl)-9-(1,3-benzodioxole-5-yl)-naphtho [1,2-d]-1,3-dioxole-7-carboxamide hydrochloride

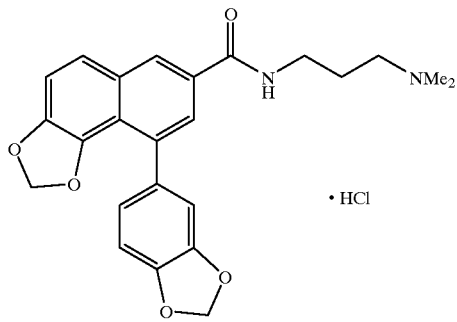

9-(1,3,-Benzodioxole-5-yl)-naphtho[1,2,-d]-1,3,-dioxole-7-carboxylic acid (200 mg), which was prepared in Reference Example 12, was suspended in THF (6 ml), followed by addition of DMF (1 drop). Oxalychlordie (0.1 ml) was added dropwise to the mixture. The resulting mixture was stirred for one hour and concentrated under reduced pressure to yield crude naphthalene-7-carboxyl cholride.

A solution of the above produced acide chloride in THF (6 ml) was added dropwise to a solution of N,N-dimethylpropylenediamine (0.16 ml) in THF (2 ml). The mixture was stirred for 1 hour and, after addition of water, extracted with ethyl acetate. The extract was washed with brine, dried over magnesium sulfate and concentrated under reduced pressure. The residue was purified with column chromatography (silica-gel 10 g. eluent:chloroform-menthanol-aqueous ammonia=20:1:0.1 ) to yield its free amine (about 240 mg.). This was dissolved in ethyl acetate (2 ml), followed by addition of 4N HCl-ethyl acetate (0.2 ml). The resulting precipitates were collected by suction and recrystalized from ethanol to yield the title compound (166 mg).

m.p.: 233–240 ° C.

NMR (DMSO-$d_6$) δ: 1.84–2.02 (2H,m), 2.75(6H,s), 3.02–3.15(2H,m), 3.30–3.45(2H,m), 6.02(2H,s) 6.09(2H,s), 6.90(1H,dd,J=1.6Hz,8 Hz), 6.97(1H,dJ=8 Hz), 7.01(1H,d, J=1.6 Hz) 7.45(1H,d,J=9 Hz), 7.71(1H,d,J=1.8 Hz), 7.75 (1H,d,J=9 Hz), 8.45(1H,d,J=1.8 Hz), 8.82(1H,m).

IR(KBr): 1646,1535, 1488, 1291, 1232, 1038 cm$^{-1}$

Elemental Analysis for $C_{24}H_{25}ClN_2O_5$ Calcd: C, 63.09%; H, 5.51%; N, 6.13% Found: C, 62/85%; H, 5.44%; N, 6.10%

EXAMPLE 20

N-(3-Dimethylaminoethyl)-9-(1,3-benzodioxole-5yl)-naptho [1,2-d]-1,3,-dioxole-7-carboxamide hydrochloride

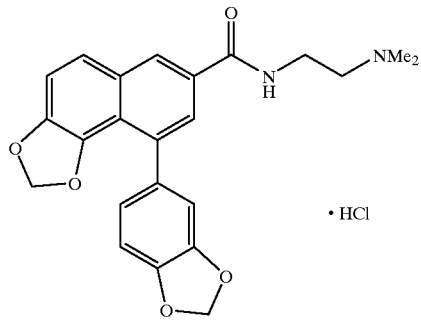

The title compound was produced in a similar manner to that in Example 19, using 9-(1,3-benzodioxole-5-yl)-naphtho [1,2-d]-1,3-dioxole-7-carboxylic acid which was prepared in Reference Example 12 and conducting a condensation reaction with N,N-dimethylethylenediamine.

m.p.: 245–250° c.

NMR (DMSO-$d_6$) δ: 2.83(6H,s), 3.20–3.40(2H,m), 3.55–3.75(2H,m), 6.02(2H,s), 6.09(2H,s), 6.09(2H,s), 6.90 (1H,dd,J=1.4HZ,8hz), 6.98(1H,d,J=8 Hz), 7.01(1H,d,J=1.4 Hz), 7.47(1H,d,J=1.6 Hz), 8.91(1H,m).

IR(KRr): 1648, 1544, 1500, 1488, 1288, 1232, 1039 cm$^{-1}$

Elemental Analysis for $C_{23}H_{23}ClN_2O_5$ Calcd: C, 62.37%; H, 5.23%; N, 6:33% Found: C, 62.12%; H, 5.20%; N, 6.41%

EXAMPLE 21

9-(1,3-Benzodioxole-5-yl)-8-methyl-naptho[1,2-d]-1,3,-dioxole-7-carboxamide

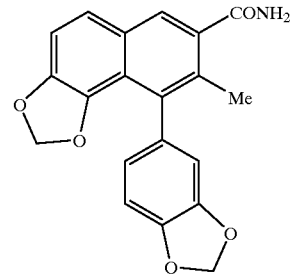

WSC[1-Ethyl-3-(3-dimethylaminopropyl) carbodimide hydrochloride](33 mg) and ammonia (3N ethanol solution:0.14 ml) were added under ice-cooling to a DMF solution of 9-(1,3-benzodioxole-5yl)-8-methyl-naphtho[1,2-d]-1,3,-dioxole-7-carboxylic acid (50 mg) which was prepared in Reference Example 13. The mixture was stirred at room temperature for 2 hours, and the reaction was stopped with addition of water. The residue was purified with column chromatography (Silica-Gel 5 g, eluent:ethyl acetate-hexane=1:1) and recrystalized from methanol to yield the title compound (23 g).

m.p.: 244–246° C.

NMR (CDCl$_3$) δ: 2.41(3H,s), 5.82(1H,d,J=1.6Hz), 5.83 (1H,d,J=1.6 Hz), 6.03(1H,dJ=1.4 Hz), 6.06(1H,d,J=1.4 Hz), 6.68 (1H,dd,J=1.6Hz,8 Hz), 6.73(1H,d,J=1.6 Hz), 6.87(1H, d,J=8 Hz), 7.18(1H,d,J=8 Hz), 7.53(1H,d,J=8 Hz), 8.55(1H, s).

IR(KBr): 1677, 1486, 1438, 1272, 1091, 1039 cm$^{-1}$

EXAMPLE 22

9-(1,3-Benzodioxole-5-yl)-8-methyl-1,3-dioxole[4, 4-f]quinoline-7-carboxamide

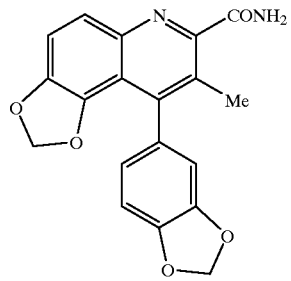

9-(1,3-Benzodioxole-5-yl)-8-methyl-1,3-dioxole[4,5-f] quinoline-7-carboxylic acid (150 mg), which was produced in Reference Example 14, was dissolved in a mixture of THF (20 ml) and DMF (2 drops), followed by dropwise addition of oxalyl chloride (75 µl.) The reaction mixture was stirred at room temperature one hour, and the solvent was distilled off under reduced pressure. The residue was dissolved in THF (20 ml) and added slowly to 28% aqueous ammonia solution. After being stirred at room temperature for 1 hour, the mixture was concentrated under reduced pressure. The residue was dissolved in THF (20). The solution was added gradually to 28% aqueous ammonia solution (50 ml) and stirred at room temperature for 10 minutes. The resulting product was extracted with ethyl acetate. The extract was washed with water, dried over magnesium sulfate and distilled to evaporate the solvent to yield the title compound as yellow crystals (135 mg). Some portions of the crude crystals were recrystalized from THF-ethyl acetate for elemental analysis and instrumental analysis.

m.p.: 214–216° C.

NMR (CDCl$_3$) δ: 2.50(3H,s) 5.68(1H,brs), 6.05(2H,m), 6.67(2H,m), 6.88(1H,d,J=8 Hz), 7.34(1H,d,J=8 Hz), 7.69 (1H,d,J=9 Hz), 7.84(1H,brs).

Elemental Analysis for C$_{19}$H$_{14}$N$_2$)$_5$ Calcd: C, 65.14%; H, 4.03%; N, 8.00% Found: C, 64.84%; H,,3.92%; N, 7.76%

EXAMPLE 23

N-methyl-9-(1,3-benzodioxole-5yl)-8-methyl-1,3-dioxolo [4,5-f]quinoline-7-carboxamide

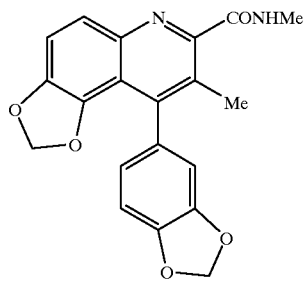

9-(1,3-Benzodioxole-5-yl)-8-methyl-1,3-dioxolo[4,5-f] quinoline-7-carboxylic acid (150 mg), which was produced in Reference Example 14, was dissoved in a mixture or THF (20 ml) and DMF (2drops), followed by addition of oxalyl chloride (75 µl). The reaction mixture was stirred at room temperature for one hour and concentrated under reduced pressure. The residue was dissolved in THF (20 ml), the solution was added dropwise to methylamine (40% methanol solution: 20 ml). The mixture was stirred at room temperature for ten minutes. The product was extracted with ethyl acetate. The extract was washed with water, dried over magnesium sulfate and concentrated under reduced pressure to yield the title compound as yellow crystals (61 mg). Some portions of the crude crystals were recrystallized from THF-ethyl acetate for use for elemental analysis and instrumental analysis.

m.p.: 141–146° C.

NMR (CDCl$_3$) δ: 2.50(3H,s), 3.05(3H,d,J=5Hz), 5.87 (1H,brs), 6.05(2H,m), 6.67(2H,m), 6.88(1H,d,J=8Hz), 7.34 (1H,d,J=9Hz), 7.67(1H,d,J=9 Hz), 7.90(1H,brs).

Elemental Analysis for C$_{20}$H$_{16}$N$_2$O$_5$ Calcd : C, 65.93%; H, 4.43%; N, 7.69% Found : C, 65.67%; H, 4.24%; N, 7.53%

EXAMPLE 24

N-Methyl-9-(4-trifluoromethoxyphenyl)-8-hydroxymethylnaphtho[1,2-d]-1,3-dioxol-7-carboxamide

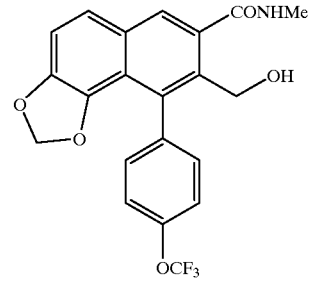

Using 10-(4-trifluoromethoxyphenyl)-fro[3',4':6,7] naphtho[1,2-d]-1,3-dioxol-7(9H)-one as obtained in Reference Example 15, the title compound was obtained in the same manner as in Example 1.

m.p.: 195–197° C. (recrystallized from ethyl acetate-isopropyl ether)

NMR (CDCl$_3$) δ: 1.76(1H,brs), 3.09 (3H,d,J=4,6Hz), 4.35(2H,s), 5.78(2H,s), 6.37(1H, brs), 7.20–7.40(5H,m), 7.47(1H,d,J=8.4Hz), 7.97(1H,s).

IR (KBr): 32,97, 1634, 1254 cm$^{-1}$

Elemental analysis for C$_{21}$H$_{16}$F$_3$NO$_5$ Calcd : C, 60.15%; H, 3.85%; N, 3.34% Found : C, 60.01%; H, 3.96%; N, 3.40%

EXAMPLE 25

9-(4-Trifluoromethoxyphenyl)naphtho[1,2-d]-1,3-dioxol-7-carboxamide

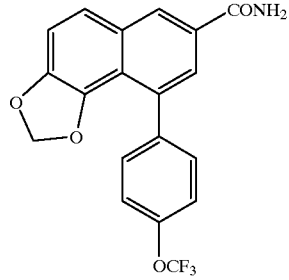

Using 9-(4-trifluoromethoxyphenyl)-naphtho[1,2-di]-1,3-dioxol-7-carboxylic acid as obtained in Reference Example 16, the title compound was obtained in the same manner as in Example 11.

m.p.: 188–190° C. (recrystallized from ethyl acetate-isopropyl ether)

NMR (CDCl$_3$) δ: 5.60–6.20(2H,brs), 5.94(2H,s), 7.20–7.34(3H,m), 7.46(2H,d,J=8.8Hz), 7.60–7.66(2H,m,), 8.32(1H,d,J=1.4Hz).

IR (KRr): 1632, 1466, 1292 cm$^{-1}$

Elemental analysis for $C_{19}H_{12}F_3NO_4$ Calcd : C, 60.81%; H, 3.22%; N, 3.73% Found : C, 60.74%; H, 3.34%; N, 3.69%

EXAMPLE 26

N-Methyl-4-(1,3-benzodioxol-5-yl)-6.7-diethoxy-3-hydroxymethyl-naphthalene-2-carboxamide

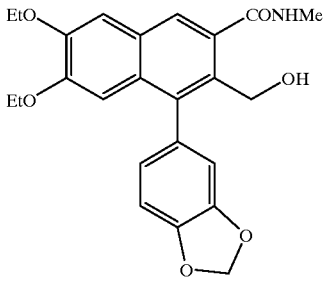

Using 4-(1,3-benzodioxol-5-yl)-6.7-diethoxynaphtho[2,3-c]furan-1(3H)-one as obtained in Reference Example 17, the title compound was obtained in the same manner as in Example 1.

NMR (CDCl$_3$) δ: 1.41(3H,t,J=7Hz), 1.54(3H, t,J=7Hz), 3.08(3H,d,J=5Hz), 3.94(2H,q,J=7Hz), 4.30–4.50(2H,m), 6.03(1H,d,J=1.4Hz), 6.09(1H,d,J=1.4Hz), 6.42(1H,m), 6.75–6.90(3H,m), 6.95)(1H,d,J=8Hz), 7.13(1H,s), 7.85(1H, s).

EXAMPLE 27

N-Methyl-9=(4-trifluoromethoxyphenyl)-8-hydroxymethyl-1,3dioxolo[4,5-f]quinoline-7-carboxamide

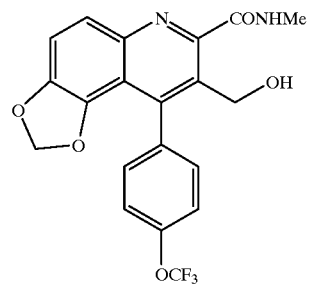

Using 10-(4-trifluoromethoxyphenyl)-1,3-dioxolo[4,5-f]fro[3,4-b]quinolin-7(9H)-one as obtained in Reference Example 18, the title compound was obtained in the same manner as in Example 1.

NMR (CDCl$_3$) δ: 3.12(3H,d,J=5Hz), 4.57(2H,d,J=8Hz), 5.30(1H,t,J=8Hz), 5.87(1H,s), 7.25–7.40(3H,m), 7.43(1H,d, J=9Hz), 7.75(1H,d,J=9Hz), 8.28(1H,m)

EXAMPLE 28

N-Methyl-4-(1,3-benzodioxol-5-yl)-3-hydroxymethyl-6-methoxyquinoline-carboxamide

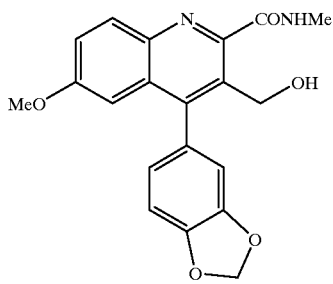

Using 5-(1,3-benzodioxol-5-yl)-7-methoxyfro[4,5-f]fro[3,4-b]quinolin-2(4H)one as obtained in Reference Example 19, the title compound was obtained in the same manner as in Example 1.

NMR (CDCl$_3$) δ: 3.12(3H,d,J=5Hz), 3.77(3H,s), 4.67 (2H,d,J=8Hz), 5.39(1H,t,J=8Hz), 6.06(1H,d,J=1.4Hz), 6.11 (1H,d,J=1.4Hz), 6.75–7.00(4H,m), 7.38(1H,dd,J=3,9Hz), 7.99(1H,d,J=9Hz), 8.48(1H,m).

EXAMPLE 29

8-(1,3-Benzodioxol-5-yl)naphtho[2,3-d]-1,3-dioxol-6-carboxamide

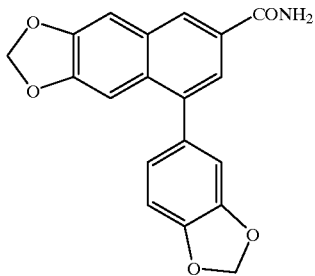

Using 8-(1,3-benzodioxol-5-yl)-naphtho[2,3-d]-1,3-dioxol-6-carboxylic acid as obtained in Reference Example 20, the title compound was obtained in the same manner as in Example 11.

NMR (CDCl$_3$) δ: 5.90–6.20(2H,m), 6.06(2H,s), 6.07(2H, s), 6.85–7.00(3H,m), 7.22(1H,s), 7.24(1H,s), 7.60(1H,d,J=1.9Hz), 8.18(1H,d,J=1.9Hz).

EXAMPLE 30

N-Methyl-8-(1,3-benzodioxol-5-yl)naphtho[2,3-d]-1,3-dioxol-6-carboxamide

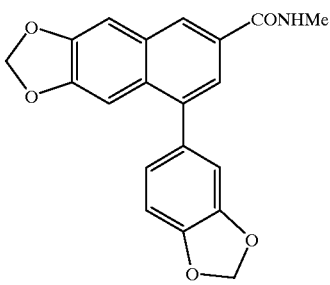

NMR (CDCl$_3$) δ: 3.05(3H,d,J=7Hz), 6.05(4H,s), 6.25(1H,m), 6.80–7.00(3H,m), 7.20(1H,s), 7.22(1H,s). 7.55(1H, d,J=1.9Hz), 8.12(1H,d,J=1.9Hz).

EXAMPLE 31

6-Chloro-4-(4-chlorophenyl)-3-hydroxymethyl-N-methyl-naphthalene-2-carboxamide

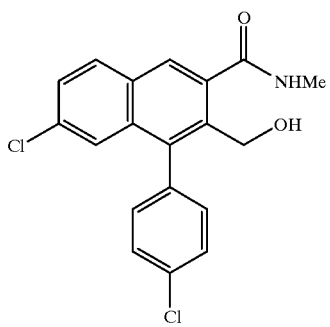

Using 6-chloro-4-(4-chlorophenyl)naphtho[2,3-c]furan-1(3H)-one as obtained in Reference Example 21, the title compound was obtained in the same manner as in Example 1.

m.p.: 160° C. (decomp.) (recrystallized from THF)

NMR (CDCl$_3$) δ: 3.09(3H,d,J=4.8Hz), 4.39(2H,s), 6.49(1H,brs), 7.28(2H,d,J=8.4Hz), 7.39(1H,m), 7.34(1H,m), 7.51(2H,d,J=8.4Hz), 7.81(1H,d,J=8.4Hz), 8.00(1H,s).

IR (KBr): 3285, 3083, 2942, 2876, 1634, 1555, 1483 cm$^{-1}$

EXAMPLE 32

4-(4-Fluorophenyl)-3-(2-hydroxymethyl)-6-methoxy-N-methyl-2-carboxamide

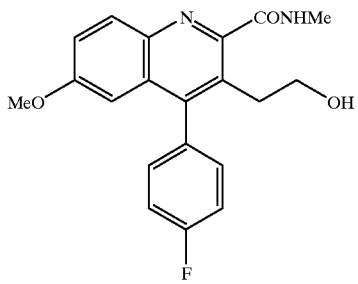

Using 5-(4-fluorophenyl)-3,4-dihydro-7-methoxy-1H-pyrano[3,4-b]quinolin-1-one as obtained in Reference Example 22, the title compound was obtained in the same manner as in Example 1.

m.p.: 139–140° C. (recrystallized from ethyl acetate-THF)

NMR (CDCl$_3$) δ: 3.09(3H,d,J=5.0Hz), 3.25(2H,t,J=6.0Hz), 3.69(3H,s), 3.69(2H,m), 4.52(1H,m), 6.44(1H,d,J=2.4Hz), 7.25(4H,m), 7.35(1H,dd,J=9.2,2.4Hz), 7.98(1H,d,J=9.2Hz), 8.19(1H,brs).

IR (KBr): 3316, 2942, 1651, 1618, 1493 cm$^{-1}$

Elemental analysis for $C_{19}H_{14}FNO_3$ Calcd : C, 70.58%; H, 4.36%; N, 4.33% Found : C, 70.49%; H, 4.57%; N, 4.26%

EXAMPLE 33

9-(1,3-Benzodioxol-5-yl)-8-(2-hydroxyethyl)-N-methyl-1,3-dioxolo[4,5-f]quinoline-7-carboxamide

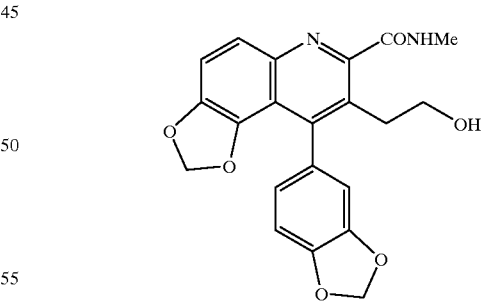

Using 11-(1,3-benzodioxol-5-yl)-9,10-dihydro-7H-1,3-dioxolo[4,5-f]pyrano[3,4-b]quinolin-7-one as obtained in Reference Example 23, the title compound was obtained in the same manner as in Example 1.

NMR (CDCl$_3$) δ: 3.07 (3H,d,J=5.2Hz), 3.1–3.3(2H,m), 3.71(2H,t,J=6.2Hz), 5.87(1H,d,J=1.4Hz), 5.87(1H,d,J=1.4Hz), 6.04(1H,d,J=1.4Hz), 6.07(1H,d,J=1.4Hz), 6.65–6.75(2H,m), 6.86(1H,d,J=7.8Hz), 7.37(1H,d,J=8.8Hz), 7.69(1H,d,J=8.8Hz), 8.10(1H,m).

EXAMPLE 34

9-(1,3-Benzodioxol-5-yl)-N-methyl-8-methylaminocarboxymethyl-1,3-dioxolo[4,5-f]quinoline-7-carboxamide

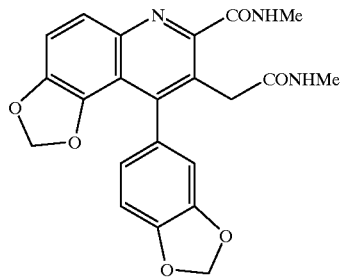

A mixture of 9-(1,3-benzodioxol-5-yl)-8-ethoxycarbonylmethyl-1,3-dioxolo[4,5-f]quinoline-7-carboxylic acid ethyl ester as obtained in Reference Example 23 (a) (106 mg), a 40% methylamine-methanol solution (5 ml) and THF (5 ml) was heated at 140° C. in a sealed tube for 2 hours. After cooling, the reaction mixture was diluted with water and extracted with ethyl acetate. After being washed with brine, the extract was dried with magnesium sulfate; the solvent was distilled off under reduced pressure. After the insoluble substances were filtered off, the product was treated with isopropyl ether to yield the title compound as a pale yellow crystal (4.6 mg).

NMR (CDCl$_3$) δ: 2.75(3H,d,J=4.8Hz), 3.03(3H,d,J=5.2Hz), 3.9–4.1(2H,m), 5.02(1H,m), 5.86(1H,d,J=1.4Hz), 5.88(1H,d,J=1.4Hz), 6.01(1H,d,J=1.4Hz), 6.05(1H,d,J=1.4Hz), 6.73(1H,dd,J=7.8,1.6Hz), 6.78(1H,d,J=1.6Hz), 6.86(1H,d,J=7.8Hz), 7.38(1H,d,J=8.8Hz), 7.70(1H,d,J=8.8Hz), 8.13(1H,m).

EXAMPLE 35

6-Chloro-4-(4-pyridyl)-2-quinolinecarboxamide

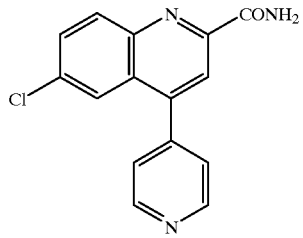

Using 6-chloro-4-(4-pyridyl)-2-quinolinecarboxylic acid as obtained in Reference Example 24, the title compound was obtained in the same manner as in Example 11.

NMR (CDCl$_3$) δ: 7.65(2H,dd,J=4.4,1.4Hz), 7.81(1H,d,J=2.2Hz), 7.92(1H,brs), 7.95(1H,dd,J=8.8,2.2Hz), 8.09(1H,s), 8.24(1H,d,J=8.8Hz), 8.40(1H,brs), 8.81(2H,dd,J=4.4, 1.4Hz).

Elemental analysis for C$_{15}$H$_{10}$N$_3$OCl Calcd : C, 63.50%; H, 3.55%; N, 14.81% Found : C, 63.38%; H, 3.62%; N, 14.75%

EXAMPLE 36

6-Chloro-N-methyl-4-(4-pyridyl)-2-quinolinecarboxamide

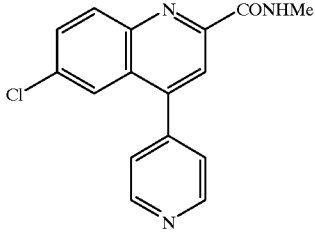

Using 6-chloro-4-(4-pyridyl)-2-quinolinecarboxylic acid as obtained in Reference Example 24, the title compound was obtained in the same manner as in Example 11.

NMR (CDCl$_3$) δ: 3.13(3H,d,J=5.2Hz), 7.45(2H,dd,J=4.4, 1.4Hz), 7.75(1H,dd,J=8.8,2.2Hz), 7.83(1H,d,J=2.2Hz), 8.13 (1H,d,J=8.8Hz), 8.19(1H,m), 8.29(1H,s), 8.84(2H,dd,J=4.4, 1.6Hz).

Elemental analysis for C$_{16}$H$_{12}$N$_3$OCl Calcd : C, 64.54%; H, 4.06%; N, 14.11% Found : C, 64.55%; H, 4.09%; N, 14.06%

EXAMPLE 37

6-Chloro-N-(4-methoxyphenyl)-4-(4-pyridyl)-2-quinolinecarboxamide

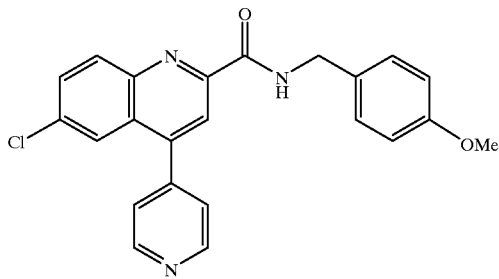

Using 6-chloro-4-(4-pyridyl)-2-quinolinecarboxylic acid as obtained in Reference Example 24, the title compound was obtained in the same manner as in Example 11.

NMR (CDCl$_3$) δ: 3.82(3H,s), 4.69(2H,d,J=5.8Hz), 6.91 (2H,d,J=8.8Hz), 7.36(2H,d,J=8.8Hz), 7.45(2H,dd,J=4.4, 1.8Hz), 7.73(1H,dd,J=8.8,2.2Hz), 7.83(1H,d,J=2.2Hz), 8.11 (1H,d,J=8.8Hz), 8.32(1H,s), 8.47(1H,m), 8.84(2H,dd,J=4.4, 1.8Hz).

Elemental analysis for C$_{28}$H$_{18}$N$_3$O$_2$Cl•¼H$_2$O Calcd : C, 67.65%; H, 4.57%; N, 10.29% Found : C, 67.71%; H, 4.67%; N, 10.23%

EXAMPLE 38

9-(4-Methoxyphenyl)-1,3-dioxolo[4,5-f]quinoline-7-carboxamide

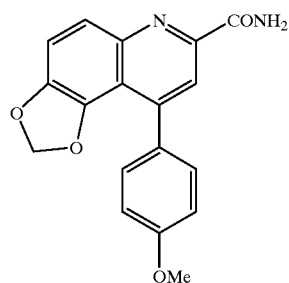

Using 9-(4-methoxyphenyl)-1,3-dioxolo[4,5-f]quinoline-7-carboxylic acid as obtained in Reference Example 25, the title compound was obtained in the same manner as in Example 11.

NMR (CDCl$_3$) δ: 3.89(3H,s), 5.70(1H,brs), 6.02(2H,s), 6.89(2H,d,J=8.8Hz), 7.43(2H,d,J=8.8Hz), 7.46(1H,d,J=8.8Hz), 7.82(1H,d,J=8.8Hz), 8.00(1H,s).

EXAMPLE 39

9-(4-Methoxyphenyl)-N-methyl-1,3-dioxolo[4,5-f]quinoline-7-carboxamide

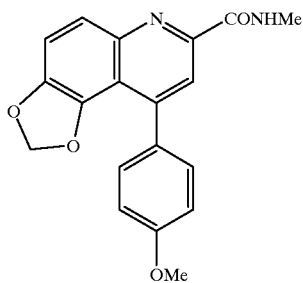

Using 9-(4-methoxyphenyl)-1,3-dioxolo[4,5-f]quinoline-7-carboxylic acid as obtained in Reference Example 25, the title compound was obtained in the same manner as in Example 11.

NMR (CDCl$_3$) δ: 3.10(3H,d,J=5.2Hz), 3.89(3H,s), 6.00 (2H,s), 6.98(2H,d,J=8.8Hz), 7.43(2H,d,J=8.8Hz), 7.45(1H,d,J=8.8Hz), 7.79(1H,d,J=8.8Hz), 8.10(1H,s), 8.17(1H,m).

EXAMPLE 40

9(4-Methoxyphenyl)-N-[(4-methoxyphenyl)methyl]-1,3-dioxolo[4,5-f]quinoline-7-carboxamide

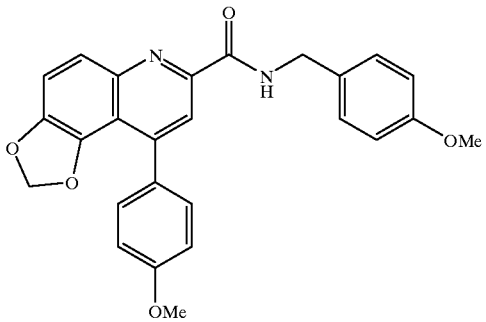

Using 9-(4-methoxyphenyl)-1,3-dioxolo[4,5-f]quinoline-7-carboxylic acid as obtained in Reference Example 25, the title compound was obtained in the same manner as in Example 11.

NMR (CDCl$_3$) δ: 3.81(3H,s), 3.89(3H,s), 4.66(2H,d,J=5.8Hz), 6.00(2H,s), 6.90(2H,d,J=8.8Hz), 6.98(2H,d,J=8.4Hz), 7.3–7.5(5H,m), 7.76(1H,d,J=8.8Hz), 8.13(1H,s), 8.44(1H,m).

EXAMPLE 41

9-(1,3-Benzodioxol-5-yl)-N,N-dimethyl-1,3-dioxolo[4,5-f]quinoline-7-carboxamide

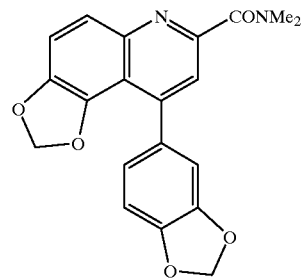

Using 9-(1,3-benzodioxol-5-yl)-1,3-dioxolo[4,5-f]quinoline-7-carboxylic acid as obtained in Reference Example 26, the title compound was obtained in the same manner as in Example 11.

NMR (CDCl$_3$) δ: 3.18(3H,s), 3.21(3H,s), 6.00(2H,s), 6.83–6.98(3H,m), 7.22(1H,d,J=9.0Hz), 7.51(1H,s), 7.78 (1H,d,J=9.0Hz).

Elemental analysis for $C_{20}H_{16}N_2O_5$ Calcd : C, 65.93%; H, 4.43%; N, 7.69% Found : C, 65.71%; H, 4.34%; N, 7.59

EXAMPLE 42

9-(1,3-Benzodioxol-5-yl)-N-methyl-1,3-dioxolo[4,5-f]quinoline-7-carboxamide

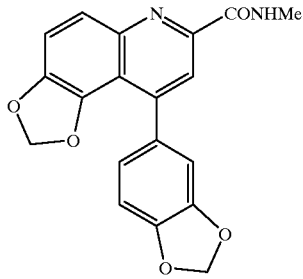

Using 9-(1,3-benzodioxol-5-yl)-1,3-dioxolo[4,5-f]quinoline-7-carboxylic acid as obtained in Reference Example 26, the title compound was obtained in the same manner as in Example 11.

NMR (CDCl$_3$) δ: 3.08(3H,d,J=5.2Hz), 5.99(2H,s), 6.01(2H,s), 6.83–7.00(3H,m), 7.39(1H,d,J=8.8Hz), 7.74(1H,d,J=8.8Hz), 8.07(1H,s), 8.21 1H,brd,J=4.8Hz).

EXAMPLE 43

9-(1,3-Benzodioxol-5-yl)-N-propyl-1,3-dioxolo[4,5-f]quinoline-7-carboxamide

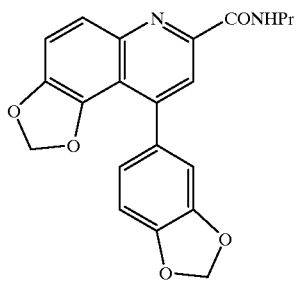

Using 9-(1,3-benzodioxol-5-yl)-1,3-dioxolo[4,5-f]quinoline-7-carboxylic acid as obtained in Reference Example 26, the title compound was obtained in the same manner as in Example 11.

NMR (CDCl$_3$) δ: 1.03(3H,t,J=7.6Hz), 1.71(2H,q,J=7.2Hz), 3.49(2H,q,J=7.0Hz), 6.02(2H,s), 6.03(2H,s), 6.84–7.00(3H,m), 7.43(1H,d,J=8.8Hz), 7.79(1H,d,J=8.8Hz), 8.08(1H,s), 8.23(1H,brs).

Elemental analysis for $C_{21}H_{16}N_2O_5 \cdot 0.3H_2O$ Calcd : C, 65.72% H, 4.88%; N, 7.30% Found : C, 65.70% H, 5.08%; N, 7.06%

EXAMPLE 44

9-(1,3-Benzodioxol-5-yl)-N-(4-methoxyphenyl)-1,3-dioxolo[4,5-f]quinoline-7-carboxamide

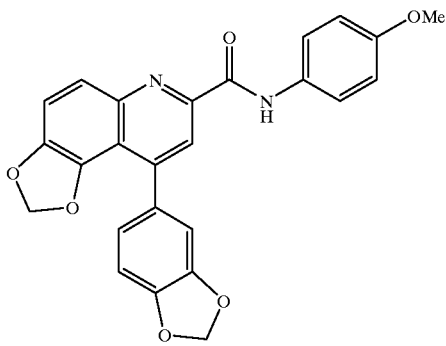

Using 9-(1,3-benzodioxol-5-yl)-1,3-dioxolo[4,5-f]quinoline-7-carboxylic acid as obtained in Reference Example 26, the title compound was obtained in the same manner as in Example 11.

NMR (CDCl$_3$) δ: 3.84(3H,s), 6.06(4H,s), 6.87–7.03(5H,m), 7.30(1H,s), 7.50(1H,d,J=8.8Hz), 7.76(2H,d,J=9.2Hz), 7.91(1H,d,J=8.8Hz), 8.18(1H,s).

Elemental analysis for $C_{25}H_{18}N_2O_6 \cdot 0.2H_2O$ Calcd : C, 67.32%; H, 4.15%; N, 6.28% Found : C, 67.21%; H, 4.11%; N, 6.25%

EXAMPLE 45

9-(1,3-Benzodioxol-5-yl)-N-[(4-methoxyphenyl)methyl]-1,3-dioxolo[4,5-f]quinoline-7-carboxamide

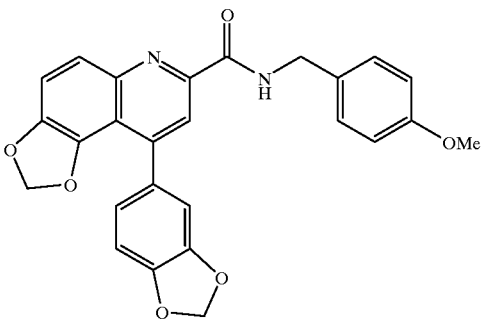

Using 9-(1,3-benzodioxol-5-yl)-1,3-dioxolo[4,5-f]quinoline-7-carboxylic acid as obtained in Reference Example 26, the title compound was obtained is the same manner as in Example 11.

NMR (CDCl$_3$) δ: 3.81(3H,s), 4.67(2H,d,J=5.8Hz), 6.03(2H,s), 6.05(2H,s), 6.80–7.08(5H,m), 7.35(2H,d,J=8.8Hz), 7.43(1H,d,J=9.2Hz), 7.76 (1H,d,J=9.2Hz), 8.12(1H,s), 8.43(1H,brs).

Elemental analysis for $C_{26}H_{20}N_2O_6 \cdot 0.1H_2O$ Calcd : C, 68.15%; H, 4.44%; N, 6.11%; Found : C, 68.0%4; H, 4.70%; N, 6.20%

EXAMPLE 46

9-(4-Fluorophenyl)-N-methyl-1,3-dioxolo[4,5-F]quinoline-7-carboxamide

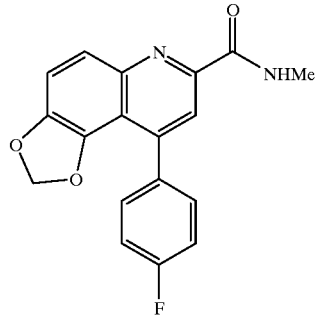

Using 9-(4-fluorophenyl)-1,3-dioxolo[4,5-f]quinoline-7-carboxylic acid as obtained in Reference Example 27, the title compound was obtained in the same manner as in Example 11.

m.p.: 233–235° C.

NMR (CDCl$_3$) δ: 3.10(3H,d,J=5.2Hz), 6.00(2H,s), 7.08–7.20(2H,m), 7.40–7.50(3H,m), 7.80(1H,d,J=9.0Hz), 8.10(1H,s), 8.16(1H,brs).

Elemental analysis for $C_{18}H_{13}N_2O_3F \cdot 0.1H_2O$ Calcd : C, 66.30%; H, 4.08%; N, 8.59% Found : C, 66.11%; H, 4.14%; N, 8.59%

EXAMPLE 47

9-(4-Fluorophenyl)-N-[(4-methoxyphenyl)methyl]-1,3-dioxolo[4,5-f]quinoline-7-carboxamide

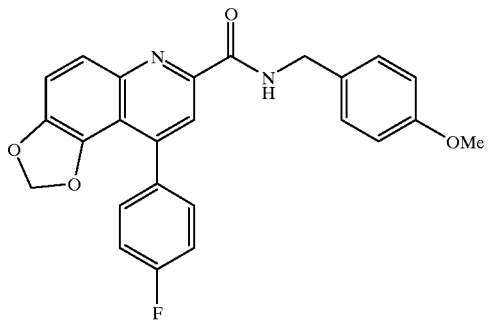

Using 9-(4-fluorophenyl)-1,3-dioxolo[4,5-f]quinoline-7-carboxylic acid as obtained in Reference Example 27, the title compound was obtained in the same manner as in Example 11.

m.p.: 171–173° C.

NMR (CDCl$_3$) δ: 3.81(3H,s), 4.67(2H,d,J=6.2Hz), 5.99(2H,s), 6.90(2H,d,J=8.4Hz), 7.06–7.22(2H,m), 7.35(2H,d,J=8.4Hz), 7.40–7.55(3H,m), 7.77(1H,d,J=8.8Hz), 8.12(1H,s), 8.44(1H,s).

Elemental analysis for $C_{23}H_{19}N_2O_4F \cdot 0.1H_2O$ Calcd : C, 69.47%; H, 4.47%; N, 6.48% Found : C, 69.31%; H, 4.51%; N, 6.45%

EXAMPLE 48

N-Benzyl-N-[9-(4-fluorophenyl)-1,3-dioxolo[4,5-f]quinoline-7-carbonyl]piperazine

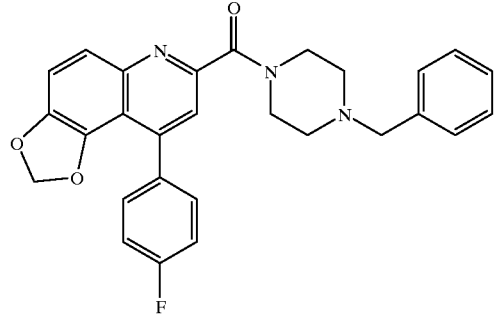

Using 9-(4-fluorophenyl)-1,3-dioxolo[4,5-f]quinoline-7-carboxylic acid as obtained in Reference Example 27, the title compound was obtained in the same manner as in Example 11.

m.p.: 147–148° C.

NMR (CDCl$_3$) δ: 2.50(2H, t, J=4.8 Hz), 2.59(2H, t, J=4.8 Hz), 3.77(2H, t, J=4.8 Hz), 3.88(2H, t, J=4.8 Hz), 5.96(2H, s), 7.02–7.20(2H, m), 7.20–7.38(5H, m), 7.38–7.50(3H, m), 7.52(1H, s), 7.78(1H, d, J=9.2 Hz).

Elemental analysis for $C_{28}H_{24}N_3O_3F$ Calcd: C, 71.63%; H, 5.15%; N, 8.95%. Found: C, 71.56%; H, 5.17%; N, 8.94%.

EXAMPLE 49

9-(4-Fluorophenyl)-N-[2-(4-methoxyphenyl)ethyl]-1,3-dioxolo[4,5-f]quinoline-7-carboxamide

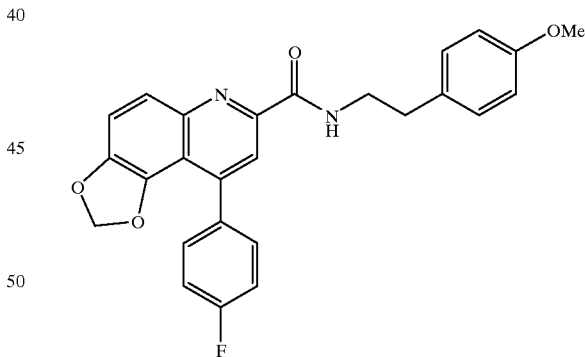

Using 9-(4-fluorophenyl)-1,3-dioxolo[4,5-f]quinoline-7-carboxylic acid as obtained in Reference Example 27, the title compound was obtained in the same manner as in Example 11.

NMR (CDCl$_3$) δ: 2.94(2H, t, J=6.8 Hz), 3.66–3.82(2H, m), 3.81(3H, s), 5.99(2H, s), 6.89(2H, d, J=8.8 Hz), 7.06–7.30(4H, m), 7.43(1H, d, J=8.8 Hz), 7.46(2H, d, J=8.8 Hz), 7.77(1H, d, J=8.8 Hz), 8.09(1H, s), 8.26(1H, brs).

Elemental analysis for $C_{26}H_{21}N_2O_4F$ Calcd: C, 70.26%; H, 4.76%; N, 6.30%. Found: C, 70.19%; H, 4.83%; N, 6.29%.

EXAMPLE 50

N-[2-[4-(Acetylamino)phenyl]ethyl]-9-(4-fluorophenyl)-1,3-dioxolo[4,5-f]quinoline-7-carboxamide

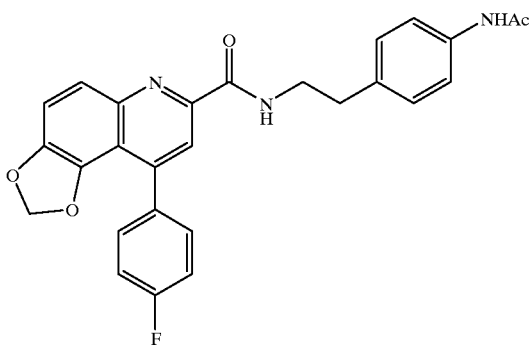

Using 9-(4-fluorophenyl)-1,3-dioxolo[4,5-f]quinoline-7-carboxylic acid as obtained in Reference Example 27, the title compound was obtained in the same manner as in Example 11.

NMR (CDCl$_3$) δ: 2.18(3H, s), 2.96(2H, t, J=6.6 Hz), 3.70–3.80(2H, m), 6.00(2H, s), 7.00–7.35(5H, m), 7.35–7.60(4H, m), 7.78(1H, d, J=8.8 Hz), 8.08(1H, s), 8.27(1H, brs).

EXAMPLE 51

9-(4-Fluorophenyl)-N-(2-hydroxyethyl)-1,3-dioxolo[4,5-f]quinoline-7-carboxamide

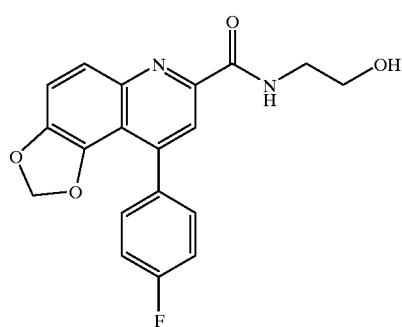

Using 9-(4-fluorophenyl)-1,3-dioxolo[4,5-f]quinoline-7-carboxylic acid as obtained in Reference Example 27, the title compound was obtained in the same manner as in Example 11.

NMR (CDCl$_3$) δ: 2.88(1H, brs), 3.65–3.80(2H, m), 3.90 (2H, brs), 6.00(2H, s), 7.05–7.20(2H, m), 7.38–7.52(3H, m), 7.81(1H, d, J=8.8 Hz), 8.07(1H, s), 8.55(1H, brs).

EXAMPLE 52

3-Dimethylaminomethyl-6-methoxy-4-(4-methoxyphenyl)-N-methyl-2-quinolinecarboxamide

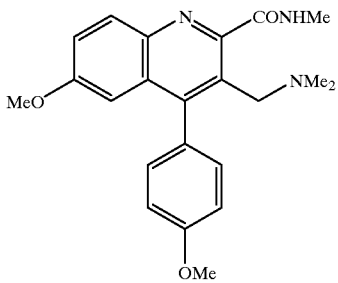

After a mixture of 3-bromomethyl-6-methoxy-4-(4-methoxyphenyl)quinoline-2-carboxylic acid methyl ester (152 mg), a 50% aqueous solution of dimethylamine (0.5 ml) and methanol (5 ml) was stirred at room temperature for 2 hours, water was added to the reaction mixture, followed by extraction with ethyl acetate. After being washed with brine, the extract was dried over magnesium sulfate; the solvent was distilled off under reduced pressure. To the residue, THF (5 ml) and a 40% methylamine-methanol solution (5 ml) was added, followed by refluxing for 16 hours, after which the solvent was distilled off under reduced pressure to yield the title compound as a colorless powder (26 mg).

NMR (CDCl$_3$) δ: 2.06(6H, s), 2.78(3H, d, J=5.2 Hz), 3.70(3H, s), 3.72(2H, m), 3.93(3H, s), 6.66(1H, d, J=3.0 Hz), 7.05(2H, d, J=8.8 Hz), 7.16(2H, d, J=8.8 Hz), 7.34(1H, dd, J=9.0, 3.0 Hz), 8.01(1H, d, J=9.0 Hz), 8.44(1H, m).

EXAMPLE 53

N-Methyl-8-(1-piperidinyl)-1,3-dioxolo[4,5-g]quinoline-6-carboxamide

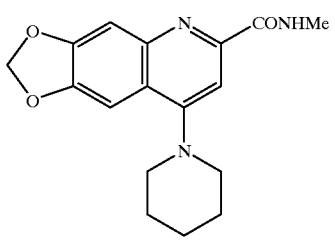

After a mixture of ethyl 8-(1-piperidinyl)-1,3-dioxolo[4,5-g]quinoline-6-carboxylate as obtained in Reference Example 31 (60 mg) and a 40% methylamine-methanol solution (5 ml) was stirred at room temperature for 3 hours, the solvent was distilled off under reduced pressure to yield the title compound as a colorless powder (33.6 mg).

NMR (CDCl$_3$) δ: 1.5–2.0(6H, m), 3.06(3H, d, J=4.8 Hz), 3.15(4H, m), 6.11(2H, s), 7.27(1H, s), 7.30(1H, s), 7.71(1H, s), 8.18(1H, brs).

EXAMPLE 54

N-Methyl-8-(1-pyrrolidinyl)-1,3-dioxolo[4,5-g]quinoline-6-carboxamide

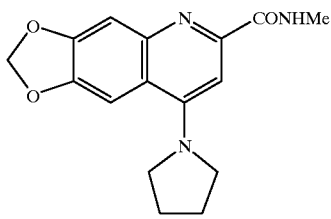

Using ethyl 8-(1-pyrrolidinyl)-1,3-dioxolo[4,5-g]quinoline-6-carboxylate as obtained in Reference Example 31, the title compound was obtained in the same manner as in Example 53.

NMR (CDCl$_3$) δ: 2.03(4H, m), 3.05(3H, d, J=5.2 Hz), 3.68(4H, m), 6.08(2H, s), 7.23(1H, s), 7.39(1H, s), 7.53(1H, s), 8.20(1H, brs).

EXAMPLE 55

N-Methyl-8-(4-morpholinyl)-1,3-dioxolo[4,5-g]quinoline-6-carboxamide

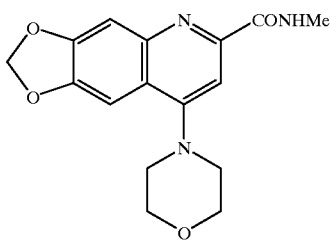

Using ethyl 8-(4-morpholinyl)-1,3-dioxolo[4,5-g]quinoline-6-carboxylate as obtained in Reference Example 32, the title compound was obtained in the same manner as in Example 53.

NMR (CDCl$_3$) δ: 3.07(3H, d, J=5.2 Hz), 3.21(4H, m), 3.97(4H, m), 6.13(2H, s), 7.31(2H, s), 7.75(1H, s), 8.17(1H, m).

EXAMPLE 56

N-Methyl-8-(4-methylpiperazin-1-yl)-1,3-dioxolo[4,5-g]quinoline-6-carboxamide

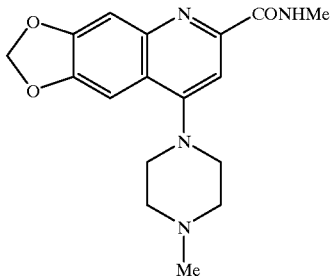

Using ethyl 8-(4-methylpiperazin-1-yl)-1,3-dioxolo[4,5-g]quinoline-6-carboxylate as obtained in Reference Example 33, the title compound was obtained in the same manner as in Example 53.

NMR (CDCl$_3$) δ: 2.41(3H, s), 2.69(4H, m), 3.07(3H, d, J=5.2 Hz), 3.25(4H, m), 6.12(2H, s), 7.29(2H, s), 7.74(1H, s), 8.17(1H, m).

EXPERIMENTAL EXAMPLE 1

Induction of Alkaline Phosphatase (ALP) Production in Mouse Osteoblastic Cells Mouse-derived MC3T3-E1 osteoblast cells were seeded in a 96-well microtiter plate of α-minimum essential medium containing FCS (fetal calf serum) (8000 cells/well). After two days when the growth had become confluent, the test substance diluted to various concentrations in Table 1 with the medium either containing or not containing 3 ng/ml of BMP-4/7 heterodimer (described in Japanese Patent Application No. 111255/1994) was added, and the microtiter plate was further incubated for 72 hours. The plate was washed once with a physiological saline solution, followed by addition of a substrate solution. The resulting mixture was incubated at room temperature for 15 minutes, followed by addition of 0.05N NaOH to terminate the reaction. The absorbance at 405 nm was measured. The results as shown in Table 1 proved that the compounds of the present invention strengthen BMP activity, i.e. induction of ALP production by BMP and that those compounds themselves have excellent ALP production inducing activity regardless of the presence or absence of BMP.

TABLE 1

| Example No. | Conc. of compound (µM) | ALP Activity (1000 × A405 ± SD) | |
|---|---|---|---|
| | | BMP Addition | BMP Non-Addition |
| 1 | 1 | 386 ± 30* | 102 ± 5* |
| | 0.1 | 213 ± 5* | 58 ± 5* |
| | 0.01 | 193 ± 15 | 50 ± 5 |
| | 0 (control) | 173 ± 9 | 42 ± 5 |
| 2 | 1 | 478 ± 17* | 162 ± 18* |
| | 0.1 | 354 ± 15* | 95 ± 7* |
| | 0.01 | 323 ± 13 | 80 ± 2 |
| | 0 (control) | 268 ± 18 | 73 ± 4 |
| 4 | 1 | 554 ± 49* | 168 ± 4* |
| | 0.1 | 389 ± 25* | 108 ± 7* |
| | 0.01 | 301 ± 8 | 86 ± 3 |
| | 0 (control) | 303 ± 11 | 78 ± 6 |
| 5 | 1 | 431 ± 26* | 157 ± 11* |
| | 0.1 | 237 ± 14* | 62 ± 3* |
| | 0.01 | 170 ± 20 | 49 ± 1 |
| | 0 (control) | 171 ± 6 | 48 ± 3 |
| 6 | 1 | 459 ± 35* | 168 ± 1* |
| | 0.1 | 248 ± 6* | 74 ± 1* |
| | 0.01 | 177 ± 14 | 51 ± 2 |
| | 0 (control) | 165 ± 9 | 46 ± 5 |
| 8 | 1 | 570 ± 63* | 186 ± 26 |
| | 0.1 | 477 ± 15* | 134 ± 12 |
| | 0.01 | 426 ± 28 | 105 ± 22 |
| | 0 (control) | 395 ± 1 | 146 ± 49 |
| 22 | 1 | 326 ± 18* | 190 ± 10* |
| | 0.1 | 226 ± 6* | 149 ± 11* |
| | 0.01 | 187 ± 3 | 135 ± 8* |
| | 0 (control) | 182 ± 9 | 119 ± 5 |

*p < 0.05 vs control;
t-test

FORMULATION EXAMPLE 1

About 1,000 uncoated tablets measuring 6.5 mm in diameter and containing 5 mg of the compound of Example 1 can be prepared by mixing the following components (1)–(6) and compressing the mixture with a tablet machine. Film-coated tablets each measuring 6.6 mm in diameter can be obtained by coating those tablets with the following components (7)–(9).

| | | |
|---|---|---|
| (1) Compound of Example | 5 g | |
| (2) Lactose | 82.5 g | |
| (3) Hydroxypropylcellulose | 2.8 g | |
| (4) Magnesium stearate | 0.4 g | |
| (5) Hydroxypropylmethylcellulose 2910 | 2.994 g | |
| (6) Corn starch | 19.3 g | |
| (7) Macrogol 6000 | 0.6 g | |
| (8) Titanium oxide | 0.4 g | |
| (9) Iron sesquioxide | 0.006 g | |

FORMULATION EXAMPLE 2

Uncoated granules can be prepared by suspending or dissolving the following components (1), (2), (3), (4), (5), (6), (7) and (8) in purified water and coating a granular core material (2) with the suspension or solution. About 500 mg of 1% fine granules of the compound of Example 1 can be prepared by coating the uncoated granules with the components (9)–(11) to prepare fine granules and mixing with the following component (12). The fine granule are dispensed in packets in 500 mg per packet.

| | | |
|---|---|---|
| (1) | Compound of Example | 5 g |
| (2) | Lactose-crystalline cellulose (granule) | 330 g |
| (3) | D-mannotp | 29 g |
| (4) | Low-substituted hydroxypropylcellulose | 20 g |
| (6) | Talc | 25 g |
| (6) | Hydroxypropylcellulose | 50 g |
| (7) | Aspartame | 3 g |
| (8) | Dipotassium glycyrrhizinate | 3 g |
| (9) | Hydroxypropylmethylcellulose 2910 | 30 g |
| (10) | Titanium oxide | 3.5 g |
| (11) | Yellow iron sesquioxide | 0.5 g |
| (12) | Light silicic anyhydride | 1 g |

INDUSTRIAL APPLICABILITY

The cell differentiation inducing composition or the cell differentiation factor activity enhancing composition containing the compound [I] or a salt thereof has high BMP (bone morphogenetic protein)-like activity or enhances BMP activity and increases bone mass and strength by acting upon bone tissues. Therefore, the composition of the present invention is useful for the treatment or prevention of bone diseases such as osteoporosis and the acceleration of bone fracture healing or bone remodeling. This composition also has neurotrophic factor-like activity or enhances neurotrophic factor activity. Therefore, the composition is useful for the treatment or prevention of various nerve diseases such as Alzheimer's disease, senile dementia, Perkinson disease, motor neuronal diseases (e.g., amyotrophic lateral sclerosis) and diabetic peripheral neuropathy.

What is claimed is:
1. A compound represented by the formula:

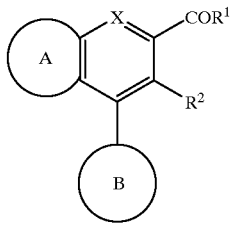

wherein $R^1$ is an amino group which may be substituted by
- (a) a $C_{1-6}$ alkyl group, $C_{2-6}$ alkenyl group, $C_{2-6}$ alkynyl group, $C_{3-6}$ cycloalkyl group, $C_{6-14}$ aryl group or $C_{7-16}$ aralkyl group, which may be substituted by a group selected from the group consisting of (i) a halogen atom, (ii) $C_{1-3}$ alkylenedioxy, (iii)nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) optionally halogenated $C_{1-6}$ alkoxy, (x) optionally halogenated $C_{1-6}$ alkylthio, (xi) hydroxy, (xii) amino, (xiii) mono-$C_{1-6}$ alkyl amino, (xiv) di-$C_{1-6}$ alkyl amino, (xv) 5 or 6 membered cyclic amino, (xvi) acyl amino selected from $C_{1-6}$ alkoxy-carbonyl amino, mono-$C_{1-6}$ alkylaminocarbonyl amino, $C_{1-6}$ alkylcarbonyl amino and $C_{1-6}$ alkylsulfonyl amino, (xvii) $C_{1-6}$ alkylcarbonyl, (xviii) carboxyl, (xix) $C_{1-6}$ alkoxy-carbonyl, (xx) carbamoyl, (xxi) mono-$C_{1-6}$ alkyl-carbamoyl, (xxii) di-$C_{1-6}$ alkyl-carbamoyl, (xxiii) $C_{6-10}$ aryl-carbamoyl, (xxiv) sulfo, (xxv) $C_{1-6}$ alkyl sulfonyl, (xxvi) $C_{6-10}$ aryl and (xvii) $C_{6-10}$ aryloxy,
- (b) a hydroxy group which may be substituted by a $C_{1-6}$ alkyl group, $C_{2-6}$ alkenyl group, $C_{2-6}$ alkynyl group, $C_{3-6}$ cycloalkyl group, $C_{6-14}$ aryl group or $C_{7-16}$ aralkyl group, which may be substituted by a group selected from the group consisting of (i) a halogen atom, (ii) $C_{1-3}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) optionally halogenated $C_{1-6}$ alkoxy, (x) optionally halogenated $C_{1-6}$ alkylthio, (xi) hydroxy, (xii) amino, (xiii) mono-$C_{1-6}$ alkyl amino, (xiv) di-$C_{1-6}$ alkyl amino, (xv) 5 or 6 membered cyclic amino, (xvi) acyl amino selected from $C_{1-6}$ alkoxy-carbonyl amino, mono-$C_{1-6}$ alkylaminocarbonyl amino, $C_{1-6}$ alkylcarbonyl amino and $C_{1-6}$ alkylsulfonyl amino, (xvii) $C_{1-6}$ alkylcarbonyl, (xviii) carboxyl, (xix) $C_{1-6}$ alkoxy-carbonyl, (xx) carbamoyl, (xxi) mono-$C_{1-6}$ alkyl-carbamoyl, (xxii) di-$C_{1-6}$ alkyl-carbamoyl, (xxiii) $C_{6-10}$ aryl-carbamoyl, (xxiv) sulfo, (xxv) $C_{1-6}$ alkyl sulfonyl, (xxvi) $C_{6-10}$ aryl and (xxvii) $C_{6-10}$ aryloxy, or
- (c) an amino group which may be substituted by an acyl group represented by any one of the formula: —(C=O)—$R^7$, —SO$_2$—$R^7$, —(C=O)NR$^8$R$^7$, —(C=O)O—$R^7$, —(C=S)O—$R^7$ or —(C=S)NR$^8$R$^7$ wherein $R^7$ is (a) hydrogen atom or (b) a $C_{1-6}$ alkyl group, $C_{2-6}$ alkenyl group, $C_{2-6}$ alkynyl group, $C_{3-6}$ cycloalkyl group, $C_{6-14}$ aryl group or $C_{7-16}$ aralkyl group, which may be substituted by a group selected from the group consisting of (i) a halogen atom, (ii) $C_{1-3}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) optionally halogenated $C_{1-6}$ alkoxy, (x) optionally halogenated $C_{1-6}$ alkylthio, (xi) hydroxy, (xii) amino, (xiii) mono-$C_{1-6}$ alkyl amino, (xiv) di-$C_{1-6}$ alkyl amino, (xv) 5 or 6 membered cyclic amino, (xvi) acyl amino selected from $C_{1-6}$ alkoxy-carbonyl amino, mono-$C_{1-6}$ alkylaminocarbonyl amino, $C_{1-6}$ alkylcarbonyl amino and $C_{1-6}$ alkylsulfonyl amino, (xvii) $C_{1-6}$ alkylcarbonyl, (xviii) carboxyl, (xix) $C_{1-6}$ alkoxy-carbonyl, (xx) carbamoyl, (xxi) mono-$C_{1-6}$ alkyl-carbamoyl, (xxii) di-$C_{1-6}$ alkyl-carbamoyl, (xxiii) $C_{6-10}$ aryl-carbamoyl, (xxiv) sulfo, (xxv) $C_{1-6}$ alkyl sulfonyl, (xxvi) $C_{6-10}$ aryl and (xxvii) $C_{6-10}$ aryloxy, and $R^8$ is hydrogen atom or a $C_{1-6}$ alkyl group, or (d) $R^1$ is a group formed by removing a hydrogen atom from a nitrogen atom of a 5 to 9 membered nitrogen-containing heterocycle which may have 1 to 3 hetero atoms selected from a nitrogen atom, an oxygen atom and a sulfur atom, other than carbon atoms and one nitrogen atom, and the nitrogen-containing heterocycle may be substituted by a group selected from the group consisting of (i) a halogen atom, (ii) $C_{1-3}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) optionally halogenated $C_{1-6}$ alkoxy, (x) optionally halogenated $C_{1-6}$ alkylthio, (xi) hydroxy, (xii) amino, (xiii) mono-$C_{1-6}$ alkyl amino, (xiv) di-$C_{1-6}$ alkyl amino, (xv) 5 or 6 membered cyclic amino, (xvi) acyl amino selected from $C_{1-6}$ alkoxy-carbonyl amino, mono-$C_{1-6}$ alkylaminocarbonyl amino, $C_{1-6}$ alkylcarbonyl amino and $C_{1-6}$ alkylsulfonyl amino, (xvii) $C_{1-6}$ alkylcarbonyl, (xviii) carboxyl, (xix) $C_{1-6}$ alkoxy-carbonyl, (xx) carbamoyl, (xxi) mono-$C_{1-6}$ alkyl-carbamoyl, (xxii) di-$C_{1-6}$ alkyl-carbamoyl, (xxiii) $C_{6-10}$ aryl-carbamoyl, (xxiv) sulfo, (xxv) $C_{1-6}$ alkyl sulfonyl, (xxvi) $C_{6-10}$ aryl and (xxvii) $C_{6-10}$ aryloxy;

$R^2$ is a hydrogen atom;

X is a methyne group which may be substituted;

a ring A is a 4–10 membered homo-cycle which is substituted by a lower alkylenedioxy;

and a ring B is a homo- or hetero-cycle which may be substituted; or a pharmaceutically acceptable salt thereof.

2. The compound as claimed in claim 1 wherein X is $CR^6$ wherein $R^6$ is (a) a hydrogen atom, (b) a halogen atom, (c) a $C_{1-6}$ alkyl group, $C_{2-6}$ alkenyl group, $C_{2-6}$ alkynyl group, $C_{3-6}$ cycloalkyl group, $C_{6-14}$ aryl group or $C_{7-16}$ aralkyl group which may be substituted by a group selected from the group consisting of (i) a halogen atom, (ii) $C_{1-3}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) optionally halogenated $C_{1-6}$ alkoxy, (x) optionally halogenated $C_{1-6}$ alkylthio, (xi) hydroxy, (xii) amino, (xiii) mono-$C_{1-6}$ alkyl amino, (xiv) di-$C_{1-6}$ alkyl amino, (xv) 5 or 6 membered cyclic amino, (xvi) acyl amino selected from $C_{1-6}$ alkoxy-carbonyl amino, mono-$C_{1-6}$ alkylaminocarbonyl amino, $C_{1-6}$ alkylcarbonyl amino, $C_{1-6}$ alkylcarbonyl amino and $C_{1-6}$ alkylsulfonyl amino, (xvii) $C_{1-6}$ alkylcarbonyl, (xviii) carboxyl, (xix) $C_{1-6}$ alkoxy-carbonyl, (xx) carbamoyl, (xxi) mono-$C_{1-6}$ alkyl-carbamoyl, (xxii) di-$C_{1-6}$ alkyl-carbamoyl, (xxiii) $C_{6-10}$ aryl-carbamoyl, (xxiv) sulfo, (xxv) $C_{1-6}$ alkyl sulfonyl, (xxvi) $C_{6-10}$ aryl and (xxvii) $C_{6-10}$ aryloxy or (d) —$OR^{6''}$ is (a') a hydrogen atom or (b') a $C_{1-6}$ alkyl group, $C_{2-6}$ alkenyl group, $C_{2-6}$ alkynyl group, $C_{3-6}$ cycloalkyl group, $C_{6-14}$ aryl group or $C_{7-16}$ aralkyl group which may be substituted by a group selected from the group consisting of (i) a halogen atom, (ii) $C_{1-3}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) optionally halogenated $C_{1-6}$ alkoxy, (x) optionally halogenated $C_{1-6}$ alkylthio, (xi) hydroxy, (xii) amino, (xiii) mono-$C_{1-6}$ alkyl amino, (xiv) di-$C_{1-6}$ alkyl amino, (xv) 5 or 6 membered cyclic amino, (xvi) acyl amino selected from $C_{1-6}$ alkoxy-carbonyl amino, mono-$C_{1-6}$ alkylaminocarbonyl amino, $C_{1-6}$ alkylcarbonyl amino and $C_{1-6}$ alkylsulfonyl amino, (xvii) $C_{1-6}$ alkylcarbonyl, (xviii) carboxyl, (xix) $C_{1-6}$ alkoxy-carbonyl, (xx) carbamoyl, (xxi) mono-$C_{1-6}$ alkyl-carbamoyl, (xxii) di-$C_{1-6}$ alkyl-carbamoyl, (xxiii) $C_{6-10}$ aryl-carbamoyl, (xxiv) sulfo, (xxv) $C_{1-6}$ alkyl sulfonyl, (xxvi) $C_{6-10}$ aryl and (xxvii) $C_{6-10}$ aryloxy;

the ring A is a 4 to 10 membered cyclic hydrocarbon which is substituted by $C_{1-3}$ alkylenedioxy; and the ring B is a 3 to 10 membered cyclic hydrocarbon or 5 to 9 membered heterocycle containing 1 to 4 hetero atoms selected from a nitrogen atom, a sulfur atom and an oxygen atom other than carbon atoms, and the 3 to 10 membered cyclic hydrocarbon or 5 to 9 membered heterocycle may be substituted by a group selected from the group consisting of (i) a halogen atom, (ii) $C_{1-3}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) optionally halogenated $C_{1-6}$ alkoxy, (x) optionally halogenated $C_{1-6}$ alkylthio, (xi) hydroxy, (xii) amino, (xiii) mono-$C_{1-6}$ alkyl amino, (xiv) di-$C_{1-6}$ alkyl amino, (xv) 5 or 6 membered cyclic amino, (xvi) acyl amino selected from $C_{1-6}$ alkoxy-carbonyl amino, mono-$C_{1-6}$ alkylaminocarbonyl amino, $C_{1-6}$ alkylcarbonyl amino and $C_{1-6}$ alkylsulfonyl amino, (xvii) $C_{1-6}$ alkylcarbonyl, (xviii) carboxyl, (xix) $C_{1-6}$ alkoxy-carbonyl, (xx) carbamoyl, (xxi) mono-$C_{1-6}$ alkyl-carbamoyl, (xxii) di-$C_{1-6}$ alkyl-carbamoyl, (xxiii) $C_{6-10}$ aryl-carbamoyl, (xxiv) sulfo, (xxv) $C_{1-6}$ alkyl sulfonyl, (xxvi) $C_{6-10}$ aryl and (xxvii) $C_{6-10}$ aryloxy.

3. The compound as claimed in claim 1 wherein $R^1$ is a group represented by the formula:

wherein $R^3$ and $R^4$ is the same or different and are independently a hydrogen atom, a hydroxy group which may be substituted, a lower alkyl group which may be substituted, an acyl group, an aryl group which may be substituted or an aralkyl group which may be substituted, or $R^3$ and $R^4$ may combine with an adjacent nitrogen atom and form a nitrogen-containing heterocyclic group which may be substituted.

4. The compound as claimed in claim 3 wherein $R^3$ and $R^4$ are the same or different and are independently a hydrogen atom, a hydroxy group which may be substituted, a lower alkyl group which may be substituted or an acyl group, or $R^3$ and $R^4$ may combine with an adjacent nitrogen atom and form a nitrogen-containing heterocyclic group which may be substituted.

5. The compound as claimed in claim 3 wherein $R^3$ and $R^4$ are the same or different and are independently a hydrogen atom or a lower alkyl group which may be substituted.

6. The compound as claimed in claim 3 wherein $R^3$ is a hydrogen atom or a $C_{1-6}$ alkyl group, and $R^4$ is (i) a hydrogen atom or (ii) a $C_{1-6}$ alkyl group which may be substituted by a group selected from the group consisting of hydroxy, carboxyl, $C_{1-6}$ alkoxy-carbonyl, amino and mono- or d-$C_{1-6}$ alkyl amino, (iii) a $C_{6-14}$ aryl group which may be substituted by $C_{1-6}$ alkoxy or (iv) a $C_{7-16}$ aralkyl group which may be substituted by $C_{1-6}$ alkoxy or $C_{1-6}$ acylamino, or $R^3$ and $R^4$ combine with an adjacent nitrogen atom and form a 5 to 8 membered nitrogen-containing heterocyclic group which may be substituted by $C_{7-16}$ aralkyl.

7. The compound as claimed in claim 1 wherein the ring A is a benzene ring which is substituted by a lower alkylenedioxy.

8. The compound as claimed in claim 1 wherein the ring A is a $C_{6-10}$ aromatic hydrocarbon ring which is substituted by a $C_{1-3}$ alkylenedioxy.

9. The compound as claimed in claim 1 wherein the ring B is a benzene ring which may be substituted.

10. The compound as claimed in claim 1 wherein the ring B is (i) a $C_{6-12}$ aromatic hydrocarbon ring which may be substituted by a group selected from the group consisting of a halogen atom, optionally halogenated $C_{1-6}$ alkyl, optionally halogenated $C_{1-6}$ alkoxy and $C_{1-3}$ alkylenedioxy or (ii) a 5 to 8 membered heterocycle containing 1 to 3 hetero atoms selected from a nitrogen atom, an oxygen atom and a sulfur atom other than carbon atoms, and the 5 to 8 membered heterocycle may be substituted by $C_{1-6}$ alkyl.

11. The compound as claimed in claim 1 wherein $R^1$ is a group represented by the formula:

wherein $R^{3'}$ is a hydrogen atom or a $C_{1-6}$ alkyl group, and $R^{4'}$ is (i) a hydrogen atom, (ii) a $C_{1-6}$ alkyl group which may be substituted by a group selected from the group consisting of hydroxy, carboxyl, $C_{1-6}$ alkoxy-carbonyl, amino and mono- or di-$C_{1-6}$ alkylamino, (iii) a $C_{6-14}$ aryl group which may be substituted by $C_{1-6}$ alkoxy or (iv) a $C_{7-16}$ aralkyl group which may be substituted by $C_{1-6}$ alkoxy or $C_{1-6}$ acylamino, or $R^{3'}$ and $R^{4'}$ may combine with an adjacent nitrogen atom and form a 5 to 8 membered nitrogen-containing heterocyclic group which may be substituted by $C_{7-16}$ aralkyl;

$R^2$ is a hydrogen atom;

X is a methyne group which may be substituted by $C_{1-6}$ alkyl;

the ring A is a $C_{6-10}$ aromatic hydrocarbon ring which is substituted by a $C_{1-3}$ alkylenedioxy; and the ring B is (i) a $C_{6-10}$ aromatic hydrocarbon ring which may be substituted by a group selected from the group consisting of a halogen atom, optionally halogenated $C_{1-6}$ alkyl, optionally halogenated $C_{1-6}$ alkoxy and $C_{1-3}$ alkylenedioxy or (ii) a 5 to 8 membered heterocycle containing 1 to 3 hetero atoms selected from a nitrogen atom, an oxygen atom and a sulfur atom other than carbon atoms, and the 5 to 8 membered heterocycle may be substituted by $C_{1-6}$ alkyl.

12. The compound as claimed in claim 1 wherein $R^1$ is a group represented by the formula:

wherein $R^{3''}$ is a hydrogen atom and $R^{4''}$ is a hydrogen atom or a $C_{7-16}$ aralkyl group which may be substituted by $C_{1-6}$ alkoxy;

$R^2$ is a hydrogen atom;

X is a methyne group;

the ring A is a $C_{6-10}$ aromatic hydrocarbon ring which is substituted by $C_{1-3}$ alkylenedioxy; and the ring B is a $C_{6-10}$ aromatic hydrocarbon ring which may be substituted by a group selected from the group consisting of a halogen atom, $C_{1-6}$ alkoxy and $C_{1-3}$ alkylenedioxy.

13. A method for producing the compound as claimed in claim 1 or a ester thereof, or a pharmaceutically acceptable salt thereof which comprises subjecting a compound represented by the formula:

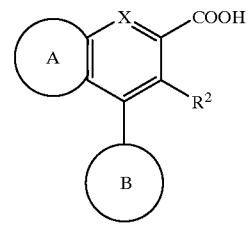

wherein each symbol is same as defined in claim 1, or a pharmaceutically acceptable salt thereof to an amidating reaction, and optionally followed by an acylating reaction.

14. A pharmaceutical composition which comprises the compound as claimed in claim 1 or a pharmaceutically acceptable salt thereof and a pharmaceutically acceptable carrier or excipient.

15. A method for inducing cell differentiation or enhancing induction of cell differentiation of a mammalian cell which comprises administering to said mammalian cell an effective amount of a compound represented by the formula:

(II)

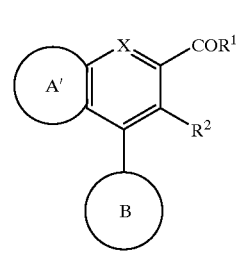

wherein a ring A' is a 4–10 membered homo-cycle which is substituted by a lower alkylenedioxy;

$R^1$ is an amino group which may be substituted by (a) a $C_{1-6}$ alkyl group, $C_{2-6}$ alkenyl group, $C_{2-6}$ alkynyl group, $C_{3-6}$ cycloalkyl group, $C_{6-14}$ aryl group or $C_{7-16}$ aralkyl group, which may be substituted by a group selected from the group consisting of (i) a halogen atom, (ii) $C_{1-3}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) optionally halogenated $C_{1-6}$ alkoxy, (x) optionally halogenated $C_{1-6}$ alkylthio, (xi) hydroxy, (xii) amino, (xiii) mono-$C_{1-6}$ alkyl amino, (xiv) di-$C_{1-6}$ alkyl amino, (xv) 5 or 6 membered cyclic amino, (xvi) acyl amino selected from $C_{1-6}$ alkoxy-carbonyl amino, mono-$C_{1-6}$ alkylaminocarbonyl amino, $C_{1-6}$ alkylcarbonyl amino and $C_{1-6}$ alkylsulfonyl amino, (xvii) $C_{1-6}$ alkylcarbonyl, (xviii) carboxyl, (xix) $C_{1-6}$ alkoxy-carbonyl, (xx) carbamoyl, (xxi) mono-$C_{1-6}$ alkyl-carbamoyl, (xxii) di-$C_{1-6}$ alkyl-carbamoyl, (xxiii) $C_{6-10}$ aryl-carbamoyl, (xxiv) sulfo, (xxv) $C_{1-6}$ alkyl sulfonyl, (xxvi) $C_{6-10}$ aryl and (xvii) $C_{6-10}$ aryloxy, (b) a hydroxy group which may be substituted by a $C_{1-6}$ alkyl group, $C_{2-6}$ alkenyl group, $C_{2-6}$ alkynyl group, $C_{3-6}$ cycloalkyl group, $C_{6-14}$ aryl group or $C_{7-16}$ aralkyl group, which may be substituted by a group selected from the group consisting of (i) a halogen atom, (ii) $C_{1-3}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) optionally halogenated $C_{1-6}$ alkoxy, (x) optionally halogenated $C_{1-6}$ alkylthio, (xi) hydroxy, (xii) amino, (xiii) mono-$C_{1-6}$ alkyl amino, (xiv) di-$C_{1-6}$ alkyl amino, (xv) 5 or 6 membered cyclic amino, (xvi) acyl amino selected from $C_{1-6}$ alkoxy-carbonyl amino, mono-$C_{1-6}$ alkylaminocarbonyl amino, $C_{1-6}$ alkylcarbonyl amino and $C_{1-6}$ alkylsulfonyl amino, (xvii) $C_{1-6}$ alkylcarbonyl, (xviii) carboxyl, (xix) $C_{1-6}$ alkoxy-carbonyl, (xx) carbamoyl, (xxi) mono-$C_{1-6}$ alkyl-carbamoyl, (xxii) di-$C_{1-6}$ alkyl-carbamoyl, (xxiii) $C_{6-10}$ aryl-carbamoyl, (xxiv) sulfo, (xxv) $C_{1-6}$ alkyl sulfonyl, (xxvi) $C_{6-10}$ aryl and (xxvii) $C_{6-10}$ aryloxy, or (c) an amino group which may be substituted by an acyl group represented by any one of the formula: —(C=O)—R$^7$, —SO$_2$—R$^7$, —(C=O)NR$^8$R$^7$, —(C=O)O—R$^7$, —(C=S)O—R$^7$ or —(C=S)NR$^8$R$^7$ wherein R$^7$ is (a) hydrogen atom or (b) a $C_{1-6}$ alkyl group, $C_{2-6}$ alkenyl group, $C_{2-6}$ alkynyl group, $C_{3-6}$ cycloalkyl group, $C_{6-14}$ aryl group or $C_{7-16}$ aralkyl group, which may be substituted by a group selected from the group consisting of (i) a halogen atom, (ii) $C_{1-3}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) optionally halogenated $C_{1-6}$ alkoxy, (x) optionally halogenated $C_{1-6}$ alkylthio, (xi) hydroxy, (xii) amino, (xiii) mono-$C_{1-6}$ alkyl amino, (xiv) di-$C_{1-6}$ alkyl amino, (xv) 5 or 6 membered cyclic amino, (xvi) acyl amino selected from $C_{1-6}$ alkoxy-carbonyl amino, mono-$C_{1-6}$ alkylaminocarbonyl amino, $C_{1-6}$ alkylcarbonyl amino and $C_{1-6}$ alkylsulfonyl amino, (xvii) $C_{1-6}$ alkylcarbonyl, (xviii) carboxyl, (xix) $C_{1-6}$ alkoxy-carbonyl, (xx) carbamoyl, (xxi) mono-$C_{1-6}$ alkyl-carbamoyl, (xxii) di-$C_{1-6}$ alkyl-carbamoyl, (xxiii) $C_{6-10}$ aryl-carbamoyl, (xxiv) sulfo, (xxv) $C_{1-6}$ alkyl sulfonyl, (xxvi) $C_{6-10}$ aryl and (xxvii) $C_{6-10}$ aryloxy, and R$^8$ is hydrogen atom or a $C_{1-6}$ alkyl group, or (d) R$^1$ is a group formed by removing a hydrogen atom from a nitrogen atom of a 5 to 9 membered nitrogen-containing heterocycle which may have 1 to 3 hetero atoms selected from a nitrogen atom, an oxygen atom and a sulfur atom, other than carbon atoms and one nitrogen atom, and the nitrogen-containing heterocycle may be substituted by a group selected from the group consisting of (i) a halogen atom, (ii) $C_{1-3}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) optionally halogenated $C_{1-6}$ alkoxy, (x) optionally halogenated $C_{1-6}$ alkylthio, (xi) hydroxy, (xii) amino, (xiii) mono-$C_{1-6}$ alkyl amino, (xiv) di-$C_{1-6}$ alkyl amino, (xv) 5 or 6 membered cyclic amino, (xvi) acyl amino selected from $C_{1-6}$ alkoxy-carbonyl amino, mono-$C_{1-6}$ alkylaminocarbonyl amino, $C_{1-6}$ alkylcarbonyl amino and $C_{1-6}$ alkylsulfonyl amino, (xvii) $C_{1-6}$ alkylcarbonyl, (xviii) carboxyl, (xix) $C_{1-6}$ alkoxy-carbonyl, (xx) carbamoyl, (xxi) mono-$C_{1-6}$ alkyl-carbamoyl, (xxii) di-$C_{1-6}$ alkyl-carbamoyl, (xxiii) $C_{6-10}$ aryl-carbamoyl, (xxiv) sulfo, (xxv) $C_{1-6}$ alkyl sulfonyl, (xxvi) $C_{6-10}$ aryl and (xxvii) $C_{6-10}$ aryloxy;

R$^2$ is a hydrogen atom;

X is a methyne group which may be substituted;

and a ring B is a homo- or hetero-cycle which may be substituted, or a pharmaceutically acceptable salt thereof to a mammalian cell.

16. A method as claimed in claim 15 wherein the ring A' is a 3 to 10 membered cyclic hydrocarbon.

17. A method of claim 15 wherein the mammalian cell is in a mammal suffering from a nerve disease or bone/joint disease.

18. A method as in claim 17 wherein said mammal is suffering from a nerve disease selected from a group consisting of nerve degeneration as found in cerebrovascular dementia, senile dementia, or Alzheimer's disease; amyotrophic lateral aclerosis; diabetic peripheral neuropathy; and Parkinson's disease.

19. The compound as claimed in claim 1, wherein the ring A is a homo-cycle which is substituted by a $C_{1-6}$ alkylenedioxy group.

20. The compound as claimed in claim 1, wherein R$^1$ is (i) an amino group which may be substituted by (a) a hydrocarbon group which may be substituted, (b) a hydroxy group which may be substituted or (c) an acyl group or (ii) a nitrogen-containing heterocyclic group which has a binding site on a ring-component nitrogen atom, optionally having substituents.

* * * * *